US011548938B2

(12) United States Patent
Sun et al.

(10) Patent No.: US 11,548,938 B2
(45) Date of Patent: Jan. 10, 2023

(54) DBPA ANTIBODIES AND USES THEREOF

(71) Applicant: Quidel Corporation, San Diego, CA (US)

(72) Inventors: Jason J. Sun, San Diego, CA (US); Jason McClure, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 86 days.

(21) Appl. No.: 16/546,113

(22) Filed: Aug. 20, 2019

(65) Prior Publication Data

US 2020/0062832 A1 Feb. 27, 2020

Related U.S. Application Data

(60) Provisional application No. 62/720,883, filed on Aug. 21, 2018.

(51) Int. Cl.
| | |
|---|---|
| *C07K 16/12* | (2006.01) |
| *G01N 33/569* | (2006.01) |
| *C07K 14/20* | (2006.01) |
| *C07K 14/435* | (2006.01) |

(52) U.S. Cl.
CPC ............ *C07K 16/12* (2013.01); *C07K 14/20* (2013.01); *C07K 14/43504* (2013.01); *G01N 33/56911* (2013.01); *C07K 2317/21* (2013.01); *C07K 2317/24* (2013.01); *C07K 2317/92* (2013.01); *C07K 2319/00* (2013.01); *G01N 2333/20* (2013.01); *G01N 2800/26* (2013.01)

(58) Field of Classification Search
None
See application file for complete search history.

(56) References Cited

U.S. PATENT DOCUMENTS

| | | |
|---|---|---|
| 6,214,355 B1 | 4/2001 | Guo et al. |
| 6,517,838 B1 | 2/2003 | Hook et al. |
| 2014/0274925 A1 | 9/2014 | Jin et al. |

FOREIGN PATENT DOCUMENTS

WO    WO 2018/017998 A1    1/2018

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, p. 12272-12273).*
Sela-Culang et al. (Frontiers in Immunology, 2013 vol. 4, article 302, pp. 1-13).*
Hagman et al., "Decorin-binding protein A (DbpA) of Borrelia burgdorferi is not protective when immunized mice are challenged via tick infestation and correlates with the lack of DbpA expression by B. burgdorferi in ticks", Infection and Immunity, vol. 68, No. 8, pp. 4759-4764 (2000).
Hanson et al., "Active and passive immunity against Borrelia burgdorferi decorin binding protein A (DbpA) protects against infection", Infection and Immunity, vol. 66, No. 5, pp. 2143-2153 (1998).
Intenational Search Report from International Application No. PCT/US2019/047328, 8 pages, dated Jan. 16, 2020.
Schuijt et al., "Lyme borreliosis vaccination: the facts, the challenge, the future", Trends in Parasitology, vol. 27, No. 1, pp. 40-47 (2011).
Schulte-Spechtel et al., "Molecular analysis of decorin-binding protein A (DbpA) reveals five major groups among European Borrelia burgdorferi sensu lato strains with impact for the development of serological assays and indicates lateral gene transfer of the dbpA gene", Int. J. Med. Microbiol., vol. 296, Suppl. 40, pp. 250-266 (2006).

* cited by examiner

*Primary Examiner* — Robert A Zeman
(74) *Attorney, Agent, or Firm* — McDermott Will and Emery LLP; Judy M. Mohr; Brett A. Schweers

(57) ABSTRACT

Embodiments of the present disclosure relate to chimeric antibodies which specifically bind to *Borrelia* decorin-binding protein A (DbpA) antigens and compositions or kits comprising such antibodies. The disclosure further relates to use of such antibodies in the detection of *Borrelia* sp. in samples, e.g., biological samples such as human blood and/or tissues of deer, ticks and other carriers of *Borrelia*. Embodiments of the disclosure further relate to diagnosis and/or therapy of Lyme disease using the chimeric antibodies and/or compositions containing the chimeric antibodies.

9 Claims, 6 Drawing Sheets

Specification includes a Sequence Listing.

SEQUENCE LISTING

```
<160> NUMBER OF SEQ ID NOS: 86

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Tyr Trp Met Tyr Trp
1               5

<210> SEQ ID NO 2
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Leu Asp Pro Asn Ser Gly Val Thr Lys Tyr Asn Glu Lys Phe Lys
1               5                   10                  15

Ser

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Asp Ser Trp Tyr Phe Asp Val
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ala Thr Gln Asp Ile Val Lys Asn Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ala Thr Glu Leu Ala Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Phe Tyr Ala Phe Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Asp Tyr Trp Ile Glu
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ile Leu Pro Gly Ser Gly Ser Thr Lys Asp Asn Glu Arg Phe Lys
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Glu Trp Gly Tyr Tyr Phe Asp Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ala Ser Gln Asp Val Ser Thr Ala Val Ala
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Trp Ala Ser Thr Arg His Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln His Tyr Ser Thr Pro Tyr Thr
1               5

<210> SEQ ID NO 13
```

<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe
            20                  25

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Trp Val Lys Gln Arg Pro Gly Arg Gly Leu Glu Trp Ile Gly
1               5                   10

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Lys Ala Thr Leu Thr Val Asp Lys Ser Ser Thr Ala Tyr Met Gln
1               5                   10                  15

Leu Ser Ser Leu Thr Ser Glu Asp Ser Ala Val Tyr Tyr Cys Val Arg
            20                  25                  30

Asp Asp Ser
        35

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Met Thr Gln Ser Pro Ser Ser Met Ser Ala Ser Leu Gly Asp Arg Ile
1               5                   10                  15

Thr Ile Thr Cys
            20

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Trp Tyr Gln Gln Lys Pro Gly Lys Pro Pro Ser Phe Leu Ile Tyr
1               5                   10                  15

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Gly Pro Ser Arg Phe Ser Gly Ser Gly Ser Gly Ser Asp Tyr Ser
1               5                   10                  15

Leu Thr Ile Asn Asn Leu Glu Ser Gln Asp Phe Ala Asp Tyr Phe Cys
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Ser Gly Ala Glu Leu Met Lys Pro Gly Ala
1               5                   10                  15

Ser Val Lys Leu Ser Cys Lys Ala Ala Gly Tyr Thr Phe Thr
            20                  25                  30

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Val Lys Gln Arg Pro Gly His Gly Leu Glu Trp Ile Gly
1               5                   10

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Ala Thr Phe Thr Ala Asp Thr Ser Ser Asn Thr Ala Tyr Met Gln
1               5                   10                  15

Leu Ser Ser Leu Thr Thr Glu Asp Ser Ala Ile Tyr Tyr Cys Ala Arg
            20                  25                  30

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Ile Val Met Thr Gln Ser His Lys Phe Met Ser Thr Ser Val Gly
1               5                   10                  15

```
Asp Arg Val Ser Ile Thr Cys
            20

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Tyr Gln Gln Lys Pro Gly Gln Ser Pro Lys Leu Leu Ile Tyr
1               5                   10                  15

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Val Pro Asp Arg Phe Thr Gly Ser Gly Ser Gly Thr Asp Tyr Thr
1               5                   10                  15

Leu Thr Ile Ser Ser Val Gln Ala Glu Asp Leu Ala Leu Tyr Tyr Cys
            20                  25                  30

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met Tyr Trp Val Lys Gln Arg Pro Gly Arg Gly Leu Glu Trp Ile
        35                  40                  45

Gly Arg Leu Asp Pro Asn Ser Gly Val Thr Lys Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Asp Asp Ser Trp Tyr Phe Asp Val
                100                 105

<210> SEQ ID NO 26
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Ile Gln Met Thr Gln Ser Pro Ser Ser Met Ser Ala Ser Leu Gly
```

```
1               5                   10                  15
Asp Arg Ile Thr Ile Thr Cys Gln Ala Thr Gln Asp Ile Val Lys Asn
                20                  25                  30

Leu Asn Trp Tyr Gln Gln Lys Pro Gly Lys Pro Pro Ser Phe Leu Ile
            35                  40                  45

Tyr Tyr Ala Thr Glu Leu Ala Glu Gly Val Pro Ser Arg Phe Ser Gly
        50                  55                  60

Ser Gly Ser Gly Ser Asp Tyr Ser Leu Thr Ile Asn Asn Leu Glu Ser
65                  70                  75                  80

Gln Asp Phe Ala Asp Tyr Phe Cys Leu Gln Phe Tyr Ala Phe Pro Leu
                85                  90                  95

Thr

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Ser Gly Ala Glu Leu Met Lys Pro Gly Ala
1               5                   10                  15

Ser Val Lys Leu Ser Cys Lys Ala Ala Gly Tyr Thr Phe Thr Asp Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Lys Asp Asn Glu Arg Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Glu Trp Gly Tyr Tyr Phe Asp Tyr
                100                 105

<210> SEQ ID NO 28
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95
```

Thr

<210> SEQ ID NO 29
<211> LENGTH: 19
<212> TYPE: PRT
<213> ORGANISM: Unknown
<220> FEATURE:
<223> OTHER INFORMATION: Description of Unknown:
      6G8 signal sequence

<400> SEQUENCE: 29

Met Gly Trp Ser Cys Ile Met Leu Phe Leu Ala Ala Thr Ala Thr Gly
1               5                   10                  15

Val His Ser

<210> SEQ ID NO 30
<211> LENGTH: 22
<212> TYPE: PRT
<213> ORGANISM: Unknown
<220> FEATURE:
<223> OTHER INFORMATION: Description of Unknown:
      6G8 signal sequence

<400> SEQUENCE: 30

Met Asp Met Arg Ala Pro Ala Gln Phe Leu Gly Ile Leu Leu Leu Trp
1               5                   10                  15

Phe Pro Gly Ala Arg Cys
            20

<210> SEQ ID NO 31
<211> LENGTH: 19
<212> TYPE: PRT
<213> ORGANISM: Unknown
<220> FEATURE:
<223> OTHER INFORMATION: Description of Unknown:
      8C10 signal sequence

<400> SEQUENCE: 31

Met Glu Trp Thr Trp Val Phe Leu Phe Leu Leu Ser Val Thr Ala Gly
1               5                   10                  15

Val His Ser

<210> SEQ ID NO 32
<211> LENGTH: 20
<212> TYPE: PRT
<213> ORGANISM: Unknown
<220> FEATURE:
<223> OTHER INFORMATION: Description of Unknown:
      8C10 signal sequence

<400> SEQUENCE: 32

Met Glu Ser Gln Ile Gln Ala Phe Val Phe Val Phe Leu Trp Leu Ser
1               5                   10                  15

Gly Val Asp Gly
            20

<210> SEQ ID NO 33
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Gly Trp Ser Cys Ile Met Leu Phe Leu Ala Ala Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Arg Tyr Trp Met Tyr Trp Val Lys Gln Arg Pro Gly Arg Gly Leu
        50                  55                  60

Glu Trp Ile Gly Arg Leu Asp Pro Asn Ser Gly Val Thr Lys Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Val Arg Asp Asp Ser Trp Tyr Phe Asp Val Trp Gly Thr
        115                 120                 125

Gly Thr Thr Val Thr Val Ser Ser Ala Lys Thr Thr Pro Pro Ser Val
        130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
                180                 185                 190

Leu Gln Ser Asp Leu Tyr Thr Leu Ser Ser Ser Val Thr Val Pro Ser
                195                 200                 205

Ser Thr Trp Pro Ser Gln Thr Val Thr Cys Asn Val Ala His Pro Ala
        210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
                260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Lys Pro
        290                 295                 300

Arg Glu Glu Gln Ile Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
                340                 345                 350

Lys Gly Arg Pro Lys Ala Pro Gln Val Tyr Thr Ile Val Tyr Ser Lys
        355                 360                 365

Leu Asn Val Gln Lys Ser Asn Trp Glu Ala Gly Asn Thr Phe Thr Cys
        370                 375                 380

Ser Val Leu His Glu Gly Leu His Asn His His Thr Glu Lys Ser Leu
385                 390                 395                 400

Ser Leu Ser Pro Gly Lys
                405
```

```
<210> SEQ ID NO 34
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Met Arg Ala Pro Ala Gln Phe Leu Gly Ile Leu Leu Leu Trp
1               5                   10                  15

Phe Pro Gly Ala Arg Cys Glu Ile Gln Met Thr Gln Ser Pro Ser Ser
            20                  25                  30

Met Ser Ala Ser Leu Gly Asp Arg Ile Thr Ile Thr Cys Gln Ala Thr
        35                  40                  45

Gln Asp Ile Val Lys Asn Leu Asn Trp Tyr Gln Lys Pro Gly Lys
    50                  55                  60

Pro Pro Ser Phe Leu Ile Tyr Tyr Ala Thr Glu Leu Ala Glu Gly Val
65                  70                  75                  80

Pro Ser Arg Phe Ser Gly Ser Gly Ser Gly Ser Asp Tyr Ser Leu Thr
                85                  90                  95

Ile Asn Asn Leu Glu Ser Gln Asp Phe Ala Asp Tyr Phe Cys Leu Gln
            100                 105                 110

Phe Tyr Ala Phe Pro Leu Thr Phe Gly Ala Gly Thr Lys Leu Glu Leu
        115                 120                 125

Arg Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Arg Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Gly Glu Cys
225                 230                 235

<210> SEQ ID NO 35
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Ala Gly Tyr Thr Phe
        35                  40                  45

Thr Asp Tyr Trp Ile Glu Trp Val Lys Gln Arg Pro Gly His Gly Leu
    50                  55                  60
```

Glu Trp Ile Gly Glu Ile Leu Pro Gly Ser Gly Ser Thr Lys Asp Asn
65                  70                  75                  80

Glu Arg Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Arg Glu Trp Gly Tyr Tyr Phe Asp Tyr Trp Gly
        115                 120                 125

Gln Gly Thr Thr Leu Thr Val Ser Ser Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Val Thr Val Pro
        195                 200                 205

Ser Ser Thr Trp Pro Ser Gln Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Lys
290                 295                 300

Pro Arg Glu Glu Gln Ile Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asn Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser Leu Ser Pro Gly Lys
450                 455                 460

<210> SEQ ID NO 36
<211> LENGTH: 234
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 36

```
Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Tyr
            100                 105                 110

Ser Thr Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Gly Glu Cys
225                 230
```

<210> SEQ ID NO 37
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
```

```
                85                  90                  95
Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 38
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 38

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met Tyr Trp Val Lys Gln Arg Pro Gly Arg Gly Leu Glu Trp Ile
        35                  40                  45

Gly Arg Leu Asp Pro Asn Ser Gly Val Thr Lys Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Asp Asp Ser Trp Tyr Phe Asp Val Trp Gly Thr Gly Thr Thr
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
        195                 200                 205

Lys Val Asp Lys Lys Ile Leu Pro Val Ile Ala Glu Leu Pro Pro Lys
    210                 215                 220

Val Ser Val Phe Val Pro Pro Arg Asp Gly Phe Phe Gly Asn Pro Arg
225                 230                 235                 240

Lys Ser Lys Leu Ile Cys Gln Ala Thr Gly Phe Ser Pro Arg Gln Ile
                245                 250                 255

Gln Val Ser Trp Leu Arg Glu Gly Lys Gln Val Gly Ser Gly Val Thr
            260                 265                 270

Thr Asp Gln Val Gln Ala Glu Ala Lys Glu Ser Gly Pro Thr Thr Tyr
        275                 280                 285

Lys Val Thr Ser Thr Leu Thr Ile Lys Glu Ser Asp Trp Leu Ser Gln
    290                 295                 300

Ser Met Phe Thr Cys Arg Val Asp His Arg Gly Leu Thr Phe Gln Gln
305                 310                 315                 320

Asn Ala Ser Ser Met Cys Val Pro Asp Gln Asp Thr Ala Ile Arg Val
                325                 330                 335

Phe Ala Ile Pro Pro Ser Phe Ala Ser Ile Phe Leu Thr Lys Ser Thr
            340                 345                 350

Lys Leu Thr Cys Leu Val Thr Asp Leu Thr Thr Tyr Asp Ser Val Thr
        355                 360                 365

Ile Ser Trp Thr Arg Gln Asn Gly Glu Ala Val Lys Thr His Thr Asn
    370                 375                 380

Ile Ser Glu Ser His Pro Asn Ala Thr Phe Ser Ala Val Gly Glu Ala
385                 390                 395                 400

Ser Ile Cys Glu Asp Asp Trp Asn Ser Gly Glu Arg Phe Thr Cys Thr
```

```
                    405                 410                 415
Val Thr His Thr Asp Leu Pro Ser Pro Leu Lys Gln Thr Ile Ser Arg
            420                 425                 430

Pro Lys Gly Val Ala Leu His Arg Pro Asp Val Tyr Leu Leu Pro Pro
            435                 440                 445

Ala Arg Glu Gln Leu Asn Leu Arg Glu Ser Ala Thr Ile Thr Cys Leu
            450                 455                 460

Val Thr Gly Phe Ser Pro Ala Asp Val Phe Val Gln Trp Met Gln Arg
465                 470                 475                 480

Gly Gln Pro Leu Ser Pro Glu Lys Tyr Val Thr Ser Ala Pro Met Pro
                485                 490                 495

Glu Pro Gln Ala Pro Gly Arg Tyr Phe Ala His Ser Ile Leu Thr Val
            500                 505                 510

Ser Glu Glu Glu Trp Asn Thr Gly Glu Thr Tyr Thr Cys Val Val Ala
            515                 520                 525

His Glu Ala Leu Pro Asn Arg Val Thr Glu Arg Thr Val Asp Lys Ser
            530                 535                 540

Thr Gly Lys Pro Thr Leu Tyr Asn Val Ser Leu Val Met Ser Asp Thr
545                 550                 555                 560

Ala Gly Thr Cys Tyr
                565

<210> SEQ ID NO 39
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Ser Gly Ala Glu Leu Met Lys Pro Gly Ala
1               5                   10                  15

Ser Val Lys Leu Ser Cys Lys Ala Ala Gly Tyr Thr Phe Thr Asp Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Lys Asp Asn Glu Arg Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Arg Glu Trp Gly Tyr Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
            130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190
```

```
Trp Pro Ser Gln Thr Val Thr Cys Asn Val Ala His Pro Ala Ser Ser
            195                 200                 205

Thr Lys Val Asp Lys Lys Ile Leu Pro Val Ile Ala Glu Leu Pro Pro
    210                 215                 220

Lys Val Ser Val Phe Val Pro Pro Arg Asp Gly Phe Phe Gly Asn Pro
225                 230                 235                 240

Arg Lys Ser Lys Leu Ile Cys Gln Ala Thr Gly Phe Ser Pro Arg Gln
                245                 250                 255

Ile Gln Val Ser Trp Leu Arg Glu Gly Lys Gln Val Gly Ser Gly Val
            260                 265                 270

Thr Thr Asp Gln Val Gln Ala Glu Ala Lys Glu Ser Gly Pro Thr Thr
    275                 280                 285

Tyr Lys Val Thr Ser Thr Leu Thr Ile Lys Glu Ser Asp Trp Leu Ser
290                 295                 300

Gln Ser Met Phe Thr Cys Arg Val Asp His Arg Gly Leu Thr Phe Gln
305                 310                 315                 320

Gln Asn Ala Ser Ser Met Cys Val Pro Asp Gln Asp Thr Ala Ile Arg
                325                 330                 335

Val Phe Ala Ile Pro Pro Ser Phe Ala Ser Ile Phe Leu Thr Lys Ser
            340                 345                 350

Thr Lys Leu Thr Cys Leu Val Thr Asp Leu Thr Thr Tyr Asp Ser Val
    355                 360                 365

Thr Ile Ser Trp Thr Arg Gln Asn Gly Glu Ala Val Lys Thr His Thr
370                 375                 380

Asn Ile Ser Glu Ser His Pro Asn Ala Thr Phe Ser Ala Val Gly Glu
385                 390                 395                 400

Ala Ser Ile Cys Glu Asp Asp Trp Asn Ser Gly Glu Arg Phe Thr Cys
                405                 410                 415

Thr Val Thr His Thr Asp Leu Pro Ser Pro Leu Lys Gln Thr Ile Ser
            420                 425                 430

Arg Pro Lys Gly Val Ala Leu His Arg Pro Asp Val Tyr Leu Leu Pro
    435                 440                 445

Pro Ala Arg Glu Gln Leu Asn Leu Arg Glu Ser Ala Thr Ile Thr Cys
450                 455                 460

Leu Val Thr Gly Phe Ser Pro Ala Asp Val Phe Val Gln Trp Met Gln
465                 470                 475                 480

Arg Gly Gln Pro Leu Ser Pro Glu Lys Tyr Val Thr Ser Ala Pro Met
                485                 490                 495

Pro Glu Pro Gln Ala Pro Gly Arg Tyr Phe Ala His Ser Ile Leu Thr
            500                 505                 510

Val Ser Glu Glu Glu Trp Asn Thr Gly Glu Thr Tyr Thr Cys Val Val
    515                 520                 525

Ala His Glu Ala Leu Pro Asn Arg Val Thr Glu Arg Thr Val Asp Lys
530                 535                 540

Ser Thr Gly Lys Pro Thr Leu Tyr Asn Val Ser Leu Val Met Ser Asp
545                 550                 555                 560

Thr Ala Gly Thr Cys Tyr
                565

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 40
aggtactgga tgtac                                                        15

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aggcttgatc ctaatagtgg tgttactaaa tacaatgaga agttcaagag c                 51

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gatgattcct ggtacttcga tgtc                                              24

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caggcaactc aagacattgt taagaattta aac                                    33

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tatgcaactg aactggcaga a                                                 21

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctacagtttt atgcgtttcc gctcacg                                           27

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactactgga tagag                                                           15

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gagattttac ctggaagtgg tagtactaag gacaatgaga ggttcaaggg c                   51

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agggagtggg gctactactt tgactac                                              27

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaggccagtc aggatgtgag tactgctgta gcc                                       33

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atttactggg catccacccg gcacact                                              27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cagcaacatt atagcactcc gtacacg                                              27

<210> SEQ ID NO 52
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caggtccaac tgcagcagcc tggggctgag cttgtgaagc ctggggcttc agtgaagctg    60
tcctgcaagg cttctggcta cactttcact                                     90

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgggtgaaac agaggcctgg acgaggcctt gagtggattg ga                       42

<210> SEQ ID NO 54
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
aaggccactc tgactgtaga caaatcctcc agcacagcct acatgcagct cagcagcctg    60
acatctgagg actctgcggt ctattattgt gtaagggatg attcc                   105

<210> SEQ ID NO 55
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gaaatccaga tgacccagtc tccatcctct atgtctgcat ctctgggaga cagaataacc    60
atcacttgc                                                            69

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tggtatcagc agaaaccagg gaaccccct tcattcctga tctat                     45

<210> SEQ ID NO 57
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aggggtccat caaggttcag tggcagtggg tctgggtcag actattctct gacaatcaac    60
aacctggagt ctcaagattt tgcagactat ttctgt                              96

<210> SEQ ID NO 58

```
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caggttcagc tgcagcagtc tggagctgag ctgatgaagc ctggggcctc agtgaagctt      60
tcctgcaagg ctgctggcta cacattcact                                      90

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgggtaaaac agaggcctgg acatggcctt gagtggattg ga                        42

<210> SEQ ID NO 60
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aaggccacat tcactgcaga tacatcctcc aacacagcct acatgcaact cagcagcctg      60
acaactgagg actctgccat ctattactgt gcaagg                               96

<210> SEQ ID NO 61
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gacattgtga tgacccagtc tcacaaattc atgtccacat cagtaggaga cagggtcagt      60
atcacctgc                                                             69

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tggtatcaac aaaaaccagg gcaatctcct aaactactga tttac                     45

<210> SEQ ID NO 63
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
```

```
ggagtccctg atcgcttcac aggcagtgga tctgggacag attatactct caccatcagc    60
agtgtgcagg ctgaagacct ggcactttat tactgt                              96

<210> SEQ ID NO 64
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atgggatgga gctgtatcat gctcttcttg gcagcaacag ctacaggtgt ccactcccag    60
gtccaactgc agcagcctgg ggctgagctt gtgaagcctg gggcttcagt gaagctgtcc   120
tgcaaggctt ctggctacac tttcactagg tactggatgt actgggtgaa acagaggcct   180
ggacgaggcc ttgagtggat tggaaggctt gatcctaata gtggtgttac taaatacaat   240
gagaagttca gagcaaggc cactctgact gtagacaaat cctccagcac agcctacatg   300
cagctcagca gcctgacatc tgaggactct gcggtctatt attgtgtaag ggatgattcc   360
tggtacttcg atgtctgggg cacagggacc acggtcaccg tctcctcagc caaaacgaca   420
cccccatctg tctatccact ggcccctgga tctgctgccc aaactaactc catggtgacc   480
ctgggatgcc tggtcaaggg ctatttccct gagccagtga cagtgacctg aactctgga   540 tccctgtcca gcggtgtgca caccttccca gctgtcctgc agtctgacct ctacactctg   600
agcagctcag tgactgtccc ctccagcacc tggcccagcc agaccgtcac ctgcaacgtt   660
gcccacccgg ccagcagcac caaggtggac aagaaaattg tgcccaggga ttgtggttgt   720
aagccttgca tatgtacagt cccagaagta tcatctgtct tcatcttccc cccaaagccc   780
aaggatgtgc tcaccattac tctgactcct aaggtcacgt gtgttgtggt agacatcagc   840
aaggatgatc ccgaggtcca gttcagctgg tttgtagatg atgtggaggt gcacacagct   900
cagacgaaac cccgggagga gcagatcaac agcactttcc gttcagtcag tgaacttccc   960
atcatgcacc aggactggct caatggcaag gagttcaaat gcagggtcaa cagtgcagct  1020
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacaa acttcttccc tgaagacatt actgtggagt ggcagtggaa tgggcagcca  1200
gcggagaact acaagaacac tcagcccatc atggacacag atggctctta cttcgtctac  1260
agcaagctca atgtgcagaa gagcaactgg gaggcaggaa atactttcac ctgctctgtg  1320
ttacatgagg gcctgcacaa ccaccatact gagaagagcc tctccctctc tcctggtaaa  1380
tga                                                                1383

<210> SEQ ID NO 65
<211> LENGTH: 710
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggacatga gggctcctgc tcagtttctt gggatcttgt tgctctggtt cccaggtgcc    60
agatgtgaaa tccagatgac ccagtctcca tcctctatgt ctgcatctct gggagacaga   120
```

```
ataaccatca cttgccaggc aactcaagac attgttaaga atttaaactg gtatcagcag      180
aaaccaggga aaccccttc attcctgatc tattatgcaa ctgaactggc agaagggtc       240 catcaaggtt cagtggcagt gggtctgggt cagactattc tctgacaatc aacaacctgg     300
agtctcaaga ttttgcagac tatttctgtc tacagtttta tgcgtttccg ctcacgttcg     360
gtgctgggac caagctggag ctgagacggg ctgatgctgc accaactgta tccatcttcc     420
caccatccag tgagcagtta acatctggag gtgcctcagt cgtgtgcttc ttgaacaact     480 tctacccag agacatcaat gtcaagtgga agattgatgg cagtgaacga caaaatggtg      540
tcctgaacag ttggactgat caggacagca agacagcac ctacagcatg agcagcaccc      600
tcacattgac caaggacgag tatgaacgac ataacagcta tcctgtgag gccactcaca      660 agacatcaac ttcacccatc gtcaagagct caacagggg agagtgttga                 710

<210> SEQ ID NO 66
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atggaatgga cctgggtctt tctcttcctc ctgtcagtaa ctgcaggtgt ccactcccag       60
gttcagctgc agcagtctgg agctgagctg atgaagcctg gggcctcagt gaagctttcc     120
tgcaaggctg ctggctacac attcactgac tactggatag agtgggtaaa acagaggcct     180
ggacatggcc ttgagtggat tggagagatt ttacctggaa gtggtagtac taaggacaat     240
gagaggttca aggcaaggc cacattcact gcagatacat cctccaacac agcctacatg     300
caactcagca gcctgacaac tgaggactct gccatctatt actgtgcaag agggagtgg     360 ggctactact ttgactactg gggccaaggc accactctca cagtctcctc agccaaaacg     420 acaccccat ctgtctatcc actggcccct ggatctgctg cccaaactaa ctccatggtg      480
accctgggat gcctggtcaa gggctatttc cctgagccag tgacagtgac ctggaactct     540
ctgagcagct cagtgactgt cccctccagc acctggccca gccagaccgt cacctgcaac     600
gttgcccacc cggccagcag caccaaggtg gacaagaaaa ttgtgcccag ggattgtggt     660
tgtaagcctt gcatatgtac agtcccagaa gtatcatctg tcttcatctt cccccccaaag   720 cccaaggatg tgctcaccat tactctgact cctaaggtca cgtgtgttgt ggtagacatc     780
agcaaggatg atcccgaggt ccagttcagc tggtttgtag atgatgtgga ggtgcacaca     840
gctcagacga aaccccggga ggagcagatc aacagcactt tccgttcagt cagtgaactt     900
cccatcatgc accaggactg gctcaatggc aaggagttca atgcagggt caacagtgca     960 gctttccctg cccccatcga gaaaaccatc tccaaaacca aggcagacc gaaggctcca     1020 caggtgtaca ccattccacc tcccaaggag cagatggcca aggataaagt cagtctgacc    1080
tgcatgataa caaacttctt ccctgaagac attactgtgg agtggcagtg gaatgggcag    1140
ccagcggaga actacaagaa cactcagccc atcatggaca cagatggctc ttacttcgtc    1200
tacagcaagc tcaatgtgca gaagagcaac tgggaggcag gaaatacttt cacctgctct    1260
gtgttacatg aggcctgca caaccaccat actgagaaga gcctctccct ctctcctggt    1320
aaatga                                                                1326

<210> SEQ ID NO 67
```

<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
atggagtcac agattcaggc atttgtattc gtgtttctct ggttgtctgg tgttgacgga    60
gacattgtga tgacccagtc tcacaaattc atgtccacat cagtaggaga cagggtcagt   120
atcacctgca aggccagtca ggatgtgagt actgctgtag cctggtatca acaaaaacca   180
gggcaatctc ctaaactact gatttactgg gcatccaccc ggcacactgg agtccctgat   240
cgcttcacag gcagtggatc tgggacagat tatactctca ccatcagcag tgtgcaggct   300
gaagacctgg cactttatta ctgtcagcaa cattatagca ctccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccagagaca tcaatgtcaa gtggaagatt gatggcagtg aacgacaaaa tggtgtcctg   540
aacagttgga ctgatcagga cagcaaagac agcacctaca gcatgagcag cacccctcaca  600
ttgaccaagg acgagtatga acgacataac agctatacct gtgaggccac tcacaagaca   660
tcaacttcac ccatcgtcaa gagcttcaac aggggagagt gttga                   705
```

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Gly Ser Gly
1

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Gly Ser Gly Gly
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Gly Ser Gly Ser Gly
1               5

<210> SEQ ID NO 71
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 71

Gly Ser Gly Gly Gly
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Gly Gly Ser
1               5

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Gly Ser
1

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ser Ser Ser Gly
1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Lys Lys Lys
1

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 76

His His His His His His
1               5

<210> SEQ ID NO 77
<211> LENGTH: 168
<212> TYPE: PRT
<213> ORGANISM: Unknown
<220> FEATURE:
<223> OTHER INFORMATION: Description of Unknown:
Immunogenic fragment

<400> SEQUENCE: 77

```
Ser Ser Gly Leu Thr Gly Ala Thr Lys Ile Arg Leu Glu Arg Ser Ala
1               5                   10                  15

Lys Asp Ile Thr Asp Glu Ile Asp Ala Ile Lys Lys Asp Ala Ala Leu
            20                  25                  30

Lys Gly Val Asn Phe Asp Ala Phe Lys Asp Lys Lys Thr Gly Ser Gly
        35                  40                  45

Val Ser Glu Asn Pro Phe Ile Leu Glu Ala Lys Val Arg Ala Thr Thr
    50                  55                  60

Val Ala Glu Lys Phe Val Ile Ala Ile Glu Glu Glu Ala Thr Lys Leu
65                  70                  75                  80

Lys Glu Thr Gly Ser Ser Gly Glu Phe Ser Ala Met Tyr Asp Leu Met
                85                  90                  95

Phe Glu Val Ser Lys Pro Leu Gln Lys Leu Gly Ile Gln Glu Met Thr
            100                 105                 110

Lys Thr Val Ser Asp Ala Ala Glu Glu Asn Pro Pro Thr Thr Ala Gln
        115                 120                 125

Gly Val Leu Glu Ile Ala Lys Lys Met Arg Glu Lys Leu Gln Arg Val
    130                 135                 140

His Thr Lys Asn Tyr Cys Thr Leu Lys Lys Lys Glu Asn Ser Thr Phe
145                 150                 155                 160

Thr Asp Glu Lys Cys Lys Asn Asn
                165
```

<210> SEQ ID NO 78
<211> LENGTH: 191
<212> TYPE: PRT
<213> ORGANISM: Borrelia burgdorferi

<400> SEQUENCE: 78

```
Met Ile Lys Cys Asn Asn Lys Thr Phe Asn Asn Leu Leu Lys Leu Thr
1               5                   10                  15

Ile Leu Val Asn Leu Leu Ile Ser Cys Gly Leu Thr Gly Ala Thr Lys
            20                  25                  30

Ile Arg Leu Glu Arg Ser Ala Lys Asp Ile Thr Asp Glu Ile Asp Ala
        35                  40                  45

Ile Lys Lys Asp Ala Ala Leu Lys Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Lys
        115                 120                 125

Leu Gly Ile Gln Glu Met Thr Lys Thr Val Ser Asp Ala Ala Glu Glu
    130                 135                 140
```

```
Asn Pro Pro Thr Thr Ala Gln Gly Val Leu Glu Ile Ala Lys Lys Met
145                 150                 155                 160

Arg Glu Lys Leu Gln Arg Val His Thr Lys Asn Tyr Cys Thr Leu Lys
                165                 170                 175

Lys Lys Glu Asn Ser Thr Phe Thr Asp Glu Lys Cys Lys Asn Asn
        180                 185                 190

<210> SEQ ID NO 79
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Asn
            20                  25                  30

Leu Asn Trp Tyr Gln Gln Lys Pro Gly Lys Pro Pro Ser Phe Leu Ile
        35                  40                  45

Tyr Tyr Ala Thr Glu Leu Ala Glu Gly Val Pro Ser Arg Phe Ser Gly
    50                  55                  60

Ser Gly Ser Gly Ser Asp Tyr Ser Leu Thr Ile Asn Asn Leu Glu Ser
65                  70                  75                  80

Gln Asp Phe Ala Asp Tyr Phe Cys Leu Gln Phe Tyr Ala Phe Pro Leu
                85                  90                  95

Thr Phe Gly Ala Gly Thr Lys Leu Glu Leu Arg Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Arg Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
    210

<210> SEQ ID NO 80
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30
```

```
Trp Met Tyr Trp Val Lys Gln Arg Pro Gly Arg Gly Leu Glu Trp Ile
        35                  40                  45

Gly Arg Leu Asp Pro Asn Ser Gly Val Thr Lys Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Asp Asp Ser Trp Tyr Phe Asp Val Trp Gly Thr Gly Thr Thr
                100                 105                 110

Val Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
        130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
                180                 185                 190

Pro Ser Gln Thr Val Thr Cys Asn Val Ala His Pro Ala Ser Ser Thr
            195                 200                 205

Lys Val Asp Lys Lys Ile Leu Pro Val Ile Ala Glu Leu Pro Pro Lys
        210                 215                 220

Val Ser Val Phe Val Pro Pro Arg Asp Gly Phe Gly Asn Pro Arg
225                 230                 235                 240

Lys Ser Lys Leu Ile Cys Gln Ala Thr Gly Phe Ser Pro Arg Gln Ile
                245                 250                 255

Gln Val Ser Trp Leu Arg Glu Gly Lys Gln Val Gly Ser Gly Val Thr
            260                 265                 270

Thr Asp Gln Val Gln Ala Glu Ala Lys Glu Ser Gly Pro Thr Thr Tyr
        275                 280                 285

Lys Val Thr Ser Thr Leu Thr Ile Lys Glu Ser Asp Trp Leu Ser Gln
    290                 295                 300

Ser Met Phe Thr Cys Arg Val Asp His Arg Gly Leu Thr Phe Gln Gln
305                 310                 315                 320

Asn Ala Ser Ser Met Cys Val Pro Asp Gln Asp Thr Ala Ile Arg Val
                325                 330                 335

Phe Ala Ile Pro Pro Ser Phe Ala Ser Ile Phe Leu Thr Lys Ser Thr
            340                 345                 350

Lys Leu Thr Cys Leu Val Thr Asp Leu Thr Thr Tyr Asp Ser Val Thr
        355                 360                 365

Ile Ser Trp Thr Arg Gln Asn Gly Glu Ala Val Lys Thr His Thr Asn
    370                 375                 380

Ile Ser Glu Ser His Pro Asn Ala Thr Phe Ser Ala Val Gly Glu Ala
385                 390                 395                 400

Ser Ile Cys Glu Asp Asp Trp Asn Ser Gly Glu Arg Phe Thr Cys Thr
                405                 410                 415

Val Thr His Thr Asp Leu Pro Ser Pro Leu Lys Gln Thr Ile Ser Arg
                420                 425                 430

Pro Lys Gly Val Ala Leu His Arg Pro Asp Val Tyr Leu Leu Pro Pro
        435                 440                 445
```

```
Ala Arg Glu Gln Leu Asn Leu Arg Glu Ser Ala Thr Ile Thr Cys Leu
        450                 455                 460

Val Thr Gly Phe Ser Pro Ala Asp Val Phe Val Gln Trp Met Gln Arg
465                 470                 475                 480

Gly Gln Pro Leu Ser Pro Glu Lys Tyr Val Thr Ser Ala Pro Met Pro
                485                 490                 495

Glu Pro Gln Ala Pro Gly Arg Tyr Phe Ala His Ser Ile Leu Thr Val
            500                 505                 510

Ser Glu Glu Trp Asn Thr Gly Glu Thr Tyr Thr Cys Val Val Ala
        515                 520                 525

His Glu Ala Leu Pro Asn Arg Val Thr Glu Arg Thr Val Asp Lys Ser
    530                 535                 540

Thr Gly Lys Pro Thr Leu Tyr Asn Val Ser Leu Val Met Ser Asp Thr
545                 550                 555                 560

Ala Gly Thr Cys Tyr
                565

<210> SEQ ID NO 81
<211> LENGTH: 5
<212> TYPE: PRT
<213> ORGANISM: Unknown
<220> FEATURE:
<223> OTHER INFORMATION: Description of Unknown:
      DbpA sequence

<400> SEQUENCE: 81

Glu Asn Ser Thr Phe
1               5

<210> SEQ ID NO 82
<211> LENGTH: 5
<212> TYPE: PRT
<213> ORGANISM: Unknown
<220> FEATURE:
<223> OTHER INFORMATION: Description of Unknown:
      DbpA sequence

<400> SEQUENCE: 82

Lys Cys Lys Asn Asn
1               5

<210> SEQ ID NO 83
<211> LENGTH: 9
<212> TYPE: PRT
<213> ORGANISM: Unknown
<220> FEATURE:
<223> OTHER INFORMATION: Description of Unknown:
      DbpA sequence

<400> SEQUENCE: 83

Asn Thr Glu Asp Ser Thr Ala Lys Ser
1               5

<210> SEQ ID NO 84
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Ser Gly
      Gly Ser" repeating units
```

-continued

<400> SEQUENCE: 84

Gly Ser Gly Gly Ser Gly Ser Gly Gly Ser Gly Ser Gly Gly Ser Gly
1               5                   10                  15

Ser Gly Gly Ser Gly Ser Gly Gly Ser Gly Ser Gly Gly Ser Gly Ser
                20                  25                  30

Gly Gly Ser Gly Ser Gly Gly Ser Gly Ser Gly Gly Ser Gly Ser Gly
            35                  40                  45

Gly Ser
    50

<210> SEQ ID NO 85
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 85

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser
            35                  40

<210> SEQ ID NO 86
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Gly Trp Ser Cys Ile Met Leu Phe Leu Ala Ala Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Arg Tyr Trp Met Tyr Trp Val Lys Gln Arg Pro Gly Arg Gly Leu
        50                  55                  60

Glu Trp Ile Gly Arg Leu Asp Pro Asn Ser Gly Val Thr Lys Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Val Arg Asp Asp Ser Trp Tyr Phe Asp Val Trp Gly Thr
        115                 120                 125

Gly Thr Thr Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr

-continued

```
145                 150                 155                 160
Leu Gly Cys Leu Val Lys Gly Tyr Phe Pro Glu Pro Val Thr Val Thr
            165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
            195                 200                 205

Ser Thr Trp Pro Ser Gln Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
            275                 280                 285

Ser Trp Phe Val Asp Asp Val Glu Val His Thr Ala Gln Thr Lys Pro
    290                 295                 300

Arg Glu Glu Gln Ile Asn Ser Thr Phe Arg Ser Val Ser Glu Leu Pro
305                 310                 315                 320

Ile Met His Gln Asp Trp Leu Asn Gly Lys Glu Phe Lys Cys Arg Val
            325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
            355                 360                 365

Glu Gln Met Ala Lys Asp Lys Val Ser Leu Thr Cys Met Ile Thr Asn
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
            405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
            435                 440                 445

His Thr Glu Lys Ser Leu Ser Leu Ser Pro Gly Lys
    450                 455                 460
```

DBPA ANTIBODIES AND USES THEREOF

CROSS-REFERENCE TO RELATED APPLICATIONS

This application claims the benefit of U.S. Provisional Application No. 62/720,883, filed Aug. 21, 2018, which is incorporated by reference herein.

TECHNICAL FIELD

Embodiments of the present disclosure relate to the field of zoology and molecular diagnostics. More specifically, embodiments of the present disclosure relate to antibodies that bind specifically to Borrelia antigens, e.g., decorin-binding protein A (DbpA) of Borrelia burgdorferi. The disclosure additionally relates to use of such antibodies or antigen-binding fragments in the detection of DbpA antigens in biological samples for diagnosing diseases mediated by Borrelia sp., e.g., Lyme disease, including, therapy of such diseases.

REFERENCE TO SEQUENCE LISTING, TABLE OR COMPUTER PROGRAM

A Sequence Listing is being submitted electronically via EFS in the form of a text file, created Aug. 20, 2019, and named "041896-1163_8134_US00_SL.txt" (68,836 bytes), the contents of which are incorporated herein by reference in their entirety.

STATEMENT OF BIOLOGICAL DEPOSIT

Mouse hybridoma cell lines identified herein as clones 5H3, 4G9, and 1D12 have been deposited with the International Depository of Canada, 1015 Arlington Street, Winnipeg, Manitoba, Canada on Aug. 10, 2018, and given the accession numbers of 100818-03, 100818-02, and 100818-01, respectively.

BACKGROUND

Lyme disease (LD), which is caused by infection with the tick-borne spirochete Borrelia burgdorferi, is a common vector-borne disease in North America (Shapiro et al., N Engl J Med., 370, 1724-1731, 2014). Although North American LD is attributable to B. burgdorferi, European and in Asian LD may be additionally caused by B. afzelii, B. garinii, and other species related to B. burgdorferi. In highly endemic regions of the United States, the annual incidence of infection may be as high as 1-3% with a cumulative prevalence as high as 7-15% (Tugwell et al., Ann Intern Med., 127, 1109-1123, 1997). In Europe, the highest incidence was reported in southern Sweden at about 0.46% (Sykes et al., J Public Health (Oxf), 39, 74-81, 2017).

Difficulties in diagnosis have long complicated the treatment of LD, as the bite of an infected tick may go unnoticed by the patient, and the clinical manifestations of LD can significantly vary amongst diagnosed patients (Steere et al., J. Clin. Invest. 113, 1093-1101, 2004). In the majority of cases, the diagnosis of confirmed early Lyme disease is based on identification of the hallmark erythema migrans (EM) rash, which may occur in isolation or in conjunction with viral-like symptoms such as fever, malaise, fatigue, and generalized achiness. However, since these primary symptoms are also associated with other viral infections, misdiagnosis is common. Moreover, about 16% of the patients do not present any primary symptoms (Steere et al., Am J Med., 114, 58-62, 2003). These misdiagnosed and/or undiagnosed subjects are at grave risk of developing severe secondary complications, including, systemic harm to integumentary, musculoskeletal, neurologic, and cardiovascular systems.

Additionally, although antibiotic therapy (e.g., i.v. ceftriaxone followed by oral doxycycline) is highly effective, especially if administered in the early stages of LD, serious complications can result from false diagnoses (Lantos et al., Infect Dis Clin North Am., 29, 325-340, 2015). There is no commercially available vaccine for human LD, so the development of accurate, sensitive laboratory diagnosis is an important goal of LD research.

Currently available commercial assays in the United States are either based on whole bacteria cell extracts, such as the ELISA and immunoblotting assays, or on a single antigen ELISA (Aguero-Rosenfeld, Clin. Microbiol. Rev., 18, 484-509, 2005). The whole cell assays are usually used as a two-tiered test. First, a more sensitive, typically a whole cell ELISA, is used. This is followed by the more specific Western blot, if the ELISA is positive or equivocal (Marques et al., Infect Dis Clin North Am., 29, 295-307, 2015). Together these assays have served for years as the standard for serodiagnosis, but there remain trade-offs between sensitivity and specificity to minimize false-positive results. One drawback of the two-tiered, sequential test procedure is the time it takes and the greater expense for two assays. Another problem with whole cell assays is a lack of standardization between tests of different manufacturers. The variables include different strains of B. burgdorferi that are used, different conditions for cultivating the organisms, and different methods for identifying the key antigens on blots.

Assays based on detection of antigens, such as the flagellin protein FlaB, or combinations of recombinant proteins have been used in literature. Current laboratory based serologic assays employ the C6 ELISA or a two-tier test comprised of C6, whole-cell or recombinant antigen ELISA followed by Western blot containing a number of B. burgdorferi antigens such as VlsE, p100, p66, p58, p45, p41, p39, p30/31, p28 and p18. The sensitivity of these assays varies between 35-56% for early stage I, 73-77% for early stage II and 96-100% for late stage III disease (Nayak et al., Sci Rep., 6, 35069, 2016). However, only 10 to 50% of patients with culture confirmed very early localized LD (e.g., EM rash<7 days) presented a detectable antibody response. To overcome these drawbacks, lab-on-chip (LOC) microfluidic devices utilizing a plurality of antigens have been developed (Nayak et al., supra; OPKO Health, Inc, Miami, Fla., USA). However, the sensitivity and specificity achieved with such LOC systems provides marginal improvement over existing assays (84% and 92%, respectively).

Accordingly, there is an urgent need for new or improved compositions and systems for the diagnosis and therapy of Lyme disease. Ideally, such diagnostic compositions can be easily deployed in point-of-care instruments and systems for the testing of samples for Borrelia antigens with improved sensitivity and specificity compared to existing products.

BRIEF SUMMARY

In one aspect, an antibody or an antigen-binding fragment thereof is provided, which comprises a variable heavy chain (VH) comprising $FR_{H1}$-$CDR_{H1}$-$FR_{H2}$-$CDR_{H2}$-$FR_{H3}$-$CDR_{H3}$, optionally together with a variable light chain (VL) comprising $FR_{L1}$-$CDR_{L1}$-$FR_{L2}$-$CDR_{L2}$-$FR_{L3}$-$CDR_{L3}$, wherein, FR$_1$, FR$_2$, and FR$_3$, each, independently of one another, and independently from the inclusion thereof in the VH or VL chain, comprise antibody framework regions (FR) or are absent; and CDR$_1$, CDR$_2$, and CDR$_3$, each, independently from one another, comprise antibody complementary determining regions (CDRs), wherein CDR$_{H1}$ comprises a polypeptide comprising, consisting essentially of, or consisting of a polypeptide having at least 80%, 90%, or 95% sequence identity to the amino acid sequence RYWMYW (SEQ ID NO: 1) or DYWIE (SEQ ID NO: 7);

CDR$_{H2}$ comprises a polypeptide comprising, consisting essentially of, or consisting of a polypeptide having at least 80%, 90%, or 95% sequence identity to the amino acid sequence RLDPNSGVTKYNEKFKS (SEQ ID NO: 2) or EILPGSGSTKDNERFKG (SEQ ID NO: 8);

CDR$_{H3}$ comprises a polypeptide comprising, consisting essentially of, or consisting of a polypeptide having at least 80%, 90%, or 95% sequence identity to the amino acid sequence DDSWYFDV (SEQ ID NO: 3) or REWGYYFDY (SEQ ID NO: 9);

CDR$_{L1}$ comprises a polypeptide comprising, consisting essentially of, or consisting of a polypeptide having at least 80%, 90%, or 95% sequence identity to the amino acid sequence QATQDIVKNLN (SEQ ID NO: 4) or KASQDVSTAVA (SEQ ID NO: 10);

CDR$_{L2}$ comprises a polypeptide comprising, consisting essentially of, or consisting of a polypeptide having at least 80%, 90%, or 95% sequence identity to the amino acid sequence YATELAE (SEQ ID NO: 5) or IYWASTRHT (SEQ ID NO: 11); and CDR$_{L3}$ comprises a polypeptide comprising, consisting essentially of, or consisting of a polypeptide having at least 80%, 90%, or 95% sequence identity to the amino acid sequence LQFYAFPLT (SEQ ID NO: 6) or QQHYSTPYT (SEQ ID NO: 12).

In one embodiment, the antibody or the antigen-binding fragment comprises the variable heavy chain (VH) and the variable light chain (VL).

In one embodiment, the antibody or the antigen-binding fragment comprises at least 1, at least 2, or all least 3 framework regions (FR).

In one embodiment, the CDR$_{H1}$ comprises a polypeptide comprising, consisting essentially of, or consisting of a polypeptide having the amino acid sequence RYWMYW (SEQ ID NO: 1) or DYWIE (SEQ ID NO: 7); CDR$_{H2}$ comprises a polypeptide comprising, consisting essentially of, or consisting of a polypeptide having the amino acid sequence RLDPNSGVTKYNEKFKS (SEQ ID NO: 2) or EILPGSGSTKDNERFKG (SEQ ID NO: 8); CDR$_{H3}$ comprises a polypeptide comprising, consisting essentially of, or consisting of a polypeptide having the amino acid sequence DDSWYFDV (SEQ ID NO: 3) or REWGYYFDY (SEQ ID NO: 9); wherein, CDR$_{L1}$ comprises a polypeptide comprising, consisting essentially of, or consisting of a polypeptide having the amino acid sequence QATQDIVKNLN (SEQ ID NO: 4) or KASQDVSTAVA (SEQ ID NO: 10); CDR$_{L2}$ comprises a polypeptide comprising, consisting essentially of, or consisting of a polypeptide having the amino acid sequence YATELAE (SEQ ID NO: 5) or IYWASTRHT (SEQ ID NO: 11); and CDR$_{L3}$ comprises a polypeptide comprising, consisting essentially of, or consisting of a polypeptide having the amino acid sequence LQFYAFPLT (SEQ ID NO: 6) or QQHYSTPYT (SEQ ID NO: 12).

In some embodiments, the disclosure relates to an antibody or an antigen-binding fragment thereof comprising a variable heavy chain (VH) comprising FR$_{H1}$-CDR$_{H1}$-FR$_{H2}$-CDR$_{H2}$-FR$_{H3}$-CDR$_{H3}$ and a variable light chain (VL) comprising FR$_{L1}$-CDR$_{L1}$-FR$_{L2}$-CDR$_{L2}$-FR$_{L3}$-CDR$_{L3}$, wherein, FR$_1$, FR$_2$, and FR$_3$, each, independently of one another, comprise antibody framework regions (FR) or are absent; and CDR$_1$, CDR$_2$, and CDR$_3$, each, independently from one another, comprise antibody complementary determining regions (CDRs), wherein CDR$_{H1}$ comprises a polypeptide comprising, consisting essentially of, or consisting of a polypeptide having at least 80%, 90%, or 95% sequence identity to the amino acid sequence SEQ ID NO: 1 or SEQ ID NO: 7; CDR$_{H2}$ comprises a polypeptide comprising, consisting essentially of, or consisting of a polypeptide having at least 80%, 90%, or 95% sequence identity to the amino acid sequence SEQ ID NO: 2 or SEQ ID NO: 8; and CDR$_{H3}$ comprises a polypeptide comprising, consisting essentially of, or consisting of a polypeptide having at least 80%, 90%, or 95% sequence identity to the amino acid sequence SEQ ID NO: 3 or SEQ ID NO: 9; and wherein, CDR$_{L1}$ comprises a polypeptide comprising, consisting essentially of, or consisting of a polypeptide having at least 80%, 90%, or 95% sequence identity to the amino acid sequence SEQ ID NO: 4 or SEQ ID NO: 10; CDR$_{L2}$ comprises a polypeptide comprising, consisting essentially of, or consisting of a polypeptide having at least 80%, 90%, or 95% sequence identity to the amino acid sequence SEQ ID NO: 5 or SEQ ID NO: 11; and CDR$_{L3}$ comprises a polypeptide comprising, consisting essentially of, or consisting of a polypeptide having at least 80%, 90%, or 95% sequence identity to the amino acid sequence SEQ ID NO: 6 or SEQ ID NO: 12.

In some embodiments, the disclosure relates to one of the foregoing antibodies or antigen-binding fragments thereof comprising at least 1, at least 2, or all least 3 framework regions (FR).

In some embodiments, the disclosure relates to an antibody or an antigen-binding fragment thereof comprising, consisting essentially of, or consisting of the polypeptide sequences set forth in SEQ ID Nos: 1-6 or the polypeptide sequences set forth in SEQ ID NOs: 7-12.

In some embodiments, the disclosure relates to an antibody or an antigen-binding fragment thereof selected from (a) an antibody or an antigen-binding fragment thereof comprising CDR$_{1-3}$ of the VH chain comprising SEQ ID NOs: 1-3 and CDR$_{1-3}$ of the VL chain comprising SEQ ID NOs: 4-6; and (b) an antibody or an antigen-binding fragment thereof comprising CDR$_{1-3}$ of the VH chain comprising SEQ ID NOs: 7-9 and CDR$_{1-3}$ of the VL chain comprising SEQ ID NOs: 10-12.

In some embodiments, the disclosure relates to an antibody or an antigen-binding fragment thereof selected from an antibody or an antigen-binding fragment thereof comprising (1) a VH chain comprising the sequence set forth in SEQ ID NO: 33 or a fragment thereof; and (2) a VL chain comprising the sequence set forth in SEQ ID NO: 34 or a fragment thereof.

In some embodiments, the disclosure relates to an antibody or an antigen-binding fragment thereof selected from an antibody or an antigen-binding fragment thereof comprising (1) a VH chain comprising the sequence set forth in SEQ ID NO: 31 or a fragment thereof; and (2) a VL chain comprising the sequence set forth in SEQ ID NO: 32 or a fragment thereof.

In some embodiments, the disclosure relates to an antibody or an antigen-binding fragment thereof which comprises a single chain antibody fragment (scFV), an Fab fragment, or an F(ab')2 fragment.

In some embodiments, the disclosure relates to an antibody or an antigen-binding fragment thereof which comprises (a) the structure $FR_{H1}$-$CDR_{H1}$-$FR_{H2}$-$CDR_{H2}$-$FR_{H3}$-$CDR_{H3}$-L-$FR_{L1}$-$CDR_{L1}$-$FR_{L2}$-$CDR_{L2}$-$FR_{L3}$-$CDR_{L3}$; or (b) the structure $FR_{L1}$-$CDR_{L1}$-$FR_{L2}$-$CDR_{L2}$-$FR_{L3}$-$CDR_{L3}$-L-$FR_{H1}$-$CDR_{H1}$-$FR_{H2}$-$CDR_{H2}$-$FR_{H3}$-$CDR_{H3}$; wherein, L is a linker or absent; $FR_1$, $FR_2$, and $FR_3$, are each, independently of one another, antibody framework regions (FR) or absent; and $CDR_1$, $CDR_2$, and $CDR_3$, each, independently from one another, comprise antibody complementary determining regions (CDRs) whose meanings are provided above.

In some embodiments, the disclosure relates to an antibody or an antigen-binding fragment thereof which comprises the structure $FR_{H1}$-$CDR_{H1}$-$FR_{H2}$-$CDR_{H2}$-$FR_{H3}$-$CDR_{H3}$-L-$FR_{L1}$-$CDR_{L1}$-$FR_{L2}$-$CDR_{L2}$-$FR_{L3}$-$CDR_{L3}$; wherein, L is a linker or absent; $FR_1$, $FR_2$, and $FR_3$, are each, independently of one another, antibody framework regions (FR) or absent; and $CDR_1$, $CDR_2$, and $CDR_3$, each, independently from one another, comprise antibody complementary determining regions (CDRs) whose meanings are provided above.

In some embodiments, the disclosure relates to an antibody or an antigen-binding fragment thereof which binds to a polypeptide comprising at least 80%, at least 90%, at least 95% or at least 99% sequence identity to a polypeptide comprising, consisting essentially of, or consisting of the amino acid sequence set forth in SEQ ID NO: 77, or an immunogenic fragment thereof, where SEQ ID NO: 77 is SSGLTGATKIRLERSAKDITDEIDAIKK-DAALKGVNFDAFKDKKTGSGVSENPFILEAKV RAT-TVAEKFVIAIEEEATKLKETGSSGEFSAMYDLMFEV-SKPLQKLGIQEMTKTVSDAAE ENPPTTAQGVLEIAKKMREKLQRVHTKNYC-TLKKKENSTFTDEKCKNN (SEQ ID NO: 77).

In some embodiments, the disclosure relates to an antibody or an antigen-binding fragment of the foregoing or following paragraphs, wherein the antibody further comprises a signal peptide and optionally a label, e.g., a detectable label.

In some embodiments, the disclosure relates to a composition comprising an antibody or an antigen-binding fragment of the foregoing or following paragraphs, and a carrier.

In some embodiments, the disclosure relates to a pharmaceutical composition comprising an antibody or an antigen-binding fragment of the foregoing or following paragraphs, and a pharmaceutically acceptable carrier.

In some embodiments, the disclosure relates to a kit comprising, in one or more packages, an antibody or an antigen-binding fragment of the foregoing or following paragraphs, and a container, optionally together with instructions for using the kit.

In some embodiments, the disclosure relates to an antibody or an antigen-binding fragment of the foregoing or following paragraphs, which is not a naturally-occurring antibody or an antigen-binding fragment thereof.

In some embodiments, the disclosure relates to an antibody or an antigen-binding fragment of the foregoing or following paragraphs, which is a synthetic or a recombinant antibody or an antigen-binding fragment thereof.

In some embodiments, the disclosure relates to an antibody or an antigen-binding fragment of the foregoing or following paragraphs, which is a chimeric or humanized antibody or an antigen-binding fragment thereof.

In some embodiments, the disclosure relates to an antibody or an antigen-binding fragment of the foregoing or following paragraphs, which is an immunoglobulin G (IgG), immunoglobulin M (IgM), immunoglobulin A (IgA), immunoglobulin D (IgD), or immunoglobulin E (IgE) or an antigen-binding fragment thereof, preferably a chimeric IgG, IgM, IgE, IgA, IgD or IgE.

In some embodiments, the disclosure relates to an antibody or an antigen-binding fragment of the foregoing or following paragraphs, which is a chimeric IgM antibody or an antigen-binding fragment thereof.

In some embodiments, the disclosure relates to a fusion protein comprising an antibody or an antibody-binding fragment thereof of the foregoing or following paragraphs and a heterologous protein.

In some embodiments, the disclosure relates to an article comprising an antibody or an antibody-binding fragment thereof of the foregoing or following paragraphs and a surface.

In some embodiments, the disclosure relates to an article comprising an antibody or an antibody-binding fragment thereof of the foregoing or following paragraphs and a surface which is a well, a nitrocellulose membrane, a test strip, a microbead or a microchip.

In some embodiments, the disclosure relates to a method of detecting DbpA antigen in a biological sample, comprising contacting the sample with an antibody or an antigen-binding fragment thereof of the foregoing or following paragraphs and detecting a complex formed between the DbpA antigen and the antibody.

In some embodiments, the disclosure relates to a method of treating a Lyme disease caused by *Borrelia* species, e.g., *Borrelia burgdorferi*, especially *Borrelia burgdorferi* sensu lato (s.l.) in a subject in need thereof, comprising contacting the subject's biological sample with an effective amount of a composition comprising an antibody or an antigen binding fragment thereof of the foregoing or following paragraphs and a carrier.

In some embodiments, the disclosure relates to a method of treating a Lyme disease caused by *Borrelia* species, e.g., *Borrelia burgdorferi*, especially *Borrelia burgdorferi* sensu lato (s.l.), in a subject in need thereof, comprising administering into the subject, an effective amount of pharmaceutical composition comprising an antibody or an antigen binding fragment thereof of the foregoing or following paragraphs and a pharmaceutically acceptable carrier.

In some embodiments, the disclosure relates to an antibody or an antigen-binding fragment thereof or a pharmaceutical composition thereof comprising the antibody and a carrier, as provided above, for use in diagnosing a Lyme disease in a subject.

In some embodiments, the disclosure relates to an antibody or an antigen-binding fragment thereof or a pharmaceutical composition thereof comprising the antibody or the antigen-binding fragment and a pharmaceutically acceptable carrier for use in treating a Lyme disease in a subject.

In some embodiments, the disclosure relates to a method of making the antibody or an antigen-binding fragment thereof of the foregoing or following paragraphs, comprising immunizing an animal with a polypeptide comprising at least 80%, at least 90%, at least 95% or at least 99% sequence identity to a polypeptide comprising, consisting essentially of, or consisting of the amino acid sequence set forth in SEQ ID NO: 77, or an immunogenic fragment thereof; and obtaining the antibody from the blood or sera of the animal; and optionally digesting the antibody with pepsin to obtain an F(ab')2 fragment and/or with papain to obtain two Fab fragments.

In some embodiments, the disclosure relates to a method of making the antibody or an antigen-binding fragment thereof of the foregoing or following paragraphs, comprising culturing a hybridoma which comprises a nucleic acid encoding the antibody or the antigen-binding fragment thereof under conditions sufficient for the synthesis of the antibody; and obtaining the antibody from the culture.

In some embodiments, the disclosure relates to a method of making the antibody or an antigen-binding fragment thereof of the foregoing or following paragraphs, comprising culturing a hybridoma comprising plasmacytoma cells with antibody-producing B cells harvested from immunized mice.

In some embodiments, the disclosure relates to a method of making the antibody or an antigen-binding fragment thereof of the foregoing or following paragraphs, comprising chemical synthesis of the polypeptide sequences which make up the antibody or the antigen-binding fragment.

In some embodiments, the disclosure relates to use of an antibody or an antigen-binding fragment thereof or a pharmaceutical composition thereof of the foregoing or following paragraphs, for the manufacture of a medicament for diagnosing a Lyme disease in a subject.

In some embodiments, the disclosure relates to use of an antibody or an antigen-binding fragment thereof or a pharmaceutical composition thereof of the foregoing or following paragraphs, for the manufacture of a medicament for treating a Lyme disease caused by *Borrelia* species, e.g., *Borrelia burgdorferi*, especially *Borrelia burgdorferi* sensu lato (s.l.).

In some embodiments, the disclosure relates to a polypeptide comprising at least 80%, at least 90%, at least 95% or at least 99% sequence identity to a polypeptide comprising, consisting essentially of, or consisting of the amino acid sequence set forth in SEQ ID NO: 77, or an immunogenic fragment thereof.

In some embodiments, the disclosure relates to a fusion protein comprising a polypeptide comprising at least 80%, at least 90%, at least 95% or at least 99% sequence identity to a polypeptide comprising, consisting essentially of, or consisting of the amino acid sequence set forth in SEQ ID NO: 77 and a heterologous protein. Preferably, the heterologous protein comprises keyhole limpet hemocyanin (KLH).

In some embodiments, the disclosure relates to a composition comprising a polypeptide comprising at least 80%, at least 90%, at least 95% or at least 99% sequence identity to a polypeptide comprising, consisting essentially of, or consisting of the amino acid sequence set forth in SEQ ID NO: 77 and a carrier.

In some embodiments, the disclosure relates to a kit comprising, in one or separate packages, a polypeptide comprising at least 80%, at least 90%, at least 95% or at least 99% sequence identity to a polypeptide comprising, consisting essentially of, or consisting of the amino acid sequence set forth in SEQ ID NO: 77 and a carrier, optionally together with instructions for using the kit.

In some embodiments, the disclosure relates to a support comprising a polypeptide comprising at least 80%, at least 90%, at least 95% or at least 99% sequence identity to a polypeptide comprising, consisting essentially of, or consisting of the amino acid sequence set forth in SEQ ID NO: 77 and moiety for anchoring the polypeptide to the support. Preferably, the anchoring moiety comprises biotin-streptavidin or biotin-avidin complex.

In some embodiments, the disclosure relates to a method of generating antibodies which bind specifically to *Borrelia burgdorferi* DbpA, comprising immunizing a host with a polypeptide comprising at least 80%, at least 90%, at least 95% or at least 99% sequence identity to a polypeptide comprising, consisting essentially of, or consisting of the amino acid sequence set forth in SEQ ID NO: 77; obtaining the antibodies generated by the host; and optionally modifying the host-generated antibodies. Preferably, the modification comprises pepsin digestion or papain digestion or digestion with both pepsin and papain; and optionally comprising tagging a label (e.g., detectable label) to the antibody or the antigen-binding fragment.

In some embodiments, the disclosure relates to a nucleic acid encoding an antibody or an antigen-binding fragment thereof of the foregoing or following paragraphs. In some embodiments, the disclosure relates to a vector comprising the nucleic acid.

In some embodiments, the disclosure relates to a composition or a vaccine comprising a nucleic acid encoding an antibody or an antigen-binding fragment thereof of the foregoing or following paragraphs and a carrier.

In some embodiments, the disclosure relates to a host cell comprising a nucleic acid or a vector comprising the nucleic acid encoding an antibody or an antigen-binding fragment thereof of the foregoing or following paragraphs. Preferably, the host cell is a mammalian host cell or an insect host cell.

In some embodiments, the disclosure relates to a method of generating the antibody, comprising culturing the host cell comprising the nucleic acid or the vector encoding an antibody or an antigen-binding fragment thereof of the foregoing or following paragraphs under conditions sufficient for the expression of the polypeptide and obtaining the antibody from the culture.

In some embodiments, the disclosure relates to a nucleic acid encoding an antigenic peptide of the foregoing or following paragraphs (e.g., SEQ ID NO: 77) or an immunogenic fragment thereof.

In some embodiments, the disclosure relates to a composition or a vaccine comprising a nucleic acid encoding an antigenic peptide of the foregoing or following paragraphs (e.g., SEQ ID NO: 77) or an immunogenic fragment thereof and a carrier.

In some embodiments, the disclosure relates to a composition or a vaccine comprising a vector comprising the nucleic acid encoding an antigenic peptide of the foregoing or following paragraphs (e.g., SEQ ID NO: 77) or an immunogenic fragment thereof.

In some embodiments, the disclosure relates to a host cell comprising a nucleic acid or a vector comprising a nucleic acid encoding an antigenic peptide of the foregoing or following paragraphs (e.g., SEQ ID NO: 77) or an immunogenic fragment thereof. Preferably, the host cell is a mammalian host cell or an insect host cell.

In some embodiments, the disclosure relates to a method of generating the antigen of the foregoing or following paragraphs (e.g., SEQ ID NO: 77) or an immunogenic fragment thereof, comprising culturing the host cell comprising a vector or a nucleic acid encoding the antigenic polypeptide (e.g., SEQ ID NO: 77) or a immunogenic fragment thereof under conditions sufficient for the expression of the polypeptide; and obtaining the antigen from the culture.

BRIEF DESCRIPTION OF THE DRAWINGS

The details of one or more embodiments of the disclosure are set forth in the accompanying drawings/tables and the description below. Other features, objects, and advantages of the disclosure will be apparent from the drawings/tables and detailed description, and from the claims.

FIGS. 1A-1B show electrophoretic resolution of 6G8 under reducing (FIG. 1A) and non-reducing (FIG. 1B) conditions; FIGS. 1C-1D show electrophoretic resolution of 8C10 under reducing (FIG. 1C) and non-reducing (FIG. 1D) conditions.

FIG. 2A shows HPLC SEC profile of 6G8. FIG. 2B shows HPLC SEC profile of 8C10.

FIG. 5A shows test results with 6G8. FIG. 5B shows test results with 8C10.

DETAILED DESCRIPTION

Figure 1A:
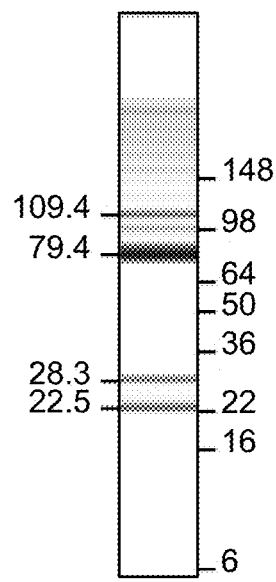
FIGS. 1A-1D show SDS-PAGE analysis of purification of various proteins by CAPTURESELECT IgM/HITRAP IgM column.
Figure 1B:
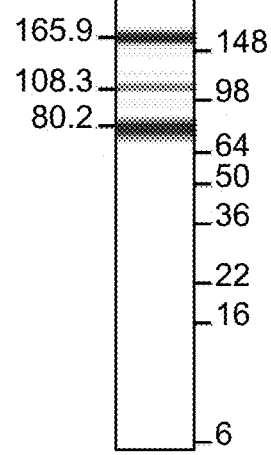
Figure 1C:
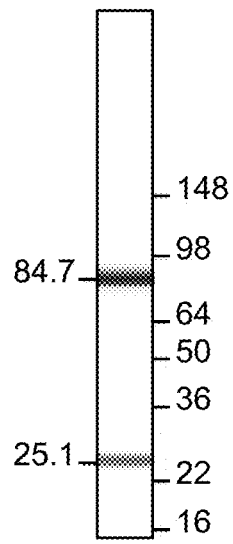
Figure 1D:
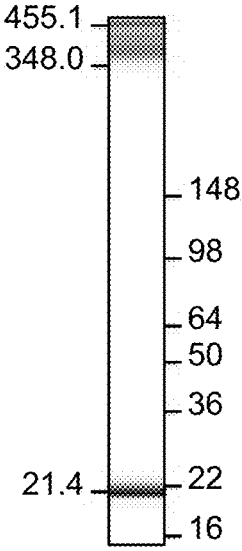
Figure 2A:
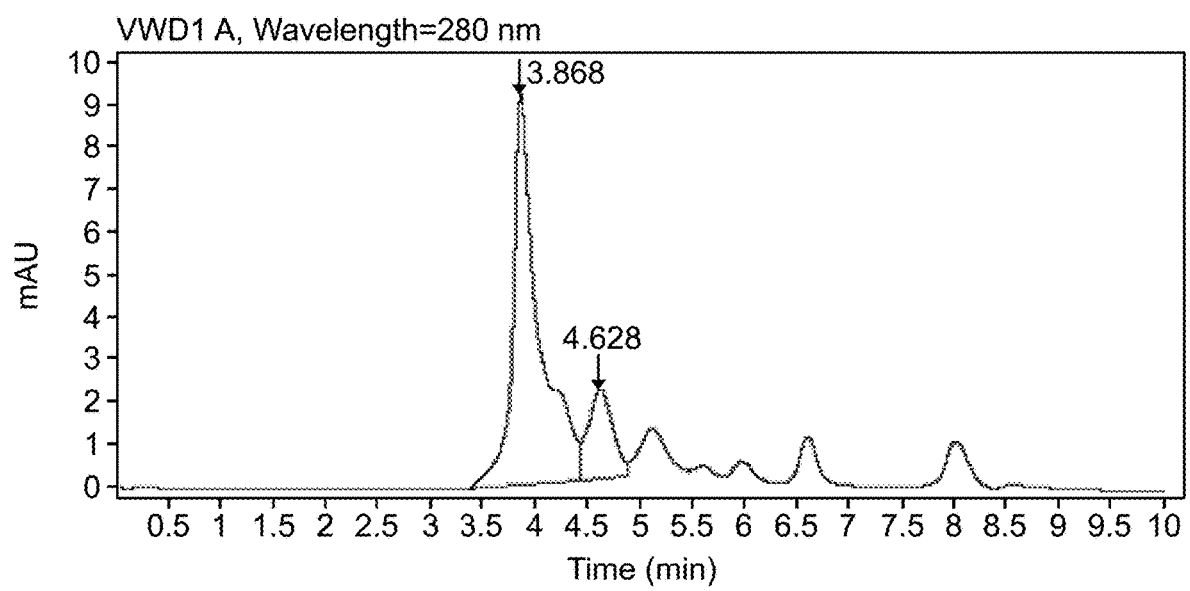
FIG. 2A and FIG. 2B show chromatographic profiles of purified chimeric proteins.
Figure 2B:
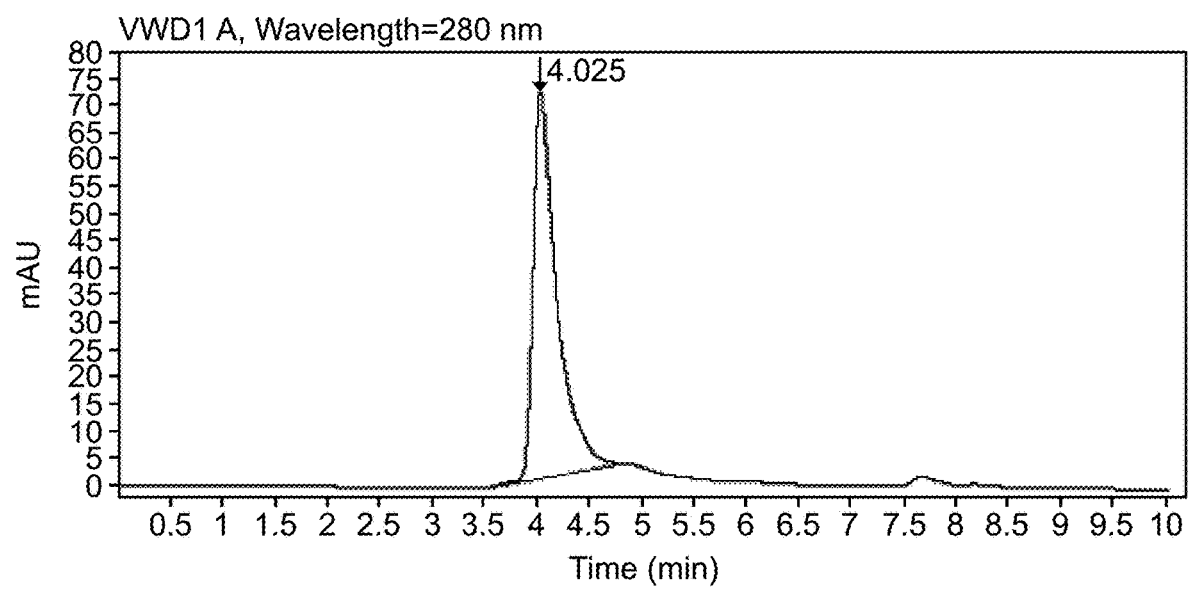
Figure 3:
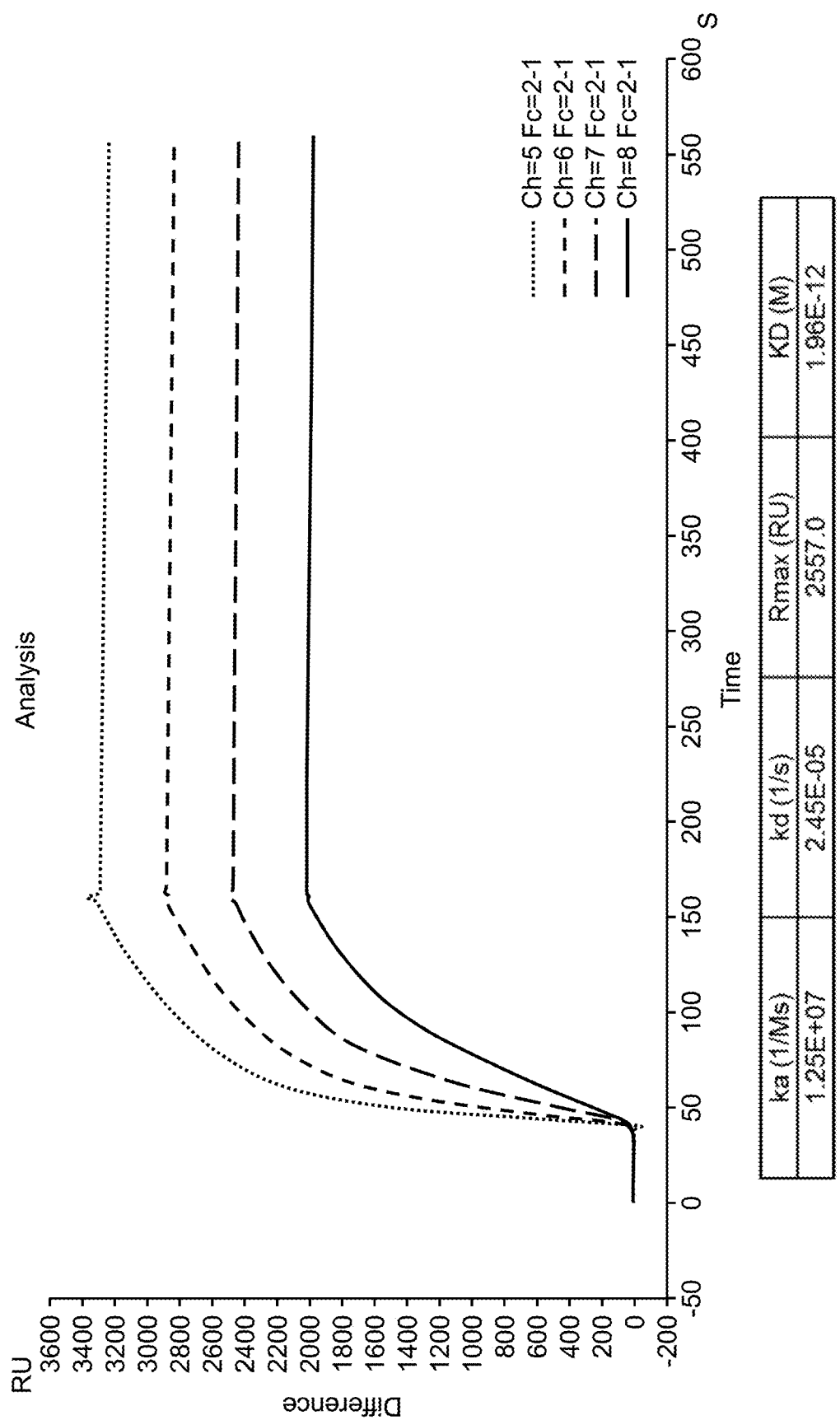
FIG. 3 shows the results of BIACORE testing of binding between 6G8 and CM5 chip-immobilized DbpA antigen. The binding assay was performed at 4 different concentrations of 6G8: 60 µg/ml, 30 µg/ml, 15 µg/ml, and 7.5 µg/ml.
Figure 4:
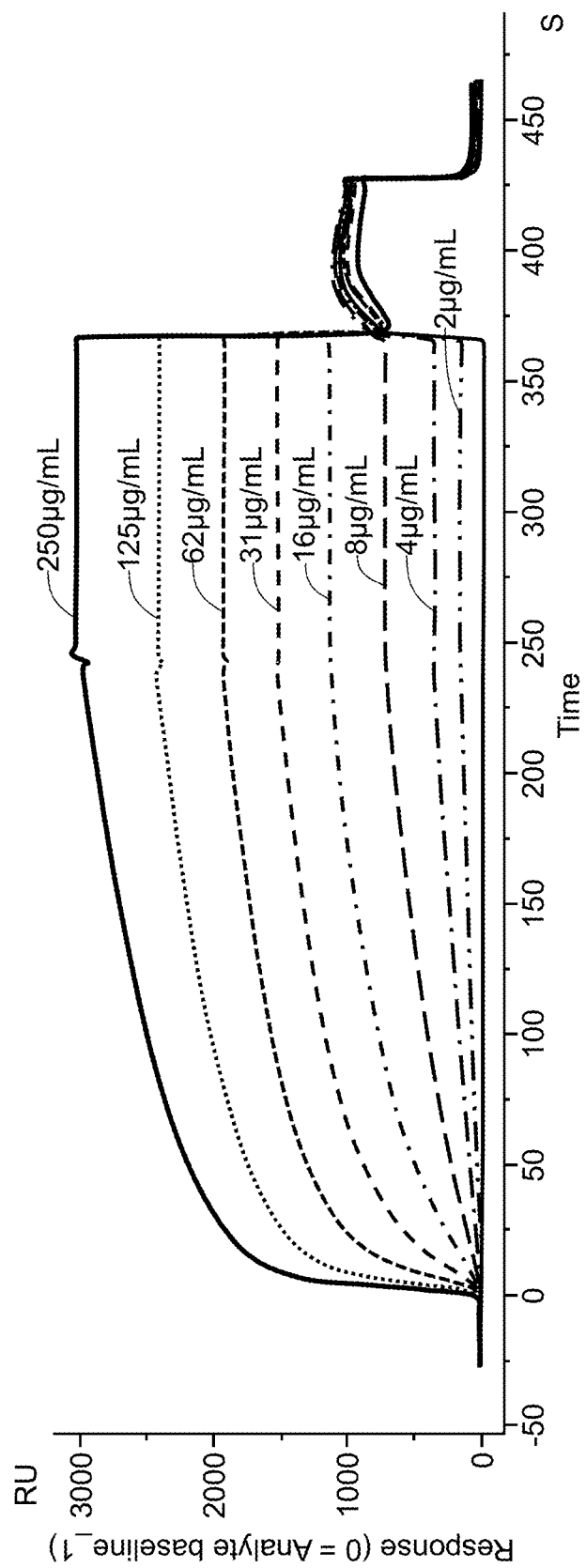
FIG. 4 shows the results of BIACORE testing of binding between 8C10 and CM5 chip-immobilized DbpA antigen. Assay was performed at 8 different concentrations of 8C10: 250 g/ml, 125 µg/ml, 62 µg/ml, 31 µg/ml, 16 µg/ml, 8 µg/ml, 4 µg/ml, and 2 µg/ml.
Figure 5A:
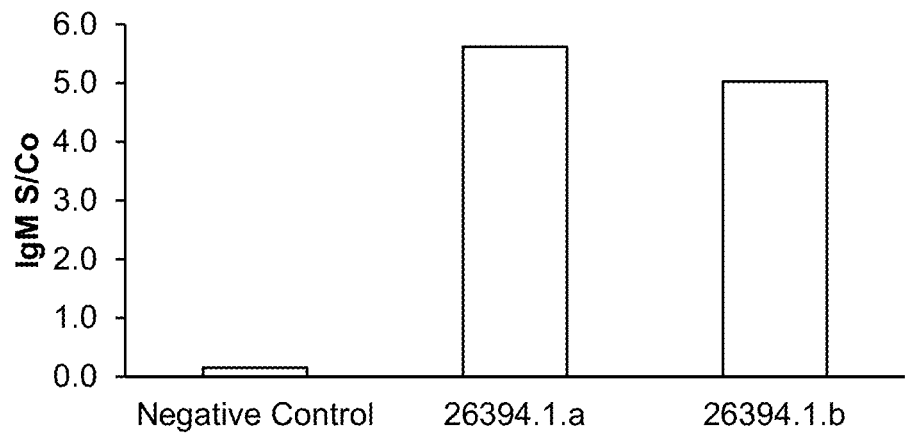
FIG. 5A and FIG. 5B show the results of immunoassay testing for IgM.
Figure 5B:
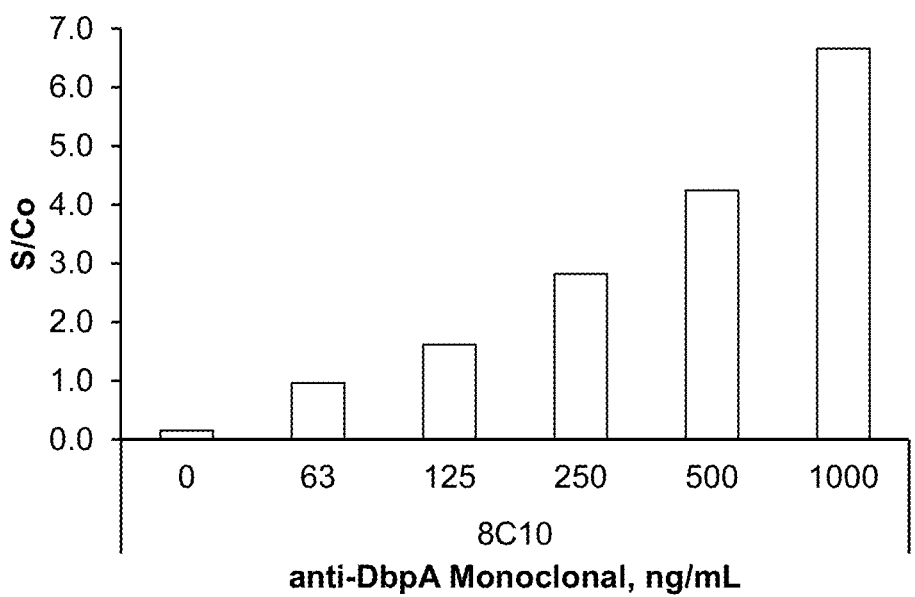
Figure 6:
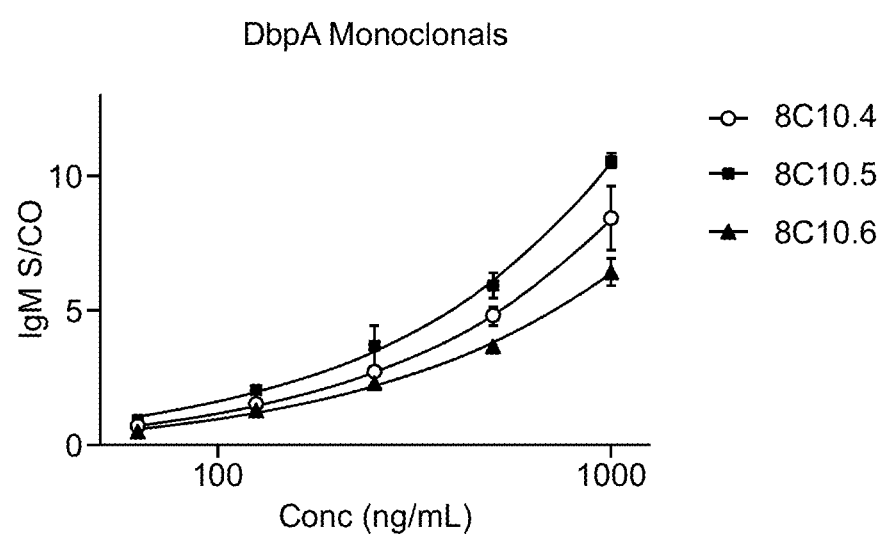
FIG. 6 show the results of testing of additional batches of DbpA_8C10 (lots 4, 5, and 6).

The present disclosure will now be described in more detail with reference to the accompanying drawings, in which preferred embodiments of the disclosure are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

Unless otherwise defined, scientific and technical terms used in connection with the present teachings described herein shall have the meanings that are commonly understood by those of ordinary skill in the art. The terminology used in the description of the disclosure herein is for the purpose of describing particular embodiments only and is not intended to be limiting of the disclosure. Further, unless otherwise required by context, singular terms shall include pluralities and plural terms shall include the singular. Generally, nomenclatures utilized in connection with, and techniques of molecular biology, and protein and oligo- or polynucleotide chemistry and hybridization described herein are those well-known and commonly-used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (4$^{th}$ ed., CSH Press, Cold Spring Harbor, N.Y. (2012); Ausubel, et al., Ed., Current Protocols in Molecular Biology, John Wiley & Sons, Inc., New York, N.Y. (2002); Harlow and Lane, antibodies, a Laboratory Manual, Cold Spring Harbor, EA Greenfield, Eds., CSH Press, Cold Spring Harbor, N.Y. (2014); Colligan, et al., eds., Current Protocols in Immunology, John Wiley & Sons, Inc., New York, N.Y. (2011); Colligan et al., Current Protocols in Protein Science, John Wiley & Sons, Hoboken, N.J. (2003).

The nomenclatures utilized in connection with, and the laboratory procedures and techniques described herein are those well-known and commonly-used in the art. For instance, when structurally characterizing peptides, amino acids are written in their single letter code, the integers denote the position of the amino acid in the referenced sequence, while the +1 or − before the integers refer to the positioning of the amino acid relative to the N-terminus of the mature polypeptide chain, wherein a "−" denotes that the amino acid is precedes (e.g., before) the N-terminal amino acid and a "+" denotes that the amino acid is follows (e.g., after) the N-terminal amino acid.

Definitions

As used in the description of the disclosure and the appended claims, the singular forms "a," "an," and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or"). For instance, the term "A and/or B" includes A, B, and (A and B).

Where a range of values is provided in this disclosure, it is intended that each intervening value between the upper and lower limit of that range and any other stated or intervening value in that stated range is encompassed within the disclosure. For example, if a range of 1 µM to 8 µM is stated, it is intended that 2 µM, 3 µM, 4 µM, 5 µM, 6 µM, and 7 µM are also explicitly disclosed.

The word "about" means a range of plus or minus 10% of that value, e.g., "about 5" means 4.5 to 5.5, "about 100" means 90 to 100, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within 10%, or within 5% or less, e.g., with 2%.

The term "substantially purified," as used herein, refers to nucleic acids, amino acids or antibodies that are removed from their natural environment and are isolated or separated, and are at least about 60% free, preferably about 75% free, most preferably about 90%, especially about 95% free and particularly about 99% free from other components with which they are naturally associated.

As used herein, the term "set" means one or more, e.g., at least 1, at least 2, at least 3, at least 4, at least 5, at least 6, or more than 6.

As used herein, the term "plurality" can be 2, 3, 4, 5, 6, 7, 8, 9, 10, or more.

As used herein, the term "synthetic" refers to a molecule, e.g., a polypeptide or a polynucleotide, which has been manufactured by artificial chemical synthesis or biosynthesis (e.g., genetic engineering-based production). Preferably, the term relates to non-naturally-occurring molecules constructed by one of the methods mentioned above or by other suitable methods known in the art.

As used herein, "isolated" means a nucleic acid sequence or a polypeptide sequence that is separated from the wild or native sequence in which it naturally occurs or is in an environment different from that in which the sequence naturally occurs.

As used herein, the term "peptide" includes synthetic or natural peptides comprising a linear chain or branched chain of amino acids, peptidomimetics, as well as pharmaceutically acceptable salts thereof. A peptide comprises a plurality of amino acid residues, e.g., 2, 3, 4, 5, 6, 7, 8, 9, 10, 11 or more, e.g., 200 amino acid residues (particularly about 2-60 amino acid residues; especially about 2-30 amino acid residues) which are bonded to each other via covalent bonds, e.g., a peptide bond. The term "protein" is often used in reference to relatively large polypeptides, and "peptide" is often used in reference to small polypeptides, usage of these terms in the art overlaps and varies. Thus, for simplicity, the term "polypeptide" will be used herein, although in some cases, the art may refer to the same polymer as a "protein." Unless otherwise indicated, the sequence for a polypeptide is given in the order from the amino terminus to the carboxyl terminus. Typically a peptide contains an amino ($NH_2$) terminus (free or modified) and a carboxy (COOH) terminus (free or modified); the directionality of the polypeptide chain flowing from the amino ($NH_2$) group to the carboxyl (COOH) group.

As used herein, the term "amino acid" includes the 22 amino acids that are proteinogenic amino acids and non-proteinogenic amino acids. The term "proteinogenic amino acid," is used in the field of biochemistry to refer to the 22 amino acids that are incorporated into eukaryotic and/or prokaryotic proteins during translation, such as: (a) histidine (His; H); (b) isoleucine (Ile; I); (c) leucine (Leu; L); (d) Lysine (Lys; K); (e) methionine (Met; M); (f) phenylalanine (Phe; F); (g) threonine (Thr; T); (h) tryptophan (Trp; W); (i) valine (Val; V); (j) arginine (Arg; R); (k) cysteine (Cys; C); (l) glutamine (Gln; Q); (m) glycine (Gly; G); (n) proline (Pro; P); (o) serine (Ser; S); (p) tyrosine (Tyr; Y); (q) alanine (Ala; A); (r) asparagine (Asn; N); (s) aspartic acid (Asp; D); (t) glutamic acid (Glu; E); (u) selenocysteine (Sec; U); (v) pyrrolysine (Pyl; O). The term "non-proteinogenic amino acid" is used in the field of biochemistry to refer to naturally occurring and non-naturally occurring amino acids that are not proteinogenic amino acids, such as (1) citrulline (Cit); (2) cystine; (3) gama-amino butyric acid (GABA); (4) ornithine (Orn); (5) theanine; (6) homocysteine (Hcy); (7) thyroxine (Thx); and amino acid derivatives such as betaine; carnitine; carnosine creatine; hydroxytryptophan; hydroxyproline (Hyp); N-acetyl cysteine; S-Adenosyl methionine (SAM-e); taurine; tyramine, D-amino acids such as D-alanine (D-Ala); Norleucine (Nle); 4-hydroxyproline (HYP); 3,4-dehydro-L-proline (DHP); aminoheptanoic acid (AHP); (2R,5S)-5-phenyl-pyrrolidine-2-carboxylic acid (2PP); L-a-methylserine (MS); N-methylvaline (MV); 6-aminohexanoic acid (6-AHP); and 7-aminoheptanoic acid (7-AHP). Abbreviations for amino acid residues are used in keeping with standard polypeptide nomenclature delineated in IUPAC-IUB Biochemical Nomenclature, *J. Biol. Chem.* 241: 527, 1966.

As used herein, "amino acid residue" means the individual amino acid units incorporated into a polypeptide. Amino acid residues are generally preferred to be in the "L" isomeric form. However, residues in the "D" isomeric form can be substituted for any L-amino acid residue, as long as the desired functional property (e.g., antibody binding) is retained by the polypeptide. It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "domain" as used herein, is a portion of a protein that has a tertiary structure. The domain may be connected to other domains in the complete protein by short flexible regions of polypeptide. Alternatively, the domain may represent a functional portion. For instance, an immunoglobulin molecule contains heavy and light chains, each chain containing a series of similar, although not identical, amino acid sequences. Each of these repeats corresponds to a discrete, compactly folded region of protein structure known as a protein domain. The light chain is made up of two such immunoglobulin domains, whereas the heavy chain of the IgG antibody contains four. Moreover, the amino-terminal sequences of both the heavy and light chains vary greatly between different antibodies and the remaining domains are constant between immunoglobulin chains of the same isotype. The amino-terminal variable domains (V) of the heavy and light chains (VH and VL, respectively) confer on it the ability to bind specific antigen, while the constant domains (C domains) of the heavy and light chains (CH and CL, respectively) make up the C region. The multiple heavy-chain C domains are numbered from the amino-terminal end to the carboxy terminus, for example CH1, CH2, CH3, and so on.

A "conservative" amino acid substitution, as used herein, generally refer to substitution of one amino acid residue with another amino acid residue from within a recognized group which typically changes the structure of the peptide by biological activity of the peptide is substantially retained. Conservatively substituted amino acids can be identified using a variety of well know methods, such as a blocks substitution matrix (BLOSUM), e.g., BLOSUM62 matrix. BLOSUM is a substitution matrix used for sequence alignment of proteins, wherein an alignment score is used to map out relationship between evolutionarily divergent protein sequences. They are based on local alignments. For instance, a BLOSUM62 substitution matrix can be found in the world-wide-web URL NCBI(dot)NLM(dot)NIH(dot)GOV/class/fieldguide/BLOSUM62.txt, which is incorporated by reference.

As used herein, "substantially identical" in reference to an amino sequence or nucleotide sequence means that a candidate sequence is at least 80% sequence identical to the reference sequence over a given comparison window (e.g., 250 amino acids). Thus, substantially similar sequences include those having, for example, at least 85% sequence identity, at least 90%, 91%, 92%, 93%, 94%, 95%, 96%, 97%, 98%, or 99%, or greater, e.g., 99.5%, sequence identity. Two sequences that are identical to each other are also substantially similar. The comparison window or the length of comparison sequence will generally be at least the length of antibody binding fragment of the candidate. Sequence identity is calculated based on the reference sequence, and algorithms for sequence analysis are known in the art. Thus, to determine percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The percent sequence identity between the two sequences is a function of the number of identical positions shared by the sequences (i.e., percent sequence identity=numbers of identical positions/total numbers of positions×100). Percent sequence identity between two polypeptide sequences can be determined using the Vector NTI software package (Invitrogen Corp., Carlsbad, Calif.). A gap opening penalty of 10 and a gap extension penalty of 0.1 are used for determining the percent identity of two polypeptides. All other parameters are set at the default.

As used herein, the term "derivative" includes salts, amides, esters, enol ethers, enol esters, acetals, ketals, acids, bases, solvates, hydrates, polymorphs or prodrugs of the individual amino acids, antigenic peptides or antibodies (or their antigen-binding fragments). Derivatives may be readily prepared by those of skill in this art using known methods for such derivatization. The derivatives suitable for use in the methods described herein may be administered to animals or humans without substantial toxic effects and either are biologically active or are prodrugs. Derivatives include solvent addition forms, e.g., a solvate or alcoholate. Derivatives further include amides or esters of the amino acids and/or isomers (e.g., tautomers or stereoisomers).

As used herein, the term "salt" includes salts derived from any suitable of organic and inorganic counter ions well known in the art and include, by way of example, hydrochloric acid salt or a hydrobromic acid salt or an alkaline or an acidic salt of the amino acids or peptides.

As used herein, the term "solvate" refers to compounds containing either stoichiometric or non-stoichiometric amounts of a solvent, and may be formed during the process of crystallization with acceptable solvents such as water, ethanol, and the like. "Hydrates" are formed when the solvent is water; alcoholates are formed when the solvent is alcohol. Solvates of compounds described herein can be conveniently prepared or formed using routine techniques. "Polymorphs" refer to alternate crystal forms of the compounds described herein. Polymorphic purity of drug samples can be checked using techniques such as powder X-ray diffraction, IR/Raman spectroscopy, and utilizing the differences in their optical properties in some cases (Thomas et al., *Chemical Communications*, 48: 10559-10561 (2012)).

As used herein, "amino acid analogs" are compounds that are structurally or chemically similar to an amino acid. Many suitable amino acid analogs are known in the art, and representative examples include, e.g., p-Acetylphenylalanine, m-Acetylphenylalanine, 0-allyltyrosine, Phenylselenocysteine, p-Propargyloxyphenylalanine, p-Azidophenylalanine, p-Boronophenylalanine, O-methyltyrosine, p-Aminophenylalanine, p-Cyanophenylalanine, m-Cyanophenylalanine, p-Fluorophenylalanine, p-Iodophenylalanine, p-Bromophenylalanine, p-Nitrophenylalanine, L-DOPA, 3-Aminotyrosine, 3-Iodotyrosine, p-Isopropylphenylalanine, 3-(2-Naphthyl)alanine, biphenylalanine, homoglutamine, D-tyrosine, p-Hydroxyphenyllactic acid, 2-Aminocaprylic acid, bipyridylalanine, HQ-alanine, p-Benzoylphenylalanine, o-Nitrobenzylcysteine, o-Nitrobenzylserine, 4,5-Dimethoxy-2-Nitrobenzylserine, o-Nitrobenzyllysine, o-Nitrobenzyltyrosine, 2-Nitrophenylalanine, dansylalanine, p-Carboxymethylphenylalanine, 3-Nitrotyrosine, sulfotyrosine, acetyllysine, methylhistidine, 2-Aminononanoic acid, 2-Aminodecanoic acid, pyrrolysine, Cbz-lysine, Boc-lysine, allyloxycarbonyllysine, arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. The term includes modified or unusual amino acids e.g., D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, -phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid; functionalized amino acids, e.g., alkyne-functionalized, azide-functionalized, ketone-functionalized, aminooxy-functionalized amino acids and the like. See Liu et al., *Ann. Rev. Biochem.* 79:413, 2010; Kim et al., *Curr. Opin. Chem. Biol.*, 17:412, 2013.

As used herein, the term "peptoid" refers to a polypeptide containing one or more N-substituted glycine residues. An N-substituted amino acid residue has a standard amino acid side-chain pendant from the N, rather than from the a-carbon. Representative examples of peptoids are provided in, e.g., U.S. Pat. Nos. 6,075,121 and 6,887,845.

As used herein, the term "variant" in the context of a polypeptide refers an amino acid sequence in which one or more amino acids are added and/or substituted and/or deleted and/or inserted in the sequences of the DbpA antigen or the antibody that binds thereto.

As used herein, a "consensus" amino acid is an amino acid chosen to occupy a given position in the consensus polypeptide obtained by this method. A system which is organized to select consensus amino acids as described above may be a computer program, or a combination of one or more computer programs with "by hand" analysis and calculation. A set of amino acid sequences existing within the group of amino acid sequences from which the consensus sequence is prepared means a set of such sequences which are more similar to each other than to other members of the group, based on the evolutionary similarity analysis performed above. An example of such a group is a species where a set with in the group would be members of a particular polypeptide, e.g., antigenic regions.

As used herein, the term "fusion protein" refers to a peptide or a functional fragment thereof, that is bonded through a bond, e.g., a peptide bond (or amide bond), to an amino acid sequence that is not bonded naturally in the parent peptide. Illustrative fusion polypeptides include fusions of an antigenic peptide of the disclosure (or a functional fragment thereof) to a heterologous protein or polypeptide, e.g., a polypeptide comprising all or a portion of a protein which is not *B. burgdorferi* DbpA.

The terms "polynucleotide" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other nonnucleotidic backbones, for example, polyamide (e.g., peptide nucleic acids (PNAs)) and polymorpholino polymers (commercially available from the Anti-Virals, Inc., Corvallis, Oreg., USA, as NEUGENE), and other synthetic sequence-specific nucleic acid polymers provided that the polymers contain nucleobases in a configuration which allows for base pairing and base stacking, such as is found in DNA and RNA. There is no intended distinction in length between the terms "polynucleotide" and "nucleic acid molecule."

As used herein, the term "nucleotide" refers to molecules that, when joined, make up the individual structural units of the nucleic acids RNA and DNA. A nucleotide is composed of a nucleobase (nitrogenous base), a five-carbon sugar (either ribose or 2-deoxyribose), and one phosphate group. "Nucleic acids" as used herein are polymeric macromolecules made from nucleotide monomers. In DNA, the purine bases are adenine (A) and guanine (G), while the pyrimidines are thymine (T) and cytosine (C). RNA uses uracil (U) in place of thymine (T).

As used herein, a "nucleic acid," "polynucleotide," or "oligonucleotide" can be a polymeric form of nucleotides of any length, can be DNA or RNA, and can be single- or double-stranded. Nucleic acids can include promoters or other regulatory sequences. Oligonucleotides can be prepared by synthetic means. Nucleic acids include segments of DNA, or their complements spanning or flanking any one of the polymorphic sites. The segments can be between 5 and 1000 contiguous bases and can range from a lower limit of 5, 20, 50, 100, 200, 300, 500, 700 or 1000 nucleotides to an upper limit of 500, 1000, 2000, 5000, or 10000 nucleotides (where the upper limit is greater than the lower limit). Nucleic acids between 5-20, 50-100, 50-200, 100-200, 120-300, 150-300, 100-500, 200-500, or 200-1000 bases are common. A reference to the sequence of one strand of a double-stranded nucleic acid defines the complementary sequence and except where otherwise clear from context, a reference to one strand of a nucleic acid also refers to its complement. Complementation can occur in any manner, e.g., DNA=DNA; DNA=RNA; RNA=DNA; RNA=RNA, wherein, in each case, the "=" indicates complementation. Complementation can occur between two strands or a single strand of the same or different molecule.

The term "complementary" means that a hydrogen bond is formed between bases constituting sequences and specifically means that adenine is paired with thymine; thymine is paired with adenine; guanine is paired with cytosine; and cytosine is paired with guanine. In the present specification, the term "complementarity" means the ratio of complementary base pairs between sequences to be compared. All the numeric values of "complementarity" shown in the present specification need only to be numeric values calculated as homology between the complementary strands of one nucleotide sequence and another nucleotide sequence using a homology search program generally known by those skilled in the art. These numeric values of complementarity can be calculated easily using default (initial setting) parameters in, for example, FASTA or BLAST. Methods for generating polynucleotides that are complementary to a template nucleic acid sequence are known in the art. See, e.g., using the "Reverse Complement" program available via The Sequence Manipulation Suite at Bioinformatics(dot) Org.

As used herein, the term "RNA equivalent" of nucleic acids include variants of a template DNA sequence containing at least one, if not all, bases and/or sugars commonly found in RNA molecules. Methods for generating RNA equivalents of template DNA sequences are known in the art, e.g., sequence editor tools available via the Health Sciences Library System at the University of Pittsburgh.

As used herein, the term "sequence" as a noun refers to the actual nucleotide sequence obtained from sequencing; for example, DNA having the sequence AGTCC. The term "sequencing" or "sequence" as a verb refers to a process whereby the nucleotide sequence of a polynucleotide, e.g., DNA, or order of nucleotides, is determined, such as a nucleotide order AGTCC, etc.

As used herein, the term "variation" refers to a change or deviation. In reference to nucleic acid, a variation refers to a difference(s) or a change(s) between DNA nucleotide sequences, including differences in bases. This actual difference in nucleotides between DNA sequences may be a single nucleotide polymorphism (SNP), and/or a change in a DNA sequence, e.g., fusion, deletion, addition, repeats, etc., observed when a sequence is compared to a reference, such as, e.g., a *B. burgdorferi* DbpA sequence of SEQ ID NO: 78 or an immunogenic fragment thereof.

As used herein, the term "hybridization" refers to any process by which a strand of nucleic acid bonds with a complementary strand through base pairing. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature. Variations on the above ranges and conditions are well known in the art.

The term "hybridization complex" as used herein, refers to a complex formed between two nucleic acid sequences by virtue of the formation of hydrogen bonds between complementary bases. A hybridization complex may be formed in solution or formed between one nucleic acid sequence present in solution and another nucleic acid sequence immobilized on a solid support (e.g., paper, plastic, membranes, filters, chips, or any other appropriate substrate).

As used herein, nucleic acid derivatives include, e.g., methylphosphonates, phosphotriesters, phosphorothioates, phosphoramidates and the like. Nucleic acid derivatives may contain modification of the sugar, base, or phosphate portion of a nucleotide. For instance, oligonucleotides may be derivatized at the bases, the sugars, the ends of the chains, or at the phosphate groups of the backbone to promote in vivo stability. CpG sequences may be derivatized to minimize degradation; derivatization may be alkylation, and is preferably methylation. Modifications of the phosphate groups are preferred in one embodiment of the disclosure since phosphate linkages are sensitive to nuclease activity. Preferred derivatives are the methylphosphonates, phosphotriesters, phosphorothioates, and phosphoramidates. Derivatives may also contain alternating phosphorothioate and unmodified linkages, or alternating methylphosphonate and unmodified linkages, or alternating phosphorothioate and methylphosphonate linkages. Additionally, the phosphate linkages may be completely substituted with non-phosphate linkages such as amide linkages. Appendages to the ends of the oligonucleotide chains also provide exonuclease resistance. The 5' or 3' end may be derivatized or "capped" with a phosphoramidate linkage, an inverted nucleotide conjugated to the oligonucleotide via a 3'-3' linkage, an aminoacridine residue, or poly-L-lysine.

As used herein, nucleic acid "analog" includes oligonucleotides having residues or linkers synthetically introduced therein, such as a ribonucleic acid residue within a DNA sequence, a branching linking agent such as a glycerol derivative, or an aminoalkyl linker, for example. Nucelic acid "adduct" includes, for example, O6-alkyl-dG and O6-Me-dG. As used herein, the term nucleic acid "conjugate" refers to a molecule covalently or non-covalently bound to one or more polynucleotides, e.g., a linear, branched, or dendritic polynucleotide covalently or non-covalently bound to a fluorescent dye molecule.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay.

As used herein, the term "operably linked" refer to functionally related nucleic acid sequences. A promoter is operably linked with a coding sequence if the promoter controls the transcription of the encoded polypeptide. While operably linked nucleic acid sequences can be contiguous and in reading frame, certain elements, e.g., repressor genes, may not be contiguously linked but still bind to operator sequences that control expression of the polypeptide product.

As used herein, the term "vector" refers to a molecule that is capable of transferring nucleic acid sequences to target cells (e.g., viral vectors, non-viral vectors, particulate carriers, and liposomes). Typically, "vector construct" means any nucleic acid construct capable of directing the expression of a nucleic acid of interest and which can transfer nucleic acid sequences to target cells. Thus, the term includes cloning, expression, and viral vectors.

As used herein, the term "reporter" refers to molecule, e.g., a DNA, RNA, and/or polypeptide sequence, that is detectable in any detection system, including, but not limited to enzyme (e.g., ELISA, as well as other histochemical assays), fluorescent, and luminescent systems. Exemplary reporters include, e.g., β-glucuronidase, green fluorescent protein (GFP), $E.$ $coli$ β-galactosidase (LacZ), $Halobacterium$ β-galactosidase, $Neuropsora$ tyrosinase, human placental alkaline phosphatase, and chloramphenicol acetyl transferase (CAT), $Aequorin$ (jellyfish bioluminescence), Firefly luciferase (EC 1.13.12.7) form $Photinus$ $pyralis,$ $Renilla$ luciferase (EC 1.13.12.5) from the sea pansy $Renilla$ $reniformis,$ and Bacterial luciferase (EC 1.14.14.3) from $Photobacterium$ $fischeri.$ Preferably, the reporter comprises a luciferin-luciferase system. As used herein, the term "luciferin-luciferase system" refers to any process or method that allows the contact of luciferin and luciferase in the presence of a substrate (i.e., for example, cAMP) under conditions such that the resulting luminescence may be detected. Such a system may be comprised within a transfected host cell or provided in separate kit containers whereby the contents may be mixed together.

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present disclosure. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., $Science$ 242:423-426, 1988; Huston et al., $PNAS$ $USA,$ 85:5879-5883, 1988), including diabodies. Such single chain antibodies and diabodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik et al., $J$ $Mol$ $Biol.,$ 296(1):57-86, 2000).

As used herein, the term "diabody" refers a noncovalent dimer of single-chain Fv (scFv) fragment that consists of the heavy chain variable (VH) and light chain variable (VL) regions connected by a small peptide linker. Another form of diabody is single-chain (Fv)2 in which two scFv fragments are covalently linked to each other.

As used herein, the term "single domain antibody" or "sdAb" refers to a type of single chain antibody comprising a variable region (VH) of a heavy chain of a human antibody. SdAbs are antibody fragments consisting of a single monomeric variable antibody domain. They are derived, for example, from heavy chain antibodies derived from humans, which consist only of two antibody heavy chains, with no light chain. With a molecular weight of only 12-15 kDa, sdAbs are much smaller than monoclonal antibodies (mAbs), e.g., IgG antibodies (150-160 kDa), which have two heavy protein chains and two light chains. SdAbs may be derived from any species including, but not limited to mouse, human, camel, llama, goat, rabbit, bovine. The sdAb can be modified versions of a naturally occurring immunoglobulin known as heavy chain antibody devoid of light chains. Such immunoglobulins are disclosed in U.S. Pat. Nos. 8,293,233 and 9,371,371; and U.S. Pub. No. 2011-0052565. For clarity reasons, the variable domain derived from a heavy chain antibody naturally devoid of light chain is known herein as a VHor sdAb to distinguish it from the conventional VHof four chain immunoglobulins.

As used herein, the term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. The term "native conformational epitope" or "native protein epitope" are used interchangeably herein, and include protein epitopes resulting from conformational folding of the DbpA molecule which arise when amino acids from differing portions of the linear sequence of the DbpA molecule come together in close proximity in 3-dimensional space. Such conformational epitopes are distributed on the extracellular side of the plasma membrane.

As used herein, the term "paratope" or "an antigen-binding site" refers to the part of an antibody which recognizes and binds to an antigen. Generally, paratopes comprise 5 to 10 amino acids of the antibody's Fv region, part of the fragment antigen-binding region (Fab), and contains parts of the antibody's heavy and light chains.

As used herein, the term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the disclosure includes bispecific, trispecific, tetraspecific, and other multispecific molecules which are directed to cell surface antigens, such as DbpA, and to other targets, such as Fc receptors on effector cells.

As used herein, the term "bivalent" antibody refers to antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., PNAS USA, 90, 6444-8, 1993; Poljak et al., Structure, 2, 1121-23, 1994). "Multivalent" antibodies include two or more binding domains which may all be of the same specificity or may have multiple specificities.

As used herein, "chimeric antibodies" are those antibodies that retain distinct domains, usually the variable domain, from one species and the remainder from another species; e.g., mouse-human chimeras. The term "human antibody", as used herein, is intended to include antibodies having variable and constant regions derived from or closely matching human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo such as during the recombination of V, D, and J segments of the human heavy chain). Thus as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to those encoded by human germline antibody genes. Human antibodies have been classified into groupings based on their amino acid sequence similarities (Nikoloudis et al., Peer J., 2, e456, 2014; Adolf-Bryfogle et al., Nucleic Acids Res., 43, D432-8, 2015). Thus, using a sequence similarity search, an antibody with similar linear sequence can be chosen as a template to select or create human or humanized antibodies.

As used herein, "humanization" (also called reshaping or CDR-grafting) includes established techniques for reducing the immunogenicity of monoclonal antibodies (mAbs) from xenogeneic sources (commonly rodent) and for improving affinity or the effector functions (ADCC, complement activation, C1q binding). The engineered mAb can be produced using the techniques of molecular biology, using phage displayed randomized sequences, or synthesized de novo. For example, in order to humanize an antibody with incorporated the CDR regions from a nonhuman species, the design might include variations such as conservative amino acid substitutions in residues of the CDRs, and back substitution of residues from the nonhuman mAb into the human framework regions (back-mutations). The positions can be discerned or identified by sequence comparison methods, consensus sequence analysis, or structural analysis of the variable regions' 3D structure. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR (framework) residues can be selected and combined from the consensus and import sequences so that the desired antibody characteristic, such as increased affinity for the target antigen(s), is achieved. As the datasets of known parameters for antibody structures increases, so does the sophistication and refinement of these techniques. Another approach to humanization is to modify only surface residues of the rodent sequence with the most common residues found in human mAbs and has been termed "resurfacing" or "veneering." Known human Ig sequences are disclosed in, e.g., IGBLAST (NCBI); Kabat et al., Sequences of Proteins of Immunological Interest, DIANE Publishing, 1992. Humanization or engineering of antibodies of the present disclosure can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia et al., J. Mol. Biol., 196:901 (1987), Carter et al., PNAS USA, 89:4285 (1992); Presta et al., J. Immunol., 151:2623 (1993), U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; WO199900683; and WO994018219.

As used herein, the term "CDR" refers to the complementarity determining region or hypervariable region amino acid residues of an antibody which are responsible for antigen-binding. The hypervariable region or CDRs of the human IgG subtype of antibody typically comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al. (supra) and/or those residues from a hypervariable loop in the heavy chain variable domain as described by Chothia et al. (*J. Mol. Biol.* 196: 901-17, 1987). Framework or FR residues are those variable domain residues other than and bracketing the hypervariable regions.

As used herein, the term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

As used herein, the term "recombinant antibody" refers to antibodies that are prepared, expressed, created or isolated by recombinant means, such as (a) antibodies isolated from an animal or a hybridoma prepared therefrom (described further in Section I, below), (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences.

As used herein, the term "isolated antibody" refers to an antibody which is substantially free of other antibodies having different antigenic specificities (e.g., an isolated antibody that specifically binds to DbpA is substantially free of antibodies that specifically bind antigens other than DbpA). An isolated antibody that specifically binds to an epitope, isoform or variant of DbpA may, however, have cross-reactivity to other related antigens, e.g., from other species (e.g., DbpA species homologs). Moreover, an isolated antibody may be substantially free of other cellular material and/or chemicals. Especially, "isolated" monoclonal antibodies having different specificities are combined in a well-defined manner to formulate the composition.

As used herein, the term "high affinity" for an antibody refers to an antibody having a $K_D$ of $10^{-8}$ M or less, more preferably $10^{-9}$ M or less and even more preferably $10^{-10}$ M or less, e.g., $10^{-11}$ M or even $10^{-12}$ M. However, "high affinity" binding can vary for other antibody isotypes. For example, "high affinity" binding in the context of an IgM isotype may to an antibody having a $K_D$ of $10^{-7}$ M or less, more preferably $10^{-8}$ M or less, e.g., $10^{-9}$ M.

As used herein, the terms "dissociation constant," "$K_{dis}$" "$K_D$," "Kd" refer to the dissociation rate of a particular antibody-antigen interaction, which is typically a ratio of the rate of dissociation ($k_2$), also called the "off-rate ($k_{off}$)", to the rate of association rate ($k_1$) or "on-rate ($k_{on}$)". Thus, $K_D$ equals k2/k1 or $k_{off}/k_{on}$ and is expressed as a molar concentration (M). It follows that the smaller Kd, the stronger the binding. So $10^{-6}$ M (or 1 μM) indicates weak binding compared to $10^{-9}$ M (or 1 nM).

The terms "specifically binds" and "specific binding" when made in reference to the binding of two molecules, e.g., antibody and an antigen, refer to an interaction which is dependent upon the presence of a particular structure on the molecule(s). For example, if an antibody is specific for epitope "A" on the molecule, then the presence of a protein containing epitope A (or free, unlabeled A) in a reaction containing labeled "A" and the antibody will reduce the amount of labeled A bound to the antibody. In one embodiment, the level of binding of an antibody to a molecule is determined using the "$IC_{50}$" i.e., "half maximal inhibitory concentration" that refers to the concentration of a substance (e.g., inhibitor, antagonist, etc.) that produces a 50% inhibition of a given biological process, or a component of a process (e.g., binding between antigen-antibody and/or the resulting biological effect, e.g., symptoms of Lyme diseases). It is commonly used as a measure of an antagonist substance's potency. As used herein, "specific binding" in the context of an antibody-antigen interaction refers to binding with a dissociation constant ($K_D$) of about $10^{-7}$ M or less to the antigen (e.g., DbpA), preferably $10^{-8}$ M or less and even more preferably $10^{-9}$ M or less, e.g., $10^{-10}$ M or even $10^{-11}$ M. Additionally, the antibody may bind to the antigen with a $K_D$ that is at least about 3-fold, 4-fold, or 5-fold less than its $K_D$ for binding to a non-specific antigen (e.g., BSA, casein, or a random polypeptide having a sequence that is not present in the particular antigen (e.g., DbpA)).

As used herein "highly specific" binding means that the relative $K_D$ of the antibody for the specific target epitope is at least 10-fold, at least 20-fold, e.g., about 50-fold less than the $K_D$ for binding that antibody to other ligands (e.g., BSA, casein, or a random polypeptide).

As used herein, "isotype" refers to the antibody class (e.g., IgM or IgG) that is encoded by heavy chain constant region genes. Some antibody classes further encompass subclasses which are also encoded by the heavy chain constant regions and further decorated by oligosaccharides at specific residues within the constant region domains (e.g. IgG1, IgG2, IgG3 and IgG4) which further impart biological functions to the antibody.

As used herein, the term "capture antibody" refers to an antibody that is used to bind an antigen and thereby permit the recognition of the antigen by a subsequently applied antibody. For example, the capture antibody may be bound to a microtiter well and serve to bind an antigen of interest present in a sample added to the well. Another antibody (termed the "primary antibody") is then used to bind to the antigen-antibody complex, in effect to form a "sandwich" comprised of antibody-antigen-antibody complex. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of an antibody-antigen-antibody-antibody complex. Again, appropriate reporter reagents are then added to detect the labelled antibody. Any number of additional antibodies may be added as desired. These antibodies may also be labelled with a marker, including, e.g., an enzyme, fluorescent marker, or radioactivity.

The term "chimeric" as used herein, refers to any nucleic and/or amino acid sequence containing portions from two or more different species. A protein may be chimeric if the primary amino acid sequence contains portions from two or more different species (i.e., for example, an *B. burgdorferi* DbpA fused to *Renilla* luciferase). A protein may also be chimeric if the primary amino acids sequence contains portions from two or more different proteins, whether from the same species or different species. Further, a nucleic acid may be chimeric if the primary nucleotide sequence contains portions from two or more different species. A nucleic acid may also be chimeric if the primary nucleotide sequence contains portions from two or more different proteins, whether from the same species or different species. An antibody may be chimeric if regions/domains of the antibody molecule are derived from two different species, e.g., fusing the antigen binding region (variable domains of the heavy and light chains, VH and VL) from one species like a mouse, with the constant domain (effector region) from another species such as a rabbit. Humanized antibodies, which are antibodies from non-human species whose protein sequences have been modified to increase their similarity to antibody variants produced naturally in humans, may be chimeric antibodies.

As used herein, the term "hybridoma" refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "pharmaceutically acceptable" means a molecule or a material that is not biologically or otherwise undesirable, i.e., the molecule or the material can be administered to a subject without causing any undesirable biological effects such as toxicity.

As used herein, the term "carrier" denotes buffers, adjuvants, dispersing agents, diluents, and the like. For instance, the peptides or compounds of the disclosure can be formulated for administration in a pharmaceutical carrier in accordance with known techniques. See, e.g., Remington, The Science & Practice of Pharmacy ($9^{th}$ Ed., 1995). In the manufacture of a pharmaceutical formulation according to the disclosure, the peptide or the compound (including the physiologically acceptable salts thereof) is typically admixed with, inter alia, an acceptable carrier. The carrier can be a solid or a liquid, or both, and is preferably formulated with the peptide or the compound as a unit-dose formulation, for example, a tablet, which can contain from about 0.01 or 0.5% to about 95% or 99%, particularly from about 1% to about 50%, and especially from about 2% to about 20% by weight of the peptide or the compound. One or more peptides or compounds can be incorporated in the formulations of the disclosure, which can be prepared by any of the well-known techniques of pharmacy.

As used herein, the term "culture," refers to any sample or specimen which is suspected of containing one or more microorganisms or cells. "Pure cultures" are cultures in which the cells or organisms are only of a particular species or genus. This is in contrast to "mixed cultures," wherein more than one genus or species of microorganism or cell are present.

As used herein, the terms "treat," "treating," or "treatment of," refers to reduction of severity of a condition or at least partially improvement or modification thereof, e.g., via complete or partial alleviation, mitigation or decrease in at least one clinical symptom of the condition, e.g., Lyme disease.

As used herein, the term "administering" is used in the broadest sense as giving or providing to a subject in need of the treatment, a composition such as the compound or peptide of the disclosure, or a pharmaceutical composition containing the peptide or the compound. For instance, in the pharmaceutical sense, "administering" means applying as a remedy, such as by the placement of a peptide or an antibody in a manner in which such molecule would be received, e.g., intravenous, oral, topical, buccal (e.g., sub-lingual), vaginal, parenteral (e.g., subcutaneous; intramuscular including skeletal muscle, cardiac muscle, diaphragm muscle and smooth muscle; intradermal; intravenous; or intraperitoneal), topical (i.e., both skin and mucosal surfaces), intranasal, transdermal, intraarticular, intrathecal, inhalation, intraportal delivery, organ injection (e.g., eye or blood, etc.), or ex vivo (e.g., via immunoapheresis).

As used herein, "contacting" means that the composition comprising the active ingredient is introduced into a sample containing a target, e.g., cell target, in a test tube, flask, tissue culture, chip, array, plate, microplate, capillary, or the like, and incubated at a temperature and time sufficient to permit binding of the peptide or the compound to the target (e.g., antibodies) or vice versa (e.g., antibodies binding to *B. burgdorferi* DbpA). In the in vivo context, "contacting" means that the therapeutic or diagnostic molecule is introduced into a patient or a subject for the treatment of a Lyme disease, and the molecule is allowed to come in contact with the patient's target tissue, e.g., blood tissue, in vivo or ex vivo.

As used herein, the term "therapeutically effective amount" refers to an amount that provides some improvement or benefit to the subject. Alternatively stated, a "therapeutically effective" amount is an amount that will provide some alleviation, mitigation, or decrease in at least one clinical symptom in the subject. Methods for determining therapeutically effective amount of the therapeutic molecules, e.g., antibodies, are described below.

As used herein, the term "inhibit" refers to reduction in the amount, levels, density, turnover, association, dissociation, activity, signaling, or any other feature associated with an etiological agent of a disorder, e.g., *B. burgdorferi* or a complex containing *B. burgdorferi*.

As used herein, the term "subject" means an individual. In one aspect, a subject is a mammal such as a human. In one aspect a subject can be a non-human primate. Non-human primates include marmosets, monkeys, chimpanzees, gorillas, orangutans, and gibbons, to name a few. The term "subject" also includes domesticated animals, such as cats, dogs, etc., livestock (e.g., llama, horses, cows), wild animals (e.g., deer, elk, moose, etc.,), laboratory animals (e.g., mouse, rabbit, rat, gerbil, guinea pig, etc.) and avian species (e.g., chickens, turkeys, ducks, etc.).

Subjects can also include, but are not limited to fish, amphibians and reptiles. Subjects may further include invertebrates such as ticks, lice, and fleas. Preferably, the subject is a human subject. Especially, the subject is a human patient.

As used herein, the term "Lyme disease" refers to a medical condition that is transmitted by *B. burgdorferi* or related species, e.g., *B. afzelli*, or *B. garinii, B. lusitaniae* and *B. valaisianae*.

As used herein, the term "detecting," refers to the process of determining a value or set of values associated with a sample by measurement of one or more parameters in a sample, and may further comprise comparing a test sample against reference sample. In accordance with the present disclosure, the detection of Lyme disease in a subject may include identification, assaying, measuring and/or quantifying one or more DbpA antigens in the subject's biological sample, e.g., sputum, serum or blood.

As used herein, a "detectable label" is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of the energy source and detector used and the type of polymer, analyte, probe and primary and secondary analyte-specific binding partners. The label should be sterically and chemically compatible with the constituents to which it is bound. The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl)aminonaphthalene-1-sulfonic acid (EDANS), 4-acetamido-4'-isothiocyanatostilbene-2, 2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4', 6-diaminidino-2-phenylindole (DAPI), 5',5"-diaminidino-2-phenylindole (DAPI) or the like), a chemiluminescent molecule, a bioluminescent molecule, a chromogenic molecule, a radioisotope (e.g., $^{32}P$, $^{3}H$, $^{14}C$, $^{125}I$ and $^{131}I$), an electron spin resonance molecule (e.g., nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described in U.S. Pat. No. 6,207,392), a colloidal metal, a colloid gold, or a nuclear magnetic resonance molecule. The detectable label can also be selected from the group consisting of indirectly detectable labels such as an enzyme (e.g., alkaline phosphatase, horseradish peroxidase, p-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, etc. Antibody fragments include Fab, F(ab)2, Fd and antibody fragments which include a CDR.

The term "specific detection" refers to level of detection of a particular target ("signal") over other non-targets ("noise"). Specific detection is achieved when the signal-to-noise for the detection is at least 0.6-fold, 0.7-fold, 0.8-fold, 0.9-fold, 1-fold, 1.5-fold, 2-fold (e.g., 100% increase), 3-fold, 5-fold, 10-fold, 20-fold, 50-fold, 70-fold, 100-fold, or more.

As used herein, the term "diagnosis" refers to methods by which a determination can be made as to whether a subject is likely to be suffering from a given disease or condition, including but not limited diseases or conditions characterized by autoantibodies. The skilled artisan often makes a diagnosis on the basis of one or more diagnostic indicators, e.g., autoantibodies, the presence, absence, amount, or change in amount of which is indicative of the presence, severity, or absence of the disease or condition. Other diagnostic indicators can include patient history; physical symptoms (e.g., itch, rash, fever, chills, headache, fatigue, muscle and joint aches, and swollen lymph nodes); memory problems (e.g., short-term memory loss); late signs or symptoms such as arthritis with severe joint pain and swelling (particularly the knees and other large joints); facial palsy; intermittent pain in tendons, muscles, joints, and bones; heart palpitations or an irregular heart beat (Lyme carditis); episodes of dizziness or shortness of breath; inflammation of the brain and spinal cord; nerve pain; shooting pains, numbness, or tingling in the hands or feet. Diagnosis may include analysis of genetic or environmental or heredity factors. A skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods of the disclosure can be used independently, or in combination with other diagnosing methods, to determine whether a course or outcome is more likely to occur in a patient exhibiting a given characteristic.

As used herein the term "signal" is used in reference to an indicator that a reaction has occurred, for example, binding of antibody to antigen. It is contemplated that signals in the form of radioactivity, fluorescence reactions, luminescent and enzymatic reactions will be used with the present disclosure. The signal may be assessed quantitatively as well as qualitatively. As used herein the term "signal intensity" refers to magnitude of the signal strength wherein the intensity correlates with the amount of reaction substrate.

As used herein, the term "cell" is used interchangeably with the term "biological cell." Non-limiting examples of biological cells include eukaryotic cells, plant cells, animal cells, such as mammalian cells, insect cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immune cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, e.g., from a human, a mouse, a rat, a horse, a goat, a sheep, a cow, a primate, etc.

As used herein, the term "sample" refers to a composition that is obtained or derived from a subject of interest that contains a cellular and/or other molecular entity that is to be characterized and/or identified, for example based on physical, biochemical, chemical and/or physiological characteristics.

As used herein a "biological sample" is a substance obtained from the subject's body. The particular "biological sample" selected will vary based on the disorder the patient is suspected of having and, accordingly, which biological sample is most likely to contain the analyte. The source of the tissue sample may be blood or any blood constituents; bodily fluids; solid tissue as from a fresh, frozen and/or preserved organ or tissue sample or biopsy or aspirate; and cells from any time in gestation or development of the subject or plasma. Samples include, but not limited to, primary or cultured cells or cell lines, cell supernatants, cell lysates, platelets, serum, plasma, vitreous fluid, ocular fluid, lymph fluid, synovial fluid, follicular fluid, seminal fluid, amniotic fluid, milk, whole blood, urine, cerebrospinal fluid (CSF), saliva, sputum, tears, perspiration, mucus, tumor lysates, and tissue culture medium, as well as tissue extracts such as homogenized tissue, tumor tissue, and cellular extracts. Samples further include biological samples that have been manipulated in any way after their procurement, such as by treatment with reagents, solubilized, or enriched for certain components, such as proteins or nucleic acids, or embedded in a semi-solid or solid matrix for sectioning purposes, e.g., a thin slice of tissue or cells in a histological sample. Preferably, the sample is obtained from blood or blood components, including, e.g., whole blood, plasma, serum, lymph, and the like.

The term "control," as used herein, refers to a reference for a test sample, such as a sample obtained from a subject who is undiagnosed or unsuspected of having a disease (e.g., Lyme disease). A "reference sample," as used herein, refers to a sample of tissue or cells that may or may not have Lyme diseases that are used for comparisons. Thus a "reference" sample thereby provides a basis to which another sample, for example plasma sample containing markers, e.g., DbpA antigen, can be compared. A "test sample" refers to a sample compared to a reference sample or control sample. In some embodiments, the reference sample or control may comprise molecules that have a pre-defined activity, e.g., ability or inability to bind specifically to an anti-DbpA antibody such as monoclonal antibody 6G8 and/or 8C10.

As used herein "presence" means the level of analyte (e.g., DbpA antigen) which is greater by a statistically significant amount than the level of analyte present in a particular biological sample of a subject that is not suffering from a disease. For Lyme disease, an elevated level of the analyte may mean an increase of about 20%, 50%, 75%, 100%, 150%, 200%, 300%, 400%, or more, e.g., 500%, of DbpA antigen, compared to that of subject who is not suffering from Lyme disease. This differentiation enables the diagnostic aspects of the present disclosure.

Anti-DbpA Antibodies and Compositions Thereof

The present disclosure relates to isolated, recombinant and/or synthetic antibodies that bind to decorin-binding protein A (DbpA) of *B. burgdorferi* and microorganisms related thereto. Decorin binding protein (DbpA) is a lipoprotein that contributes to the adhesion and colonization of *B. burgdorferi* within mammalian hosts. DbpA-encoding genes reside in an operon (dbpBA) inside linear plasmid 54 (lp54), which are present in the genomes of many *B. burgdorferi* sensu lato isolates. Although DbpA is not expressed in vector ticks, its expression is upregulated in the mammalian host after ticks deposit spirochetes into the skin of mammals. The protein binds to decorin, a connective-tissue proteoglycan which binds to type I collagen fibrils and plays a role in matrix assembly. The expression of DbpA by *B. burgdorferi* is high during the infectivity period, as evidenced by circulating antibodies against the protein in both laboratory animal models as well as in clinical human patients.

Described herein are monoclonal antibodies against *B. burgdorferi* surface antigen DbpA. Monoclonal antibodies which bind with specificity to an antigenic epitope in *B. burgdorferi* DbpA were obtained by immunizing animals (e.g., mice) with the antigen and antibody isolates were prepared and further screened using hybridoma screening technology. The hybridoma clones were sequenced by RT-PCR technology to obtain unique antibody sequences, based on which, humanized chimeric antibodies were designed to include the mouse variable region domains and human Fc region from an IgM framework.

Preliminary studies on the binding properties of the chimeric antibodies using SPR (e.g., BIACORE assay) demonstrated that the chimeric antibodies of the disclosure specifically bound to an antigenic epitope in *B. burgdorferi* DbpA. To generate monoclonal antibody-producing hybridomas, full-length immunoglobulin gene transcripts of two antibody clones, 6G8 and 8C10, were obtained and the IgG VH/VL regions thereof were PCR amplified. The product was ligated with framework sequences for immunoglobulin genes (e.g., IgM) and the chimeric polynucleotide was cloned into a mammalian expression vector. Chimeric antibodies (e.g., IgM) were expressed and produced from the secreted media.

Small scale cell culture and purification experiments in HEK 293 cells were carried out for antibody functional analysis. About 0.18 mg of 6G8 and about 1.6 mg of 8C10 antibodies were purified from 30 ml cell culture, indicating that antibody titer at 5.4 mg/L and 52 mg/L, respectively, could be achieved by scaling up. Further purification schemes were developed for large scale production. Validation batches of chimera expression and purification were produced.

Biochemical characterization of the purified antibodies using immunoblotting revealed that the antibodies comprise a heavy chain of about 80 kDa and a light chain of about 25 kDa under reducing sodium dodecylsulfate polyacrilimide gel electrophoretic (SDS-PAGE) resolution and higher molecular bands (e.g., bands larger than 500 kDa) were observed using non-reducing conditions. The purified antibodies showed as one major dominant peak on HPLC-SEC (retention time of about 3.8 mins, corresponding to human IgM molecular weight).

BIACORE testing with the DbpA antigen immobilized on CM5 chip demonstrated specific binding between the DbpA and the purified antibody, confirming that the recombinant antibodies retained the three-dimensional conformation of antibody domains involved in antigen-binding. The dissociation constant (Kd) was about $10^{-12}$ M, indicating that the chimeric antibody of the disclosure has an exceptionally strong affinity for the DbpA antigen. Furthermore, immunoassay studies reveal that the monoclonal antibodies served as sensitive DbpA-specific standards and calibrators for an IgM immunoassay. These findings demonstrate a general utility of the chimeric antibodies, including, antigen-binding fragments thereof, in the detection of DbpA antigens in biological (e.g., human serum) or environmental (e.g., tick) samples. The antibody compositions of the disclosure are particularly useful in serological testing of patient samples for diseases that are mediated by *B. burgdorferi*, e.g., Lyme disease.

In some embodiments, DbpA relates to a *B. burgdorferi* DbpA polypeptide (UNIPROT Accession No. O50917; version 92, last revised: Mar. 28, 2018), including variants and mutants thereof or an immunogenic fragment thereof. Preferably, DbpA relates to a *B. burgdorferi* DbpA having polypeptide sequence set forth in SEQ ID NO: 78, including, variants or mutants thereof, as recited in Table 1 or a fragment of SEQ ID NO: 78 or its variant or mutant.

In one embodiment, the amino acid sequence of wild-type *B. burgdorferi* DbpA is recited in SEQ ID NO: 78, below. Amino acids making up the signal sequence (aa 1-29) are underlined.

```
                                    (SEQ ID NO: 78)
         10         20         30         40
MIKCNNKTFN NLLKLTILVN LLISCGLTGA TKIRLERSAK 50         60         70         80
DITDEIDAIK KDAALKGVNF DAFKDKKTGS GVSENPFILE
```

```
                  -continued
         90        100       110       120
    AKVRATTVAE KFVIAIEEEA TKLKETGSSG EFSAMYDLMF 130       140       150       160
    EVSKPLQKLG IQEMTKTVSD AAEENPPTTA QGVLEIAKKM 170       180       190
    REKLQRVHTK NYCTLKKKEN STFTDEKCKN N
```

TABLE 1

Natural variants and/or mutants of wild-type DbpA (SEQ ID NO: 78)

| Feature key | Position(s) in SEQ#Y | Description Actions |
|---|---|---|
| Natural variant | 34 | R → K in strain: 297, LP7 and Sh-2-82. |
| Natural variant | 37 | R → S in strain: 297, LP7 and Sh-2-82. |
| Natural variant | 41-43 | DIT → AIV in strain: 297, LP7 and Sh-2-82. |
| Natural variant | 52 | D → K in strain: 297, LP7 and Sh-2-82. |
| Natural variant | 55-56 | LK → SM in strain: 297, LP7 and Sh-2-82. |
| Natural variant | 128 | K → E in strain: 297, LP7 and Sh-2-82. |
| Natural variant | 140 | D → M in strain: 297, LP7 and Sh-2-82. |
| Natural variant | 169 | T → K in strain: 297, LP7 and Sh-2-82. |
| Natural variant | 172-173 | YC → QD in strain: 297, LP7 and Sh-2-82. |
| Natural variant | 179-191 | ENSTF (SEQ ID NO: 81) . . . KCKNN (SEQ ID NO: 82) → NTEDSTAKS (SEQ ID NO: 83) in strain: 297, LP7 and Sh-2-82. |

In some embodiments, DbpA relates to homologs of wild-type B. burgdorferi DbpA (SEQ ID NO: 78), which are structurally and/or functionally similar to B. burgdorferi DbpA. Representative homologs include members having at least 70%, 80% or 90% identity, at the genomic, trancriptomic, or proteomic level to wild-type B. burgdorferi DbpA (SEQ ID NO: 78), e.g., proteins in the cluster UNIREF90_O50917 (published: Aug. 30, 2017), e.g., DbpA from B. japonica, B. finlandensis or B. garinii.

In some embodiments, DbpA relates to a fragment of B. burgdorferi DbpA. Particularly, the DbpA fragment comprises an N-terminal antigenic domain of DbpA, comprising, e.g., from about aa 24 to about aa 191 of SEQ ID NO: 78, including, a fragment comprising, consisting essentially of, or consisting of, aa 21-194, aa 22-194, aa 23-194, aa 24-194, aa 25-194, aa 26-194, aa 27-194, aa 21-193, aa 22-193, aa 23-193, aa 24-193, aa 25-193, aa 26-193, aa 27-193, aa 21-192, aa 22-192, aa 23-192, aa 24-192, aa 24-192, aa 26-192, aa 27-192, aa 21-191, aa 22-191, aa 23-191, aa 24-191, aa 25-191, aa 26-191, aa 27-191, aa 21-190, aa 22-190, aa 23-190, aa 24-190, aa 25-190, aa 26-190, aa 27-190, aa 21-189, aa 21-189, aa 22-189, aa 23-189, aa 24-189, aa 25-189, aa 26-189, aa 27-189, aa 21-188, aa 22-188, aa 23-188, aa 24-188, aa 25-188, aa 26-188, or aa 27-188 of SEQ ID NO: 78 (+/−3 amino acids from the termini).

Especially, DbpA polypeptide of the disclosure relates to polypeptide which comprises, consists essentially of, or consists of the sequence set forth in SEQ ID NO: 77 or in SEQ ID NO: 78 (e.g., a polypeptide comprising, consisting essentially of, or consisting of aa 24-191 of SEQ ID NO: 78 or SEQ ID NO: 77) or an immunogenic fragment thereof.

The disclosure further relates to antibodies that bind to immunogenic fragment of SEQ ID NO: 77, which comprises at least one epitope to which the antibodies of the disclosure, e.g., MAb 6G8 and/or MAb 8C10, specifically bind to. The at least one epitope can comprise at least one antibody binding region that comprises at least one portion of DbpA protein, which epitope comprises 1, 2, 3, 4, 5, 6 or more amino acids of a DbpA fragment of SEQ ID NO: 77. Particularly, the disclosure relates to epitopes on the DbpA protein defined by the epitope of MAb 6G8 or MAb 8C10, and/or which compete for binding to DbpA with antibody MAb 6G8 or MAb 8C10, or which have other functional binding characteristics exhibited by or MAb 6G8 or MAb 8C10. In some embodiments, the immunogenic fragments may comprise about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, or 165 contiguous amino acids of SEQ ID NO: 77.

In some embodiments, the disclosure relates to a DbpA antibody which functionally affects DbpA ligand or a function thereof. Preferably, the antibodies of the disclosure bind to and/or sequester DbpA. In some embodiments, the antibody modulates, decreases, increases, antagonizes, agonizes, mitigates, alleviates, blocks, inhibits, abrogates and/or interferes with at least one biological activity of DbpA in vitro, in situ, ex vivo, and/or in vivo.

In some embodiments, the disclosure relates to anti-DbpA monoclonal antibody or an antigen-binding fragment thereof. In some embodiments, the antibodies are anti-DbpA chimeric antibodies, particularly, anti-DbpA chimeric monoclonal antibodies or an antigen-binding fragment thereof. Particularly, the antibodies are humanized anti-DbpA antibodies, especially, anti-DbpA humanized monoclonal antibodies or an antigen-binding fragment thereof.

The disclosure relates to antibodies having the amino acid sequence of monoclonal antibodies 6G8 and/or 8C10, chains thereof, e.g., heavy chain (VH) and light chain (VL) variable regions, and fragments thereof, e.g., antigen-binding fragments comprising CDRs of monoclonal antibodies (MAb) 6G8 and/or 8C10.

In some embodiments, the disclosure relates to antibodies having the CDRs of MAb 6G8, e.g., heavy chain CDRs ($CDR_H$) and/or light chain CDRs ($CDR_L$). In such embodiments, the antibody or antigen-binding fragment thereof comprises a $CDR_H$ comprising one or more CDRs comprising (1) $CDR_{H1}$ comprising, consisting essentially of, or consisting of the sequence RYWMYW (SEQ ID NO: 1) or a variant thereof comprising, consisting essentially of, or consisting of at least 80%, 90%, or 95% sequence identity thereto; (2) $CDR_{H2}$ comprising, consisting essentially of, or consisting of the sequence RLDPNSGVTKYNEKFKS (SEQ ID NO: 2) or a variant thereof comprising, consisting essentially of, or consisting of at least 80%, 90%, or 95% sequence identity thereto; and/or (3) $CDR_{H3}$ comprising, consisting essentially of, or consisting of the sequence DDSWYFDV (SEQ ID NO: 3) a variant thereof comprising, consisting essentially of, or consisting of at least 80%, 90%, or 95% sequence identity thereto. Alternately or additionally, the antibody or antigen-binding fragment thereof may comprise a $CDR_L$ comprising one or more CDRs comprising (4) $CDR_{L1}$ comprising, consisting essentially of, or consisting of the sequence QATQDIVKNLN (SEQ ID NO: 4) or a variant thereof comprising, consisting essentially of, or consisting of at least 80%, 90%, or 95% sequence identity thereto; (5) $CDR_{L2}$ comprising, consisting essentially of, or consisting of the sequence YATELAE (SEQ ID NO: 5) or a variant thereof comprising, consisting essentially of, or consisting of at least 80%, 90%, or 95% sequence identity thereto; and/or (6) $CDR_{L3}$ comprising, consisting essentially of, or consisting of the sequence LQFYAFPLT (SEQ ID NO: 6) or a variant thereof comprising, consisting essentially of, or consisting of at least 80%, 90%, or 95% sequence identity thereto.

In some embodiments, the disclosure relates to antibodies having the CDRs of MAb 8C10, e.g., heavy chain CDRs ($CDR_H$) and/or light chain CDRs ($CDR_L$). In such embodiments, the antibody or antigen-binding fragment thereof comprises a $CDR_H$ comprising one or more CDRs comprising (1) $CDR_{H1}$ comprising, consisting essentially of, or consisting of the sequence DYWIE (SEQ ID NO: 7) or a variant thereof comprising, consisting essentially of, or consisting of at least 80%, 90%, or 95% sequence identity thereto; (2) $CDR_{H2}$ comprising, consisting essentially of, or consisting of the sequence EILPGSGSTKDNERFKG (SEQ ID NO: 8) or a variant thereof comprising, consisting essentially of, or consisting of at least 80%, 90%, or 95% sequence identity thereto; and (3) $CDR_{H3}$ comprising, consisting essentially of, or consisting of the sequence REWGYYFDY (SEQ ID NO: 9) or a variant thereof comprising, consisting essentially of, or consisting of at least 80%, 90%, or 95% sequence identity thereto. Alternately or additionally, the $CDR_L$ may comprise one or more CDRs comprising (4) $CDR_{L1}$ comprising, consisting essentially of, or consisting of the sequence KASQDVSTAVA (SEQ ID NO: 10) or a variant thereof comprising, consisting essentially of, or consisting of at least 80%, 90%, or 95% sequence identity thereto; (5) $CDR_{L2}$ comprising, consisting essentially of, or consisting of the sequence IYWASTRHT (SEQ ID NO: 11) or a variant thereof comprising, consisting essentially of, or consisting of at least 80%, 90%, or 95% sequence identity thereto; and/or (6) $CDR_{L3}$ comprising, consisting essentially of, or consisting of the sequence QQHYSTPYT (SEQ ID NO: 12) or a variant thereof comprising, consisting essentially of, or consisting of at least 80%, 90%, or 95% sequence identity thereto.

In some embodiments, the disclosure relates to antibodies containing variant paratopes. While antibody paratopes are often defined by CDRs, not all the residues within the CDRs are involved in antigen-binding. In fact, an early analysis of the 3-D structures of antibodies suggested that only 20-33% of the residues within the CDRs participate in antigen-binding (Padlan et al., *Mol Immunol.*, 31(3):169-217, 1994). Amino acid residues within CDRs that contact with the antigen are now recognized to serve as better proxies for paratope (Sela-Culang et al., *Front Immunol.*, 4, 302, 2013). Large-scale analyses of protein-antibody complexes deposited in Protein Data Bank (PDB) have enabled identification of structural regions in antibodies that are involved in antigen-binding (Kunik et al., *PLoS Comput Biol.*, 8(2): e1002388, 2012; Kunik et al., *Nucleic Acids Res.*, 40, W521-4, 2012). Such large scale analysis using integrated software (e.g., PARATOME) has enabled detailed analysis of CDRs, including, identification of determinants that are actually involved in antigen-binding. For instance, paratomic analysis of PDB deposits has revealed that the length and/or composition of $CDR_{L3}$ and $CDR_{H3}$ are unchanged between various numbering schemes, while in other CDRs (e.g., L2, H1, and H2) there are substantial differences between the schemes. Also, computational analyses of next-generation sequencing (NGS) data of antibody-encoding genes have enabled classification of discrete classes of CDRs (termed canonical classes). The results show that $CDR_{L2}$ is the least diverse in terms of length, with around 99% of known structures belonging to the same class, while $CDR_{H3}$ is the most diverse (Nowak et al., *MAbs*, 8(4): 751-760, 2016). Accordingly, the disclosure relates to minimal antibodies or antigen-binding fragments thereof comprising less than the full complement of six CDRs which specifically bind to DbpA fragment of SEQ ID NO: 77 or an immunogenic fragment thereof. In some embodiments, such minimal antibodies or antigen-binding fragments thereof may comprise at least three heavy chain CDRs (e.g., $CDR_{H1}$, $CDR_{H2}$, and $CDR_{H3}$) optionally together with one or more light chain CDRs (e.g., $CDR_{L1}$ and/or $CDR_{L2}$ and/or $CDR_{L3}$) and still bind with specificity to DbpA fragment of SEQ ID NO: 77 or an immunogenic fragment thereof. Non-limiting examples of such minimal antibodies include, e.g., (a) an MAb 6G8-derived minimal antibody comprising $CDR_{H1-3}$ comprising, consisting essentially of, or consisting of, the sequences set forth in SEQ ID Nos: 1-3 (or variants thereof), optionally together one or more $CDR_{L1-3}$ comprising, consisting essentially of, or consisting of, the sequences set forth in SEQ ID Nos: 4-6 (or variants thereof); or (b) an MAb 8C10-derived minimal antibody comprising $CDR_{H1-3}$ comprising, consisting essentially of, or consisting of, the sequences set forth in SEQ ID Nos: 7-9 (or variants thereof), optionally together one or more $CDR_{L1-3}$ comprising, consisting essentially of, or consisting of, the sequences set forth in SEQ ID Nos: 10-12 (or variants thereof), wherein the minimal antibody of (a) or (b) specifically binds to DbpA fragment SEQ ID NO: 77 or an immunogenic fragment thereof.

In some embodiments, the recombinant antibodies of the disclosure comprise the heavy and light chain CDR3s of MAb 6G8 or MAb 8C10. The antibodies can further comprise the CDR2s of MAb 6G8 or MAb 8C10. The antibodies can further comprise the CDR1s of MAb 6G8 or MAb 8C10. Accordingly, the disclosure relates to anti-DbpA antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of MAb 6G8 as shown in SEQ ID NO: 3; and (2) human light chain framework regions, a human light chain CDR1 region, a human light chain CDR2 region, and a human light chain CDR3 region, wherein the human light chain CDR3 region is selected from the CDR3s of MAb 6G8 as shown in SEQ ID NO: 6, wherein the antibody binds DbpA. The antibody may further comprise the heavy chain CDR2 and/or the light chain CDR2 of MAb 6G8. The antibody may further comprise the heavy chain CDR1 and/or the light chain CDR1 of MAb 6G8. The disclosure also provides anti-DbpA antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of MAb 8C10 as shown in SEQ ID NO: 9; and (2) human light chain framework regions, a human light chain CDR1 region, a human light chain CDR2 region, and a human light chain CDR3 region, wherein the human light chain CDR3 region is selected from the CDR3s of MAb 6G8 as shown in SEQ ID NO: 12, wherein the antibody binds DbpA. The antibody may further comprise the heavy chain CDR2 and/or the light chain CDR2 of MAb 8C10. The antibody may further comprise the heavy chain CDR1 and/or the light chain CDR1 of MAb 8C10.

Purely as a non-limiting example, in some embodiments, the antibody or antigen-binding portion or variant can comprise at least one of the heavy chain CDR3 having the amino acid sequence of SEQ ID NO: 3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the antibody or antigen-binding fragment have the amino acid sequence of the corresponding CDR of at least one of MAb 6G8 or MAb 8C10, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or using any suitable methods.

Preferably, the CDR1, 2, and/or 3 of the engineered antibodies described above comprise the exact amino acid sequence(s) as those of MAb 6G8 or MAb 8C10 disclosed herein. However, the ordinarily skilled artisan will appreciate that some deviation from the exact CDR sequences of MAb 6G8 or MAb 8C10 may be possible while still retaining the ability of the antibody to bind DbpA effectively (e.g., conservative substitutions). Accordingly, in another embodiment, the engineered antibody may be composed of one or more CDRs that are, for example, at least 80%, 90%, 95%, or more, e.g., 97% identical to one or more CDRs of MAb 6G8 or MAb 8C10. In addition to simply binding DbpA, engineered antibodies such as those described above may be selected for their retention of other functional properties of antibodies of the disclosure.

In some embodiments, the disclosure relates to antibodies comprising framework regions (FR) of MAb 6G8 comprising heavy chain framework regions 1-3 and/or light chain framework regions 1-3, wherein heavy chain FR1 comprises, consists essentially of, or consists of the polypeptide sequence set forth in QVQLQQPGAELVKPGASVKLSCK-ASGYTF (SEQ ID NO: 13) or a polypeptide having at least 80%, 90%, 95%, or more, e.g., 97% sequence identity thereto; heavy chain FR2 comprises, consists essentially of, or consists of the polypeptide sequence set forth in WVKQRPGRGLEWIG (SEQ ID NO: 14) or a polypeptide having at least 80%, 90%, 95%, or more, e.g., 97% sequence identity thereto; and heavy chain FR3 comprises, consists essentially of, or consists of the polypeptide sequence set forth in KATLTVDKSSSTAYMQLSSLTSED-SAVYYCVRDDS (SEQ ID NO: 15) or a polypeptide having at least 80%, 90%, 95%, or more, e.g., 97% sequence identity thereto; and light chain FR1 comprises, consists essentially of, or consists of the polypeptide sequence set forth in MTQSPSSMSASLGDRITITC (SEQ ID NO: 16) or a polypeptide having at least 80%, 90%, 95%, or more, e.g., 97% sequence identity thereto; light chain FR2 comprises, consists essentially of, or consists of the polypeptide sequence set forth in WYQQKPGKPPSFLIY (SEQ ID NO: 17) or a polypeptide having at least 80%, 90%, 95%, or more, e.g., 97% sequence identity thereto; and light chain FR3 comprises, consists essentially of, or consists of the polypeptide sequence set forth in RGPSRFSGSGSGSDYS-LTINNLESQDFADYFC (SEQ ID NO: 18) or a polypeptide having at least 80%, 90%, 95%, or more, e.g., 97% sequence identity thereto.

In some embodiments, the disclosure relates to antibodies comprising framework regions (FR) of MAb 8C10 comprising heavy chain framework regions 1-3 and/or light chain framework regions 1-3, wherein heavy chain FR1 comprises, consists essentially of, or consists of the polypeptide sequence set forth in QVQLQQSGAELMKPGASVKLSC-KAAGYTFT (SEQ ID NO: 19) or a polypeptide having at least 80%, 90%, 95%, or more, e.g., 97% sequence identity thereto; heavy chain FR2 comprises, consists essentially of, or consists of the polypeptide sequence set forth in WVKQRPGHGLEWIG (SEQ ID NO: 20) or a polypeptide having at least 80%, 90%, 95%, or more, e.g., 97% sequence identity thereto; and heavy chain FR3 comprises, consists essentially of, or consists of the polypeptide sequence set forth in KATFTADTSSNTAYMQLSSLTTEDSAIYYCAR (SEQ ID NO: 21) or a polypeptide having at least 80%, 90%, 95%, or more, e.g., 97% sequence identity thereto; and light chain FR1 comprises, consists essentially of, or consists of the polypeptide sequence set forth in DIVMTQSHKFMSTSVGDRVSITC (SEQ ID NO: 22) or a polypeptide having at least 80%, 90%, 95%, or more, e.g., 97% sequence identity thereto; light chain FR2 comprises, consists essentially of, or consists of the polypeptide sequence set forth in WYQQKPGQSPKLLIY (SEQ ID NO: 23) or a polypeptide having at least 80%, 90%, 95%, or more, e.g., 97% sequence identity thereto; and light chain FR3 comprises, consists essentially of, or consists of the polypeptide sequence set forth in GVPDRFTGSGSGTDYTLTISSVQAEDLALYYC (SEQ ID NO: 24) or a polypeptide having at least 80%, 90%, 95%, or more, e.g., 97% sequence identity thereto.

The disclosure further relates to variants of the antibodies of the disclosure or antigen-binding fragments thereof. In some embodiments, the variants may comprise one or more variations (e.g., mutations such as deletion or substitution) of one or more amino acid residues in the antigen-binding domains and/or framework regions in the parent antibody, wherein the variant antibody specifically binds to DbpA. Preferably, the variant comprises variation in the non-antigen-binding regions in the antibody, e.g., variations in the Fc portion, the hinge portion, or the framework regions of the antibody.

In some embodiments, the variant antibodies comprise variations in the amino acids in the CDRs. In some embodiments, the variants comprise, at most 3, 2, or 1 mutation comprising addition of an amino acid, deletion of an amino acid or substitution of an amino acid with another proteinogenic amino acid or non-proteinogenic amino acid. Preferably, such engineered antibodies may comprise one or more CDRs comprising at most 3, 2, or 1 semi-conservative or conservative substitution (especially conservative substitutions) in one or more CDRs of MAb 6G8 or MAb 8C10. In addition to simply binding DbpA, such variant antibodies may be selected for their retention of other functional properties of antibodies of the disclosure.

In some embodiments, variant antibodies of the disclosure comprising variant CDRs do not contain mutations (e.g., deletions or non-conservative substitutions) of amino acid residues that are common to CDRs in the aforementioned MAbs 6G8 and 8C10. Methods for identifying such common amino acids are known, for example, by aligning sequences of CDRs using, e.g., simple sequence alignment (SIM), CLUSTAL alignment, Chothia alignment, alignment using dynamic time warping (DTW) algorithm, IMGT alignment, PDB multiple structure alignment (MSTA) or a combination thereof.

In some embodiments, variant antibodies of the disclosure comprising variant CDRs do not contain mutations in the following amino acid residues:

(1) $CDR_{H1}$: $^2Y$ and/or $^3W$ (relative to SEQ ID NO: 1);
(2) $CDR_{H2}$: $^4P$, $^6S$, $^7G$, $^9T$, $^{10}K$, $^{12}N$, $^{13}E$, $^{16}F$ and/or $^{17}K$ (relative to SEQ ID NO: 2);
(3) $CDR_{H3}$: $^6F$ (relative to SEQ ID NO: 3);
(4) $CDR_{L1}$: $^2A$, $^4Q$, and/or $^5D$ (relative to SEQ ID NO: 4);
(5) $CDR_{L2}$: $^1Y$ (relative to SEQ ID NO: 5); and/or
(6) $CDR_{L3}$: $^2Q$, $^4Y$, $^7P$ and/or $^9T$ (relative to SEQ ID NO: 6).

In instances wherein the amino acid residues in the CDRs are mutated, the mutation preferably comprises a conservative substitution Conservative amino acid substitutions of proteinogenic amino acids with other proteinogenic amino acids are generally from within the groups in Table 2.

TABLE 2

Exemplary amino acid substitutions

| Amino Acid | Exemplary Conservative Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

To identify or design peptide sequences of the antibodies or antigens of the disclosure other than those specifically disclosed herein, amino acid substitutions may be based on any characteristic known in the art, including the relative similarity or differences of the amino acid side-chain substituents, for example, their hydrophobicity, hydrophilicity, charge, size, and the like. For example, the hydropathic index of amino acids may be considered. The importance of the hydropathic amino acid index in conferring interactive biologic function on a protein is generally understood in the art (see, Kyte et al., J Mol. Biol. 757:105 (1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Amino acid have recognized hydropathic index values based on their hydrophobicity and charge characteristics, e.g., isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Amino acid substitutions can be made to preserve the general hydropathic character of the original amino acid, for example by replacing isoleucine with valine. Similarly, amino acid substitutions can be made on the basis of hydrophilicity. See U.S. Pat. No. 4,554,101 at Table 2, which assigns the following hydrophilicity values to the amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Accordingly, the hydrophilicity of the amino acid (or amino acid sequence) may be considered when identifying additional peptides beyond those specifically disclosed herein.

Preferably, the antibodies of the disclosure or antigen-binding fragments thereof comprise all six CDRs of the monoclonal antibodies which specifically bind to the polypeptide of SEQ ID NO: 77. Accordingly, the disclosure relates to antibodies or antigen-binding fragments thereof comprising (a) all six CDRs of MAb 6G8 comprising $CDR_{H1}$-3 comprising, consisting essentially of, or consisting of, the sequences set forth in SEQ ID Nos: 1-3 and $CDR_{L1}$-3 comprising, consisting essentially of, or consisting of, the sequences set forth in SEQ ID Nos: 4-6; or (b) all six CDRs of MAb 8C10 comprising $CDR_{H1}$-3 comprising, consisting essentially of, or consisting of, the sequences set forth in SEQ ID Nos: 7-9 and $CDR_{L1}$-3 comprising, consisting essentially of, or consisting of, the sequences set forth in SEQ ID Nos: 10-12.

The disclosure further relates to antibodies or fragments thereof that specifically bind to DbpA fragment of SEQ ID NO: 77 or an immunogenic fragment thereof and also specifically bind to full-length DbpA comprising SEQ ID NO: 78 or a variant thereof. In some embodiments, the full-length DbpA is present on the surface of B. burgdorferi. In some embodiments, the full-length DbpA is secreted by the B. burgdorferi. In some embodiments, the full-length DbpA is in complex with an ECM component, e.g., decorin.

In some embodiments, the structural features of the antigen-binding domains in MAb 6G8 or MAb 8C10 are used to create structurally related anti-DbpA antibodies that retain at least one functional property of the antibodies of the disclosure, such as binding to DbpA. More specifically, one or more CDR regions of MAb 6G8 or MAb 8C10 can be combined recombinantly with known human framework regions and CDRs to create additional, recombinantly-engineered, anti-DbpA antibodies of the disclosure.

Engineered antibodies of the disclosure, once made, can be tested for binding to DbpA using routine assays, for example, sandwich immunoassay complex formation, enzyme-linked immunoassay, radioimmunoassay, immunoprecipitation assay, fluorescence immunoassay, chemiluminescent assay, immunoblot assay, lateral flow assay, flow cytometry assay, mass spectrometry assay, direct binding assay, antibody or antigen displacement assay, latex agglutination, indirect hemagglutination assay (IHA), complement fixation assay, inhibition assay, avidity assay, a dipstick test, particulate-based assay, surface plasmon resonance (SPR) assay (e.g., BIACORE). In preferred embodiments, antigenic peptide-antibody complexes described herein are detected using enzyme-linked immunoassay (ELISA), lateral flow assay, direct binding assay or SPR.

To determine if selected anti-DbpA antibodies bind to unique epitopes, each antibody can be biotinylated using commercially available reagents (Pierce, Rockford, Ill., USA). Competition studies using unlabeled ("cold") antibodies and biotinylated ("hot") antibodies can be performed using DbpA coated-ELISA plates. Biotinylated mAb binding can be detected with a strep-avidin-alkaline phosphatase probe. If the cold antibody competes with (and/or displaces) the hot antibody for binding to the antigen, then it can be inferred that the two antibodies share a common epitope or that the epitope of the cold antibody is in close proximity with the epitope of the hot antibody. Kinetic studies can be further conducted to assess whether the cold antibody is allosterically inhibiting the binding between the hot antibody and the antigen.

To determine the isotype of purified antibodies, isotype ELISAs can be performed. In order to demonstrate binding of monoclonal antibodies to live cells expressing the DbpA, flow cytometry can be used. Anti-DbpA immunoglobulins can be further tested for reactivity with DbpA antigen by Western blotting.

In another aspect of the disclosure, the structural features (e.g., amino sequences or three-dimensional structures or both) of anti-DbpA antibodies of the disclosure, MAb 6G8 or MAb 8C10, may be used to create structurally related anti-DbpA antibodies that retain at least one functional property of the antibodies of the disclosure, such as binding to DbpA. More specifically, one or more CDR regions of MAb 6G8 or MAb 8C10 can be combined recombinantly with known human framework regions and CDRs to create additional, recombinantly-engineered, anti-DbpA antibodies of the disclosure. For example, given the high degree of sequence identity (about 90%) between the heavy framework 1 ($FR_{H1}$) sequences of MAb 6G8 (SEQ ID NO: 13) and MAb 8C10 (SEQ ID NO: 19), the $FR_{H1}$ sequences of the two antibodies could be swapped such that 8C10 $FR_{H1}$ sequence of SEQ ID NO: 19 is used as framework for 6G8 $CDR_{H1}$ sequence of SEQ ID NO: 1 or 6G8 $FR_{H1}$ sequence of SEQ ID NO: 13 is used is used as framework for 8C10 $CDR_{H1}$ sequence of SEQ ID NO: 7. Given the relatively high degree of sequence identity between various framework sequences, other framework regions could also be swapped to create new variants, e.g., swapping of $FR_{H2}$ sequences of MAb 6G8 (SEQ ID NO: 14) and 8C10 (SEQ ID NO: 20) (about 93% sequence identity); swapping of $FR_{H3}$ sequences of MAb 6G8 (SEQ ID NO: 15) and 8C10 (SEQ ID NO: 21) (about 78% sequence identity); swapping of light framework 1 ($FR_{L1}$) sequences of MAb 6G8 (SEQ ID NO: 16) and 8C10 (SEQ ID NO: 22) (about 65% sequence identity); swapping of $FR_{L2}$ sequences of MAb 6G8 (SEQ ID NO: 17) and 8C10 (SEQ ID NO: 23) (about 73% sequence identity); and/or swapping of $FR_{L3}$ sequences of MAb 6G8 (SEQ ID NO: 18) and 8C10 (SEQ ID NO: 24) (about 57% sequence identity).

In some embodiments, the disclosure relates to molecules comprising antigen-binding sequences comprising a variable heavy chain (VH) and/or a variable light chain (VL) domain, wherein the VH comprises $FR_{H1}$-$CDR_{H1}$-$FR_{H2}$-$CDR_{H2}$-$FR_{H3}$-$CDR_{H3}$ and/or VL comprises $FR_{L1}$-$CDR_{L1}$-$FR_{L2}$-$CDR_{L2}$-$FR_{L3}$-$CDR_{L3}$, wherein $FR_{1-3}$, in each VH or VL chain, represent antibody framework regions; and wherein $CDR_{1-3}$, in each VH or VL chain, represent antibody complementary determining regions. Non-limiting examples of such molecules include, e.g., polypeptides comprising, consisting essentially of, or consisting of, the following amino acid sequences for VH and/or VL chains ("–" indicates a bond, preferably a peptide bond):

(a) VH: SEQ ID NO: 13-SEQ ID NO: 1-SEQ ID NO: 14-SEQ ID NO: 2-SEQ ID NO: 15-SEQ ID NO: 3; VL: SEQ ID NO: 16-SEQ ID NO: 4-SEQ ID NO: 17-SEQ ID NO: 5-SEQ ID NO: 18-SEQ ID NO: 6; preferably, the VH and VL sequences are set forth in the sequences QVQLQQPGAELVKPGASVKLSCK-ASGYTFTRYWMYWVKQRPGRGLEWI-GRLDPNSGVTKYNEKF KSKATLTVDKSSSTAYMQLSSLTSEDSAVYYCVRDD-SWYFDV (SEQ ID NO: 25) and EIQMTQSPSSM-SASLGDRITITCQATQDI-VKNLNWYQQKPGKPPSFLIYYATELAEGVPSRFSG SGSGSDYSLTINNLESQDFADYFCLQFYAFPLT (SEQ ID NO: 26), respectively.

(b) VH: SEQ ID NO: 19-SEQ ID NO: 7-SEQ ID NO: 20-SEQ ID NO: 8-SEQ ID NO: 21-SEQ ID NO: 9; VL: SEQ ID NO: 22-SEQ ID NO: 10-SEQ ID NO: 23-SEQ ID NO: 11-SEQ ID NO: 24-SEQ ID NO: 12; preferably, the VH and VL sequences are set forth in the sequences QVQLQQSGAELMKPGASVKLSCKAAGYTFTDY-WIEWVKQRPGHGLEWIGEILPGSGSTKDNERF KGKATFTADTSSNTAYMQLSSLTTEDSAIYYCAR-REWGYYFDY (SEQ ID NO: 27) and DIVMTQSHKFMSTSVGDRVSITCKASQDVSTA-VAWYQQKPGQSPKLLIYWASTRHTGVPDRFTG SGSGTDYTLTISSVQAEDLALYYCQQHYSTPYT (SEQ ID NO: 28), respectively.

(c) a variant of the molecule of (a) or (b) wherein the variant comprises at most 1, 2, 3, 4, 5, 6, 7, 8, 9 mutations in the VH and/or VL polypeptide sequence, wherein the variant binds with specificity to DbpA antigen; preferably, the variant comprises at most 1, 2, or 3 mutations in one or more FR sequences of SEQ ID Nos: 13-18 or the FR sequences of SEQ ID Nos: 19-24, wherein the variant retains binding specificity to the DbpA antigen; or (d) a variant of the molecule of (a) or (b) wherein the variant comprises at least 80%, at least 85%, at least 90%, at least 95%, or at least 98% sequence identity to the VH and/or VL polypeptide sequences, wherein the variant binds with specificity to DbpA antigen; preferably, the variant comprises variations only in the FR sequences of SEQ ID Nos: 13-18 or the FR sequences of SEQ ID Nos: 19-24, e.g., a variation comprising at least 80%, at least 85%, at least 90%, at least 95%, or at least 98% sequence identity to a given FR sequence, wherein the variant retains binding specificity to the DbpA antigen.

In some embodiments, the engineered molecules of the disclosure may contain a peptide sequence, for example, an N-terminal signal sequence that guides the trafficking of the antibody or a fragment thereof to the extracellular milieu, plasma membrane (outer membrane, transmembrane, or inner membrane), or a specialized compartment in the cell, e.g., endosome, lysosome, ER, Golgi's apparatus, vacuoles, inclusion bodies, nucleolus, mitochondria, chloroplast, periplasm, etc. Preferably, the signal sequence comprises, consists essentially of, or consists of 6G8 signal sequence set forth in MGWSCIMLFLAATATGVHS (SEQ ID NO: 29) or MDMRAPAQFLGILLLWFPGARC (SEQ ID NO: 30) or 8C10 signal sequence set forth in MEWTWVFLFLLSVTAGVHS (SEQ ID NO: 31) or MESQIQAFVFVFLWLSGVDG (SEQ ID NO: 32). Other signal peptides, such as those disclosed in U.S. Pat. No. 7,807,409, may also be used.

The disclosure therefore relates to molecules comprising signal peptides (e.g., SEQ ID NOs: 29-32), that are conjugated to the N-termini of antigen-binding sequences comprising a variable heavy chain (VH) and/or a variable light chain (VL) domain, wherein the VH comprises $FR_{H1}$-$CDR_{H1}$-$FR_{H2}$-$CDR_{H2}$-$FR_{H3}$-$CDR_{H3}$ and/or VL comprises $FR_{L1}$-$CDR_{L1}$-$FR_{L2}$-$CDR_{L2}$-$FR_{L3}$-$CDR_{L3}$, wherein $FR_{1-3}$, in each VH or VL chain, represent antibody framework regions and $CDR_{1-3}$, in each VH or VL chain, represent antibody complementary determining regions, wherein the meanings of each FR and each CDR have been provided above.

The disclosure further relates to antibodies comprising secondary antibody regions and domains. Such may include, e.g., constant domains, hinge regions, including antibody portions comprising a plurality of such domains (e.g., constant portion comprising two or more constant domains). Whereas the variable domains of each pair of light and heavy chains are the specific ligand binding domains of the antibody, other molecules, known as effector molecules or cells, bind to other sites in the remainder of the antibody molecule, i.e., other than the antigen binding sites. Due to their relatively invariant nature, as compared to the binding domain sequences, these domains are generally referred as "secondary regions" of an antibody, such regions being located particularly in the Fc region constituted by the portions of the heavy chains extending beyond the ends of the light chains.

The addition, removal or modification of the constant regions of the antibody is known to play a particularly important role in the bioavailability, distribution, and half-life of therapeutically administered antibodies. The antibody class and subclass, encoded by the Fc or constant region of the antibody, when present, imparts important additional properties. Thus, DbpA binding antibodies with reconfigured, redesigned, or otherwise altered constant domains are encompassed by the anti-DbpA antibody compositions of the disclosure.

Generally, the effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis (Ward et al., *Therapeutic Immunology*, 2:77-94, 1995). Cellular responses depend on activation by binding of antibody-antigen complexes and by downstream sequences caused by the release of cell mediators as a result of Ab-Ag complex binding to effector cells. These cellular responses include neutralization of target, opsonization and sensitization (if antigen is displayed on the surface of a cell, such as in the case of DbpA), sensitization of mast cells, and activation of complement. For cellular targets (e.g., cell antigens) the effector functions include antibody directed cellular cytotoxicity (ADCC) or complement-mediated cytotoxicity (CDC).

In some embodiments, the disclosure relates to antibodies comprising an entire heavy and/or an entire light chain of MAb 6G8, the sequences of which comprise, consist essentially of, or consist of the polypeptide sequences of SEQ ID NO: 33 (6G8 γ chain) and/or SEQ ID NO: 34 (6G8 κ chain) or a variant comprises at least 80%, at least 85%, at least 90%, at least 95%, or at least 98% sequence identity to SEQ ID NO: 33 and/or SEQ ID NO: 34, wherein the amino acids at positions 1-19 of SEQ ID NO: 33 and at positions 1-22 of SEQ ID NO: 34 make up the signal peptide, which are optionally cleaved (in a mature protein):

(SEQ ID NO: 33)
MGWSCIMLFLAATATGVHSQVQLQQPGAELVKPGASVKLSCKASGYTFT

RYWMYWVKQRPGRGLEWIGRLDPNSGVTKYNEKFKSKATLTVDKSSSTA

YMQLSSLTSEDSAVYYCVRDDSWYFDVWGTGTTVTVSSAKTTPPSVYPL

APGSAAQTNSMVTLGCLVKGYFPEPVTVTWNSGSLSSGVHTFPAVLQSD

LYTLSSSVTVPSSTWPSQTVTCNVAHPASSTKVDKKIVPRDCGCKPCIC

TVPEVSSVFIFPPKPKDVLTITLTPKVTCVVVDISKDDPEVQFSWFVDD

VEVHTAQTKPREEQINSTFRSVSELPIMHQDWLNGKEFKCRVNSAAFPA

PIEKTISKTKGRPKAPQVYTIVYSKLNVQKSNWEAGNTFTCSVLHEGLH

NHHTEKSLSLSPGK (SEQ ID NO: 34)
MDMRAPAQFLGILLLWFPGARCEIQMTQSPSSMSASLGDRITITCQATQ

DIVKNLNWYQQKPGKPPSFLIYYATELAEGVPSRFSGSGSGSDYSLTIN

NLESQDFADYFCLQFYAFPLTFGAGTKLELRRADAAPTVSIFPPSSEQL

TSGGASVVCFLNNFYPRDINVKWKIDGSERQNGVLNSWTDQDSKDSTYS

MSSTLT LTKDEYERHNSYTCEATHKTSTSPIVKSFNRGEC

In some embodiments, the disclosure relates to antibodies comprising an entire heavy and/or an entire light chain of MAb 8C10, the sequences of which comprise, consist essentially of, or consist of the polypeptide sequences of SEQ ID NO: 35 (8C10 γ chain) and/or SEQ ID NO: 36 (8C10 κ chain) or a variant comprises at least 80%, at least 85%, at least 90%, at least 95%, or at least 98% sequence identity to SEQ ID NO: 35 and/or SEQ ID NO: 36 (note: the amino acids at positions 1-19 of SEQ ID NO: 35 and at positions 1-20 of SEQ ID NO: 36 make up the signal peptide, which may be cleaved in the mature protein):

(SEQ ID NO: 35)
MEWTWVFLFLLSVTAGVHSQVQLQQSGAELMKPGASVKLSCKAAGYTFT

DYWIEWVKQRPGHGLEWIGEILPGSGSTKDNERFKGKATFTADTSSNTA

YMQLSSLTTEDSAIYYCARREWGYYFDYWGQGTTLTVSSAKTTPPSVYP

LAPGSAAQTNSMVTLGCLVKGYFPEPVTVTWNSGSLSSGVHTFPAVLQS

DLYTLSSSVTVPSSTWPSQTVTCNVAHPASSTKVDKKIVPRDCGCKPCI

CTVPEVSSVFIFPPKPKDVLTITLTPKVTCVVVDISKDDPEVQFSWFVD

DVEVHTAQTKPREEQINSTFRSVSELPIMHQDWLNGKEFKCRVNSAAFP

APIEKTISKTKGRPKAPQVYTIPPPKEQMAKDKVSLTCMITNFFPEDIT

VEWQWNGQPAENYKNTQPIMDTDGSYFVYSKLNVQKSNWEAGNTFTCSV

LHEGLHNHHTEKSLSLSPGK (SEQ ID NO: 36)
MESQIQAFVFVFLWLSGVDGDIVMTQSHKFMSTSVGDRVSITCKASQDV

STAVAWYQQKPGQSPKLLIYWASTRHTGVPDRFTGSGSGTDYTLTISSV

QAEDLALYYCQQHYSTPYTFGGGTKLEIKRADAAPTVSIFPPSSEQLTS

GGASVVCFLNNFYPRDINVKWKIDGSERQNGVLNSWTDQDSKDSTYSMS

STLTLTKDEYERHNSYTCEATHKTSTSPIVKSFNRGEC

Other than the above-illustrated representative isotype of immunoglobulin G, the disclosure includes other types of immunoglobulin isotypes, e.g., any of the five major classes or isotypes selected from IgA, IgD, IgE, IgG and IgM, including subclasses (subtypes) thereof, e.g. IgG1, IgG2, IgG3, and IgG4; IgA1, IgA2, and IgAsec. The light chains of the antibodies usually are of two classes (K and X) and the heavy chain constant regions correspond to the different classes of immunoglobulins, vis-á-vis α, δ, ε, γ, and μ for IgA, IgD, IgE, IgG and IgM, respectively. Of the various human immunoglobulin classes, only human IgG, IgG2, IgG3 and IgM are known to activate complement; and human IgG and IgG3 mediate ADCC more effectively than IgG2 and IgG4. The antibodies of the disclosure may include chimeric or humanized forms of the MAb 6G8 or MAb 8C10 in a variety of human antibody isotypes and subtypes, such as, IgG K, IgG2, IgG4, IgM, and IgA1.

Preferably, the antibody is an IgM antibody. As is recognized in immunology, the IgM class of antibodies recognizes a large variety of pathogenic antigens and is highly active in cytotoxic and cytolytic reactions due to its superior activation of the complement system. IgM antibody is useful in antibody drug discovery. IgM antibody demonstrates strong avidity as well as complement fixation property against bacterial antigens. For certain targets, particularly those such as glycol-epitopes on bacterial proteins, an IgM antibody is particularly useful.

The disclosure accordingly provides for IgM antibodies comprising an Ig t chain C region. Preferably, the IgM antibody comprises, consists essentially of, or consists of, the Ig t chain C region SEQ ID NO: 37 (see PIR: S37768; GI: 7439150; last revised: Mar. 10, 2005) or a fragment thereof or a variant thereof:

(SEQ ID NO: 37)
GSASAPTLFPLVSCENSPSDTSSVAVGCLAQDFLPDSITFSWKYKNNSD

*ISSTRGFPSVLRGGKYAATSQVLLPSKDVMQGTDEHVVCKVQHPNGNKE*

*KNVPLPVIAELPPKVSVFVPPRDGFFGNPRKSKLI*CQATGFSPRQIQVS

WLREGKQVGSGVTTDQVQAEAKESGPTTYKVTSTLTIKESDWLSQSMFT

CRVDHRGLTFQQNASSMCVPDQDTAIRVFAIPPSFASIFLTKSTKLTCL

VTDLTTYDSVTISWTRQNGEAVKTHTNISESHPNATFSAVGEASICEDD

WNSGERFTCTVTHTDLPSPLKQTISRPKGVALHRPDVYLLPPAREQLNL

RESATITCLVTGFSPADVFVQWMQRGQPLSPEKYVTSAPMPEPQAPGRY

FAHSILTVSEEEWNTGETYTCVVAHEALPNRVTERTVDKSTGKPTLYNV

SLVMSDTAGTCY

Fragments of Ig Ct chain C region preferably comprise deletion of the first constant Ig domain of the heavy chain, e.g., a deletion of aa1-102 of SEQ ID NO: 37.

Variants of the Ig Ct chain C region (SEQ ID NO: 37) include, polypeptides comprising at least 80%, at least 85%, at least 90%, at least 95%, or at least 98% sequence identity to SEQ ID NO: 37. Non-limiting examples of such variants include, polypeptides having the following accession numbers: UNIPROT #P01871 (last revised: Mar. 28, 2018), GENBANK #CAB37838 (last revised: Jul. 25, 2016) and GENBANK #CAC20458 (last revised: Jul. 14, 2016), all of which comprise >95% sequence identity to SEQ ID NO: 37, including fragments thereof (e.g., comprising, deletion of the first constant Ig domain of the heavy chain).

The disclosure further relates to chimeric proteins wherein the constant portion of an immunoglobulin (e.g., IgG) is replaced by a constant portion of a different immunoglobulin isotype (e.g., IgA, IgD, IgE, or IgM; preferably IgM). Accordingly, in some embodiments, the disclosure provides for a chimeric antibody comprising a variable (Fv) region of a first antibody (e.g., IgG) fused to constant regions (C1, optionally together with C2 and/or C3) of a second antibody (e.g., IgA, IgD, IgE, or IgM; preferably IgM) or a chimeric antibody comprising a fragment antigen-binding (Fab) region of a first antibody (e.g., IgG) fused to constant regions (C2 and/or C3) of a second antibody (e.g., IgA, IgD, IgE, or IgM; preferably IgM). Preferably, the constant regions comprise all or a substantial portion of the crystallizable region (Fc) of the second antibody. Without being bound to particular embodiments, the disclosure includes a 6G8 chimeric IgM (SEQ ID NO: 38) and 8C10 chimeric IgM (SEQ ID NO: 39), wherein for SEQ ID NO: 38, the IgG sequences correspond to amino acid residues 1-214 and the remainder are IgM sequences.

(SEQ ID NO: 38)
QVQLQQPGAELVKPGASVKLSCKASGYTFTRYWMYWVKQRPGRGLEWIG

RLDPNSGVTKYNEKFKSKATLTVDKSSSTAYMQLSSLTSEDSAVYYCVR

DDSWYFDVWGTGTTVTVSSAKTTPPSVYPLAPGSAAQTNSMVTLGCLVK

GYFPEPVTVTWNSGSLSSGVHTFPAVLQSDLYTLSSSVTVPSSTWPSQT

VTCNVAHPASSTKVDKKILPVIAELPPKVSVFVPPRDGFFGNPRKSKLI

CQATGFSPRQIQVSWLREGKQVGSGVTTDQVQAEAKESGPTTYKVTSTL

TIKESDWLSQSMFTCRVDHRGLTFQQNASSMCVPDQDTAIRVFAIPPSF

ASIFLTKSTKLTCLVTDLTTYDSVTISWTRQNGEAVKTHTNISESHPNA

TFSAVGEASICEDDWNSGERFTCTVTHTDLPSPLKQTISRPKGVALHRP

DVYLLPPAREQLNLRESATITCLVTGFSPADVFVQWMQRGQPLSPEKYV

TSAPMPEPQAPGRYFAHSILTVSEEEWNTGETYTCVVAHEALPNRVTER

TVDKSTGKPTLYNVSLVMSDTAGTCY (SEQ ID NO: 39)
QVQLQQSGAELMKPGASVKLSCKAAGYTFTDYWIEWVKQRPGHGLEWIG

EILPGSGSTKDNERFKGKATFTADTSSNTAYMQLSSLTTEDSAIYYCAR

REWGYYFDYWGQGTTLTVSSAKTTPPSVYPLAPGSAAQTNSMVTLGCLV

KGYFPEPVTVTWNSGSLSSGVHTFPAVLQSDLYTLSSSVTVPSSTWPSQ

TVTCNVAHPASSTKVDKKILPVIAELPPKVSVFVPPRDGFFGNPRKSKL

ICQATGFSPRQIQVSWLREGKQVGSGVTTDQVQAEAKESGPTTYKVTST

LTIKESDWLSQSMFTCRVDHRGLTFQQNASSMCVPDQDTAIRVFAIPPS

FASIFLTKSTKLTCLVTDLTTYDSVTISWTRQNGEAVKTHTNISESHPN

ATFSAVGEASICEDDWNSGERFTCTVTHTDLPSPLKQTISRPKGVALHR

PDVYLLPPAREQLNLRESATITCLVTGFSPADVFVQWMQRGQPLSPEKY

VTSAPMPEPQAPGRYFAHSILTVSEEEWNTGETYTCVVAHEALPNRVTE

RTVDKSTGKPTLYNVSLVMSDTAGTCY.

The disclosure further provides a method for preparing an anti-DbpA antibody comprising: preparing an antibody comprising (1) human heavy chain framework regions and human heavy chain CDRs, wherein at least one of the human heavy chain CDRs comprises an amino acid sequence selected from the amino acid sequences of CDRs shown in SEQ ID NOs: 1-3; and (2) human light chain framework regions and human light chain CDRs, wherein at least one of the human heavy chain CDRs comprises an amino acid-sequence selected from the amino acid sequences of CDRs shown in SEQ ID NOs: 4-6; wherein the antibody retains the ability to bind to DbpA. The ability of the antibody to bind DbpA can be determined using standard binding assays, such as those set forth in the Examples (e.g., using BIACORE or an ELISA).

Alternately, in the context of 8C10 antibody or antigen-binding fragments thereof, the disclosure further provides a method for preparing an anti-DbpA antibody comprising: preparing an antibody comprising (1) human heavy chain framework regions and human heavy chain CDRs, wherein at least one of the human heavy chain CDRs comprises an amino acid sequence selected from the amino acid sequences of CDRs shown in SEQ ID NOs: 7-9; and (2) human light chain framework regions and human light chain CDRs, wherein at least one of the human heavy chain CDRs comprises an amino acid-sequence selected from the amino acid sequences of CDRs shown in SEQ ID NOs: 10-12; wherein the antibody retains the ability to bind to DbpA. The ability of the antibody to bind DbpA can be determined using standard binding assays, such as those set forth in the Examples (e.g., using BIACORE or an ELISA).

The antibodies of the disclosure can bind DbpA fragment of SEQ ID NO: 77 with a wide range of affinities ($K_D$). In a preferred embodiment, at least one mAb of the present disclosure can optionally bind DbpA subunit with high affinity. For example, a human mAb can bind DbpA with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ M or any range or value therein.

The affinity or avidity of an antibody of the disclosure for an antigen such as DbpA fragment of SEQ ID NO: 77 can be determined experimentally using any suitable method. Representative methods are described in, Berzofsky et al. In: *Fundamental Immunology*, Paul et al., Ed., Raven Press: New York, N.Y. (1984); Kuby et al., In: *Immunology*, W. H. Freeman and Company, New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $IC_{50}$) are preferably made with standardized solutions of antibody and antigen, and a standardized buffer, such as the buffer described herein.

In some embodiments, the antibody or antigen-binding fragment of the disclosure binds DbpA and, thereby partially or substantially sequesters the protein. An antibody, or specified portion or variant thereof, that partially or preferably substantially sequesters about 10%-99%, preferably at least about 10%, 20%, 30%, 40%, 50%, 55%, 60%, 65%, 70%, 75%, 80%, 85%, 90%, 95%, 99%, or more, e.g., 100% depending on the levels of the proteins and the conditions surrounding interaction between the antibody and the DbpA antigen. In some embodiments, the antibodies of the disclosure inhibit at least one biological activity of DbpA.

As previously stated, the disclosure also relates to antibodies, antigen-binding fragments, immunoglobulin chains and CDRs comprising amino acids in a sequence that is substantially the same as an amino acid sequence described herein. Preferably, such antibodies bind DbpA with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. In some embodiments, the anti-DbpA antibody of the present disclosure, including antigen-binding fragments thereof, chimeras thereof, or humanized forms thereof, as described above, can include one or more amino acid substitutions, deletions or additions, either from natural mutations or human manipulation, as specified herein.

Amino acids in an anti-DbpA antibody of the present disclosure that are important for function, e.g., DbpA binding, can be identified by methods known in the art, such as site-directed mutagenesis or alanine-scanning mutagenesis (e.g., Ausubel, *Current Protocols* (2002), Chapters 8, 15, supra; Cunningham et al., *Science* 244:1081-1085, 1989). Cunningham's procedure introduces single alanine mutations at every residue in the molecule. The resulting mutant molecules are then tested for biological activity, such as, but not limited to at least one DbpA binding activity. Sites that are important for antibody binding can also be identified by structural analysis such as crystallization, nuclear magnetic resonance or photo affinity labeling (Smith et al., *J. Mol. Biol.*, 224:899-904, 1992 and de Vos et al., *Science* 255: 306-312, 1992).

As those of skill will appreciate, the present disclosure includes at least one biologically active antibody of the present disclosure. Biologically active antibodies have a specific activity at least 20%, 30%, or 40%, and preferably at least 50%, 60%, or 70%, and most preferably at least 80%, 90%, or 95%-100% of that of the parent antibody, MAb 6G8 or MAb 8C10. Methods of assaying and quantifying measures of activity and antigen specificity are well known to immunologists.

The disclosure especially relates to antigen-binding fragments of the antibodies, e.g., Fab, F(ab')2, Fv and scFv. The Fab fragment of an antibody, which is about one-third the size of a complete antibody contains the heavy and light chain variable regions, the complete light chain constant region and a portion of the heavy chain constant region. Fab molecules are stable and associate well due to the contribution of the constant region sequences. They can be generated via papain digestion of a complete antibody or recombinantly. F(ab')2 comprise two antigen binding sites and are generated from complete antibodies using pepsin or *Streptococcus pyogenes* immunoglobulin degrading enzyme (IDES), However, functional Fab or F(ab')2 expressed in bacterial systems is lower than that of the smaller Fv fragment which contains only the variable regions of the heavy and light chains. The Fv fragment is the smallest portion of an antibody that still retains a functional antigen binding site. The Fv fragment has the same binding properties as the Fab, however without the stability conferred by the constant regions, the two chains of the Fv can dissociate relatively easily in dilute conditions. To prevent such dissociations, VH and VL regions of Fv can be fused via a polypeptide linker (Huston et al., *PNAS USA*, 85 (16) 5879-5883, 1988) to stabilize the antigen binding site. This single polypeptide Fv fragment is known as a single chain antibody (scFv). See WO; U.S. Pat. Nos. 5,534,254; 5,571,894; and 5,587,458. Fv and sFv comprising intact combining sites, that is VH and VL domains that are devoid of constant regions, can also be generated. The VH and VL in Fv, sFv and scFv can be arranged with either domain first. The linker joins the carboxy terminus of the first chain to the amino terminus of the second chain.

The disclosure further relates to antibodies comprising single domain antibodies (sdAb). Versatile methods for generating rabbit variable domain of heavy chain (rVH) derived sdAbs with high affinities ($K_D$<1 nM) and enhanced thermal stabilities are known in the art. See, Shinozaki et al., Sci. Rep., 7(1):5794, 2017; Hussack et al., PLoS One, 6(11), e28218, 2011. A variety of sdAbs, including those with high affinities, can be efficiently acquired using an rVH-displaying phage library.

One of skill in the art will recognize that antibody fragments may be made and used in accordance with the disclosure. For instance, heavy or light chains in antibody fragments can be mutagenized using site directed mutagenesis. The two chains can be combined to form a functional antibody fragment. Random non-specific light or heavy chain sequences may be added using a combinatorial system to generate a library of diverse members, which are tested for functionality, e.g., DbpA binding (more specifically binding to DbpA fragment of SEQ ID NO: 77) using routine methods, e.g., a high throughput method based on BIA-CORE screening.

Generation of Anti-DbpA Antibodies

Anti-DbpA antibodies of the present disclosure can be optionally produced by a variety of techniques, including the standard somatic cell hybridization technique (hybridoma method) of Kohler et al., Nature 256:495, 1975. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding et al., Monoclonal Antibodies: Principles and Practice., pp. 59-103 (Academic Press, 1986)).

The anti-DbpA antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-DbpA antibody can be isolated from such animals and immortalized using suitable methods, such as the methods described herein.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (See, Lonberg et al., Nature, 368, 856-9, 1994; Green et al., Nature Genet., 7, 13-21, 1994; Green et al., Exp. Med., 188:483-95, 1988; Lonberg et al., Int. Rev. Immunol., 13:65-93, 1995; Bruggemann et al., Eur. J. Immunol., 21, 1323-1326, 1991; Fishwild et al., Nat. Biotechnol., 14:845-851, 1996; Mendez et al., Nat. Genet., 15:146-156, 1997; Green et al., J. Immunol. Methods 231:11-23, 1999; Yang et al., Cancer Res. 59:1236-1243, 1999; Brüggemann et al., Curr. Opin. Biotechnol. 8:455-458, 1997; and U.S. Pat. Nos. 5,569,825; 6,300,129; 6,713,610; 7,041,870). The endogenous immunoglobulin loci in such mice can be disrupted or deleted to eliminate the capacity of the animal to produce antibodies encoded by endogenous genes. In addition, companies such as Codexis, Inc. (Redwood City, Calif., USA) and Creative Biolabs, Inc. (Shirley, N.Y., USA) can be engaged to provide human antibodies directed against a selected antigen using technology as described above.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

Immunization with antigen can be optionally accompanied by addition of an adjuvant, such as complete Freund's adjuvant. The immune response can be monitored over the course of the immunization protocol with plasma samples being obtained by retroorbital bleeds. The plasma can be screened by ELISA (as described below), and mice with sufficient titers of anti-DbpA immunoglobulin can be used for fusions. Mice can be boosted intravenously with antigen 3 days before sacrifice and removal of the spleen. In some embodiments, plurality (e.g., 2, 3, 4 or more) of antigen fusions may be performed. Several mice may be immunized for each antigen.

To generate hybridomas producing monoclonal antibodies to DbpA, splenocytes and lymph node cells from immunized mice can be isolated and fused to an appropriate immortalized cell line, such as a mouse myeloma cell line. The resulting hybridomas can be screened for the production of antigen-specific antibodies.

A suitable immortal cell line incapable of producing immunoglobulin chains is selected as a fusion partner, e.g., a myeloma cell line such as, but not limited to, Sp2/0 and derivative cell lines, NS1 and derivatives, especially NSO engineered NSO lines such as GS-NSO, AE-1, L.5, P3X63Ag8.653, U937, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/0 or the like, or hetero-myelomas, fusion products thereof, or any cell or fusion cell derived therefrom, or any other suitable cell line as known in the art (Birch et al., Biologics 22:127-133, 1994). The fused cells (hybridomas) or recombinant cells can be isolated using selective culture conditions or other suitable known methods, and cloned by limiting dilution or cell sorting, or other known methods. Cells which produce antibodies with the desired specificity can be detected by a suitable assay (e.g., ELISA) and selected for manipulation.

Other suitable methods of generating or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MORPHO-SYS, Martinsreid, Germany; Biovation, Aberdeen, Scotland, UK; Biolnvent, Lund, Sweden; Dyax Corp., Enzon, Affymax/Biosite; Xoma, Berkeley, Calif., USA. See, e.g., U.S. Pat. Nos. 5,885,793; 5,969,108; 5,994,519; 6,017,732; 6,248,516; or stochastically generated peptides or proteins (U.S. Pat. Nos. 5,723,323; 5,763,192; 5,814,476; 5,817,483; 5,824,514; 5,976,862) that are capable of producing a repertoire of human antibodies, as known in the art and/or as described herein. Such techniques, include, but are not limited to, ribosome display (Hanes et al., PNAS USA, 94:4937-4942, 1997); Hanes et al., PNAS USA, 95:14130-1413, 1998); single cell antibody producing technologies (e.g., selected lymphocyte antibody method ("SLAM") (U.S. Pat. No. 5,627,052; Wen et al., J. Immunol., 17:887-892, 1987; Babcook et al., PNAS USA, 93:7843-7848, 1996); gel microdroplet and flow cytometry (Powell et al., Biotechnol., 8:333-337, 1990; One Cell Systems, Cambridge, Mass., USA; Gray et al., J. Imm. Meth., 182:155-163, 1995; Kenny et al., Bio Technol., 13:787-790, 1995);

B-cell selection (Steenbakkers et al., *Molec. Biol. Reports,* 19:125-134, 1994; Jonak et al., *Progress Biotech.,* Vol. 5, In vitro Immunization in Hybridoma Technology, Borrebaeck, ed., Elsevier, Amsterdam, Netherlands, 1988).

Screening antibodies for specific binding to similar proteins or fragments can also be conveniently achieved using peptide display libraries. This method involves the screening of large collections of peptides for individual members having the desired function or structure.

Antibody screening using peptide display libraries is well known in the art. The displayed peptide sequences can be from 3 to 5000 or more amino acids in length, frequently from 5-100 amino acids long, and often from about 8 to 25 amino acids long. Peptide display libraries, vector, and screening kits are commercially available from such suppliers as Invitrogen (Carlsbad, Calif., USA), and Cambridge Antibody Technologies (Cambridgeshire, UK). See, U.S. Pat. No. 5,885,793. See also, e.g., Enzon patents (U.S. Pat. Nos. 4,704,692; 4,939,666; 4,946,778; 5,260,203; 5,455,030; 5,518,889; 5,534,621; 5,656,730; 5,763,733; 5,767,260; and 5,856,456); Dyax patents (U.S. Pat. Nos. 5,223,409; 5,403,484; 5,571,698; and 5,837,500); Affymax patents (U.S. Pat. Nos. 5,427,908; 5,580,717); Genentech patents (U.S. Pat. No. 5,750,373); and Xoma patents (U.S. Pat. Nos. 5,618,920; 5,595,898; 5,576,195; 5,698,435; and 5,693,493; 5,698,417).

Antibody Fragments

Antibody fragments can be derived via proteolytic digestion of intact antibodies (see, e.g., Morimoto et al., *J Biochem Biophys Methods,* 24:107-117, 1992; and Brennan et al., Science, 229:81, 1985). However, these fragments can now be produced directly by recombinant host cells. F(ab')2, Fab, Fv and ScFv antibody fragments can all be expressed in and secreted from mammalian host cells or from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., *BioTechnology* 10:163-167, 1992).

Preferably, recombinant production of antibody fragments is carried out using a single-chain expression polynucleotide. This expression polynucleotide contains: (1) a single-chain antibody cassette consisting of a VH domain, spacer peptide, and VL domain operably linked to encode a single-chain antibody, (2) a promoter suitable for in vitro transcription (e.g., T7 promoter, SP6 promoter, and the like) operably linked to ensure in vitro transcription of the single-chain antibody cassette forming a mRNA encoding a single-chain antibody, and (3) a transcription termination sequence suitable for functioning in an in vitro transcription reaction. Optionally, the expression polynucleotide may also comprise an origin of replication and/or a selectable marker. An example of a suitable expression polynucleotide is pLM166. To obtain VH and VL sequences for cloning, a library of VH and VL sequences produced by PCR amplification using V gene family-specific primers or V gene-specific primers may be used (Nicholls et al., *J. Immunol. Meth.,* 165: 81, 1993; WO 1993/12227) or are designed according to standard art-known methods based on available sequence information. Typically, mouse or human VH and VL sequences are isolated. The VH and VL sequences are then ligated, usually with an intervening spacer sequence (e.g., encoding an in-frame flexible peptide spacer), forming a cassette encoding a single-chain antibody. Typically, a library comprising a plurality of VH and VL sequences is used (sometimes also with a plurality of spacer peptide species represented), wherein the library is constructed with one or more of the VH and VL sequences mutated to increase sequence diversity particularly at CDR residues, sometimes at framework residues. V region sequences can be conveniently cloned as cDNAs or PCR amplification products for immunoglobulin-expressing cells. For example, cells from human hybridoma, or lymphoma, or other cell line that synthesizes either cell surface or secreted immunoglobulin may be used for the isolation of polyA+RNA. The RNA is then used for the synthesis of oligo dT primed cDNA using the enzyme reverse transcriptase (see, Goodspeed et al., *Gene,* 76: 1, 1989; Dunn et al., *J. Biol. Chem.,* 264: 13057, 1989). Once the V-region cDNA or PCR product is isolated, it is cloned into a vector to form a single-chain antibody cassette.

In some embodiments, the antibodies of the disclosure or antigen-binding fragments thereof may be prepared by in vitro (e.g., cell-free) synthesis, using conventional methods as known in the art. Various synthetic apparatuses are available, e.g., automated synthesizers by Applied Biosystems, Inc., Foster City, Calif., USA. By using synthesizers, naturally occurring amino acids may be substituted with unnatural amino acids. The particular sequence and the manner of preparation will be determined by convenience, economics, purity required, and the like.

Nucleic Acid Molecules

The disclosure further relates to nucleic acids which encode the antigens of the disclosure or antibodies or antigen-binding fragments thereof which bind to the antigens.

In some embodiments, the disclosure relates to nucleic acid sequences that encode the CDRs of MAb 6G8 comprising, consisting essentially of, or consisting of SEQ ID Nos: 1-6 or variants thereof comprising at least 80%, 90%, or 95% sequence identity to SEQ ID Nos: 1-6. Preferably, the nucleic acid sequences comprise MAb 6G8 $CDR_{H1}$ encoding sequence AGG TACTGGATGT AC (SEQ ID NO: 40); CDRH2 encoding sequence AGGCTT GATCCTAATA GTGGTGTTAC TAAATACAAT GAGAAGTTCA AGAGC (SEQ ID NO: 41); CDRH3 encoding sequence GATGATTCC TGGTACTTCG ATGTC (SEQ ID NO: 42); $CDR_{L1}$ encoding sequence CAGGC AACTCAAGAC ATTGTTAAGA ATTTAAAC (SEQ ID NO: 43); CDRu encoding sequence TATGCAA CTGAACTGGC AGAA (SEQ ID NO: 44); and $CDR_{L3}$ encoding sequence CTA-CAGTTTT ATGCGTTTCC GCTCACG (SEQ ID NO: 45). The disclosure further relates to polynucleotides that comprise at least 80%, 90%, or 95% sequence identity to SEQ ID Nos: 40-45, complements thereof, RNA equivalents thereof, or degenerates thereof.

In some embodiments, the disclosure relates to nucleic acid sequences that encode the CDRs of MAb 8C10 comprising, consisting essentially of, or consisting of SEQ ID Nos: 7-12 or variants thereof comprising at least 80%, 90%, or 95% sequence identity to SEQ ID Nos: 7-12. Preferably, the nucleic acid sequences comprise MAb 8C10 $CDR_{H1}$ encoding sequence GAC TACTGGATAG AG (SEQ ID NO: 46); $CDR_{H2}$ encoding sequence GAGATT TTACCTGGAA GTGGTAGTAC TAAGGACAAT GAGAGGTTCA AGGGC (SEQ ID NO: 47); $CDR_{H3}$ encoding sequence AGGGAGTGG GGCTACTACT TTGACTAC (SEQ ID NO: 48); $CDR_{L1}$ encoding sequence A AGGCCAGTCA GGATGTGAGT ACTGCTGTAG CC (SEQ ID NO: 49); $CDR_{L2}$ encoding sequence ATTTACTGG GCATCCACCC GGCACACT (SEQ ID NO: 50); and $CDR_{L3}$ encoding sequence CAGCAA CATTATAGCA CTCCGTACAC G (SEQ ID NO: 51). The disclosure further relates to polynucleotides that comprise at least 80%, 90%, or 95% sequence identity to SEQ ID Nos: 46-51, complements thereof, RNA equivalents thereof, or degenerates thereof.

In some embodiments, the disclosure relates to nucleic acid sequences that encode the FRs of MAb 6G8 comprising, consisting essentially of, or consisting of SEQ ID Nos: 13-18 or variants thereof comprising at least 80%, 90%, or 95% sequence identity to SEQ ID Nos: 13-18. Preferably, the nucleic acid sequences comprise MAb 6G8 $FR_{H1}$ encoding sequence CAG GTCCAACTGC AGCAGCCTGG GGCTGAGCTT GTGAAGCCTG GGGCTTCAGT GAAGCTGTCC TGCAAGGCTT CTGGCTACAC TTTCACT (SEQ ID NO: 52); $FR_{H2}$ encoding sequence TGGGTGAA ACAGAGGCCT GGACGAGGCC TTGAGTGGAT TGGA (SEQ ID NO: 53); $FR_{H3}$ encoding sequence AAGGC CACTCTGACT GTAGACAAAT CCTCCAGCAC AGCCTACATG CAGCTCAGCA GCCTGACATC TGAGGACTCT GCGGTCTATT ATTGTGTAAG GGATGATTCC (SEQ ID NO: 54); $FR_{L1}$ encoding sequence GAAA TCCAGATGAC CCAGTCTCCA TCCTCTATGT CTGCATCTCT GGGAGACAGA ATAACCATCA CTTGC (SEQ ID NO: 55); $FR_{L2}$ encoding sequence TG GTATCAGCAG AAACCAGGGA AACCCCCTTC ATTCCTGATC TAT (SEQ ID NO: 56); and $FR_{L3}$ encoding sequence AGGGGT CCATCAAGGT TCAGTGGCAG TGGGTCTGGG TCAGACTATT CTCTGACAAT CAACAACCTG GAGTCTCAAG ATTTTGCAGA CTATTTCTGT (SEQ ID NO: 57). The disclosure further relates to polynucleotides that comprise at least 80%, 90%, or 95% sequence identity to SEQ ID Nos: 52-57, complements thereof, RNA equivalents thereof, or degenerates thereof.

In some embodiments, the disclosure relates to nucleic acid sequences that encode the FRs of MAb 8C10 comprising, consisting essentially of, or consisting of SEQ ID Nos: 19-24 or variants thereof comprising at least 80%, 90%, or 95% sequence identity to SEQ ID Nos: 19-24. Preferably, the nucleic acid sequences comprise MAb 6G8 $FR_{H1}$ encoding sequence CAG GTTCAGCTGC AGCAGTCTGG AGCTGAGCTG ATGAAGCCTG GGGCCTCAGT GAAGCTTTCC TGCAAGGCTG CTGGCTACAC ATTCACT (SEQ ID NO: 58); $FR_{H2}$ encoding sequence TGGGTAAAA ACAGAGGCCT GGACATGGCC TTGAGTGGAT TGGA (SEQ ID NO: 59); $FR_{H3}$ encoding sequence AAGGC CACATTCACT GCAGATACAT CCTCCAACAC AGCCTACATG CAACTCAGCA GCCTGACAAC TGAGGACTCT GCCATCTATT ACTGTGCAAG G (SEQ ID NO: 60); $FR_{L1}$ encoding sequence GACATTGTGA TGACCCAGTC TCACAAATTC ATGTCCACAT CAGTAGGAGA CAGGGTCAGT ATCACCTGC (SEQ ID NO: 61); $FR_{L2}$ encoding sequence TGGTATCA ACAAAAACCA GGGCAATCTC CTAAACTACT GATTTAC (SEQ ID NO: 62); and $FR_{L3}$ encoding sequence GG AGTCCCTGAT CGCTTCACAG GCAGTGGATC TGGGACAGAT TATACTCTCA CCATCAGCAG TGTGCAGGCT GAAGACCTGG CACTTTATTA CTGT (SEQ ID NO: 63). The disclosure further relates to polynucleotides that comprise at least 80%, 90%, or 95% sequence identity to SEQ ID Nos: 58-63, complements thereof, RNA equivalents thereof, or degenerates thereof.

Preferably, the variant nucleic acids which encode CDRs of MAb 6G8 or MAb 8C10 do not contain mutations that would result in deletion, non-conservative substitutions, and/or change in positioning of the following amino acids: (1) $CDR_{H1}$: $^2$Y and/or $^3$W (relative to SEQ ID NO: 1); (2) $CDR_{H2}$: $^4$P, $^6$S, $^7$G, $^9$T, $^{10}$K, $^{12}$N, $^{13}$E, $^{16}$F and/or $^{17}$K (relative to SEQ ID NO: 2); (3) $CDR_{H3}$: $^6$F (relative to SEQ ID NO: 3); (4) $CDR_{L1}$: $^2$A, $^4$Q, and/or $^5$D (relative to SEQ ID NO: 4); (5) $CDR_{L2}$: $^1$Y (relative to SEQ ID NO: 5); and/or $CDR_{L3}$: $^2$Q, $^4$Y, $^7$P and/or $^9$T (relative to SEQ ID NO: 6).

In some embodiments, the disclosure relates to nucleic acids encoding molecules comprising antigen-binding sequences comprising a variable heavy chain (VH) and/or a variable light chain (VL) domain, wherein the VH comprises $FR_{H1}$-$CDR_{H1}$-$FR_{H2}$-$CDR_{H2}$-$FR_{H3}$-$CDR_{H3}$ and/or VL comprises $FR_{L1}$-$CDR_{L1}$-$FR_{L2}$-$CDR_{L2}$-$FR_{L3}$-$CDR_{L3}$, wherein $FR_{1-3}$, in each VH or VL chain, represent antibody framework regions; and wherein $CDR_{1-3}$, in each VH or VL chain, represent antibody complementary determining regions ("–" indicates a bond, preferably a peptide bond). Non-limiting examples of such molecules include, e.g., polypeptides comprising, consisting essentially of, or consisting of, the following amino acid sequences for VH and/or VL chains: (a) SEQ ID NOs: 25 and 26 or variants thereof comprising at least 80%, 90%, or 95% sequence identity to nucleic acids encoding SEQ ID Nos: 25 and/or 26; or (b) SEQ ID NOs: 27 and 28 or variants thereof comprising at least 80%, 90%, or 95% sequence identity to nucleic acids encoding SEQ ID Nos: 27 and/or 28.

The disclosure further includes nucleic acids encoding signal sequences comprising SEQ ID Nos: 29-32 or variants thereof. Such nucleic acids may be included or excluded from the 5' end of nucleic acids which encode CDRs and/or FRs.

In some embodiments, the disclosure relates to nucleic acids encoding an entire heavy and/or an entire light chain of MAb 6G8, which comprise, consist essentially of, or consist of the polynucleotide sequences of SEQ ID NO: 64 (6G8 γ chain) and/or SEQ ID NO: 65 (6G8 κ chain) or a variant comprises at least 80%, at least 85%, at least 90%, at least 91%, at least 92%, at least 93%, at least 94%, at least 95%, at least 96%, at least 97%, at least 98% or at least 99% sequence identity to SEQ ID NO: 64 and/or SEQ ID NO: 65 (note: bases 1-57 from SEQ ID NO: 64 or bases 1-66 from SEQ ID NO: 65 may be deleted as they encode signal peptides).

In some embodiments, the disclosure relates to nucleic acids encoding an entire heavy and/or an entire light chain of MAb 8C10, the sequences of which comprise, consist essentially of, or consist of the polynucleotide sequences of SEQ ID NO: 66 (8C10 γ chain) and/or SEQ ID NO: 67 (8C10 κ chain) or a variant comprises at least 80%, at least 85%, at least 90%, at least 91%, at least 92%, at least 93%, at least 94%, at least 95%, at least 96%, at least 97%, at least 98% or at least 99% sequence identity to SEQ ID NO: 66 and/or SEQ ID NO: 67 (note: bases 1-57 from SEQ ID NO: 66 or bases 1-60 from SEQ ID NO: 67 may be deleted as they encode signal peptides).

The disclosure further relates to antibody constructs comprising nucleic acids which encode an Ig μ chain C region. Preferably, the nucleic acid encodes a protein having the sequence SEQ ID NO: 37 or a fragment thereof or variant thereof, the protein accessioned in GENBANK under accession number PIR: S37768 or GI: 7439150. Nucleic acid fragments encoding fragments of Ig t chain C region preferably encode proteins which have partial or complete truncation of the first constant Ig domain of the heavy chain, e.g., a deletion of a part or whole of aa1-102 of SEQ ID NO: 37 (S37768). Variants of the Ig t chain C region (SEQ ID NO: 37) include, polypeptides comprising at least 80%, at least 85%, at least 90%, at least 95%, or at least 98% sequence identity to SEQ ID NO: 37. Non-limiting examples of such variants include, polypeptides having the following accession numbers: GENBANK #X57086 (last revised: Jul. 25, 2016) and GENBANK #AJ294734 (last revised: Jul. 14, 2016), including fragments thereof (e.g., comprising, deletion of the first constant Ig domain of the heavy chain).

The disclosure especially relates to nucleic acids which encode chimeric antibodies whose sequences are set forth in SEQ ID NO: 38 (6G8 chimeric IgM) or SEQ ID NO: 39 (8C10 chimeric IgM), including polynucleotides that comprise at least 80%, 90%, or 95% sequence identity to the chimeric antibody-encoding polynucleotides, complements thereof, RNA equivalents thereof, or degenerates thereof.

The nucleic acids of the present disclosure can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in Mullinax et al., *BioTechniques*, 12(6), 864-869, 1992; and Better et al., *Science*, 240, 1041-1043, 1988.

Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5, 256-262, 1993 and Plückthun et al., *Immunol. Revs.*, 130: 151-188, 1992.

Known methods of DNA or RNA amplification include, but are not limited to, polymerase chain reaction (PCR) and related amplification processes. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in U.S. Pat. No. 4,683,202. Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

The isolated nucleic acid compositions of this disclosure, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present disclosure are used to identify the desired sequence in a cDNA or genomic DNA library.

The isolation of RNA, and construction of cDNA and genomic libraries, is well known to those of ordinary skill in the art.

The nucleic acid molecules of the disclosure are nucleic acids encoding antibodies or antibody portions (e.g., VH, VL, CDR3) that bind to DbpA. Preferably, the nucleic acid molecules comprise constant portions of human IgG or IgM that are fused to mouse anti-DbpA VH and/or VL sequences.

In some embodiments, mutations can be introduced randomly along all or part of an anti-DbpA antibody coding sequence, such as by saturation mutagenesis or by recombination, and the resulting modified anti-DbpA antibodies can be screened for binding activity.

Accordingly, antibodies encoded by variants of the heavy and light CDR nucleotide sequences disclosed herein (e.g., SEQ ID NOs: 40-45 in the case of MAb 6G8 or SEQ ID NOs: 46-51 in the case of MAb 8C10) and optionally containing heavy and light chain FR nucleotide sequences disclosed herein (e.g., SEQ ID NOs: 52-57 in the case of MAb 6G8 or SEQ ID NOs: 58-63 in the case of MAb 8C10) include antibodies that are substantially similar sequences to that of the parent antibodies 6G8 and/or 8C10. In some embodiments, the variant nucleic acids comprising substantial homology to the nucleic acids encoding 6G8 and/or 8C10 CDR and/or FR sequences. For nucleic acids, the term "substantial homology" indicates that two nucleic acids, or designated sequences thereof, when optimally aligned and compared, are identical, with appropriate nucleotide insertions or deletions, in at least about 80%, 90%, 95%, or have greater % identity, e.g., 98% to 99.5%, of the nucleotides. Alternatively, substantial homology exists when the sequences hybridize under selective hybridization conditions, to the complement of segments with the strand. The percent identity between two sequences is a function of the number of identical positions shared by the sequences (i.e., % homology=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdnaCMP matrix and a gap weight of 40, 50, 60, 70, or 80 and a length weight of 1, 2, 3, 4, 5, or 6. The percent identity between two nucleotide or amino acid sequences can also be determined using the algorithm of Meyers et al. (*Comput. AppL. Biosci.*, 4:11-17, 1988). The nucleic acid and protein sequences of the present disclosure can further be used as a "query sequence" to perform a search against public databases to, for example, identify related sequences. Such searches can be performed using the NBLAST and XBLAST programs of Altschul et al., *J. Mol. Biol.*, 215:403-10, 1990. BLAST nucleotide searches can be performed with the NBLAST program; Gapped BLAST can be utilized as described in Altschul et al., *Nucleic Acids Res.* 25(17):3389, 1997. Preferably, the default parameters of the respective programs (e.g., XBLAST and NBLAST) are used.

In some embodiments, the nucleic acids encoding the aforementioned antibodies or fragments thereof are obtained using computational methods, e.g., Reverse Translate Tool provided via Sequence Manipulation Suite under Bioinformatics(dot)Org. In some embodiments, the amino acid sequences encoded by the nucleic acids of the disclosure may be determined using a translate-tool program available via SBI's Expert Protein Analysis System (EXPASY). In another embodiment, the nucleic acids may be designed by ligating a fragment nucleic acid encoding the antigenic peptide to a plurality of nucleic acids encoding the linker and/or the carrier using routine recombinant DNA technology. Included herein are codon-optimized sequences of the aforementioned nucleic acid sequences and vectors. Codon optimization for expression in a host cell, e.g., bacteria such as E. coli or insect Hi5 cells or mammalian cells such as CHO cells, may be routinely performed using Codon Optimization Tool (CODONOPT), available from Integrated DNA Technologies, Inc., Coralville, Iowa The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. The nucleic acid compositions of the present disclosure, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated.

The disclosure further relates to nucleic acids that are in operable linkage to another nucleic acid sequence (e.g., the two nucleic acids are in a functional relationship with one another). For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Using the information provided herein, such as nucleotide sequences encoding at least 70-100% of the contiguous amino acids of at least one of SEQ ID NOs: 1-12 (CDR sequences) optionally together with nucleotide sequences encoding 70-100% of the contiguous amino acids of at least one of SEQ ID NOs: 13-18 (FR sequences), including fragments thereof, can be placed in operable linkage with another nucleic acid, e.g., an empty vector, using routine laboratory techniques and reagents.

Nucleic acid molecules of the present disclosure can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand. Furthermore, nucleic acid molecules of the present disclosure which comprise a nucleic acid encoding an anti-DbpA antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example-ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

The disclosure provides vectors, preferably, expression vectors, containing a nucleic acid encoding the anti-DbpA antibody, or may be used to obtain plasmids containing various antibody HC or LC genes or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. The present disclosure also relates to vectors that include isolated nucleic acid molecules of the present disclosure, host cells that are genetically engineered with the recombinant vectors, and the production of at least one anti-DbpA antibody by recombinant techniques, as is well known in the art.

For expression of the antibodies, or antibody fragments thereof, DNAs encoding partial or full-length light and heavy chains, can be inserted into expression cassettes or vectors such that the genes are operatively linked to transcriptional and translational control sequences. A cassette which encodes an antibody, can be assembled as a construct. A construct can be prepared using methods known in the art. The construct can be prepared as part of a larger plasmid. Such preparation allows the cloning and selection of the correct constructions in an efficient manner. The construct can be located between convenient restriction sites on the plasmid or other vector so that they can be easily isolated from the remaining plasmid sequences. The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (e.g., a signal peptide from a non-immunoglobulin protein).

Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

In general, a mammalian expression vector contains (1) regulatory elements, usually in the form of viral promoter or enhancer sequences and characterized by a broad host and tissue range; (2) a "polylinker" sequence, facilitating the insertion of a DNA fragment which comprises the antibody coding sequence within the plasmid vector; and (3) the sequences responsible for intron splicing and polyadenylation of mRNA transcripts. This contiguous region of the promoter-polylinker-polyadenylation site is commonly referred to as the transcription unit. The vector will likely also contain (4) a selectable marker gene(s) (e.g., the beta-lactamase gene), often conferring resistance to an antibiotic (such as ampicillin), allowing selection of initial positive transformants in E. coli; and (5) sequences facilitating the replication of the vector in both bacterial and mammalian hosts. A plasmid origin of replication are included for propagation of the expression construct in E. coli and for transient expression in Cos cells, the SV40 origin of replication is included in the expression plasmid. A promoter may be selected from a SV40 promoter, (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter. Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague et al., J. Virol. 45:773-781, 1983). Additionally, gene sequences to control replication in the host cell can be incorporated into the vector, as known in the art. Also, to avoid high surface expression of heavy chain molecules, it may be necessary to use an expression vector that eliminates transmembrane domain variant splices. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present disclosure include, for example, vectors such as pIRES lneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109).

Alternatively, the nucleic acids encoding the antibody sequence can be expressed in stable cell lines that contain the gene integrated into a chromosome. The co-transfection with a selectable marker such as DHFR, GPT, neomycin, or hygromycin allows the identification and isolation of the transfected cells which express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy et al., Biochem. J. 227: 277-279, 1991). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies. The DNA constructs used in the production of the antibodies of the disclosure can optionally include at least one insulator sequence. An insulator element is a control element which insulates the transcription of genes placed within its range of action but which does not perturb gene expression, either negatively or positively. Preferably, an insulator sequence is inserted on either side of the DNA sequence to be transcribed. For example, the insulator can be positioned about 200 bp to about 1 kb, 5' from the promoter, and at least about 1 kb to 5 kb from the promoter, at the 3' end of the gene of interest.

Examples of suitable inducible non-fusion E. coli expression vectors include pTrc and pET 11d. Examples of vectors for expression in yeast S. cerevisiae include pYepSec1, pMFa, pJRY88, pYES2, and pPicZ (Invitrogen Corp, San Diego, Calif., USA). Examples of baculovirus vectors available for expression of proteins in cultured insect cells (e.g., Sf 9 or Hi5 cells) include the pOET, pTriEx, pIEx, pBAC, pBacPAK, and the BD pVL and pAc families of vectors (Expression Systems LLC, Davis, Calif., USA).

In yet another embodiment, a nucleic acid of the disclosure is expressed in mammalian cells using a mammalian expression vector. Examples of mammalian expression vectors include pCDM8 (Seed et al., Nature, 329:840, 1987) and pMT2PC (Kaufman et al., EMBO J., 6:187-195, 1987). Preferably, the recombinant mammalian expression vector is capable of directing expression of the nucleic acid, preferentially in a particular cell type, such as lymphoma cells (e.g., mouse myeloma cells). In specific cell types, tissue-specific regulatory elements are used to express the nucleic acid. Tissue-specific regulatory elements are known in the art. Non-limiting examples of suitable tissue-specific promoters include the albumin promoter (liver-specific; Pinkert et al., Genes Dev., 1:268-277, 1987), lymphoid-specific promoters (Calame et al., Adv. Immunol., 43:235-275, 1988), in particular, promoters of T cell receptors (Winoto et al., EMBO J., 8:729-733, 1989) and immunoglobulins (Banerji et al., Cell, 33:729-740, 1983; Queen et al., Cell, 33:741-748, 1983), neuron-specific promoters (e.g., Byrne et al., PNAS USA, 86:5473-5477, 1989), pancreas-specific promoters (Edlund et al., Science, 230:912-916, 1985), and mammary gland-specific promoters (e.g., U.S. Pat. No. 4,873,316). Developmentally-regulated promoters are also encompassed, for example, by the murine hox promoters (Kessel et al., Science, 249:374-379, 1990) and the α-feto-protein promoter (Campes et al., Genes Dev., 3:537-546, 1989).

The disclosure further provides a recombinant expression vector comprising a DNA molecule cloned into the expression vector in an antisense orientation. That is, the DNA molecule is operably linked to a regulatory sequence in a manner that allows for expression (by transcription of the DNA molecule) of an RNA molecule that is antisense to the mRNA encoding a polypeptide. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. See Weintraub et al., *Reviews-Trends in Genetics,* 1, 1986).

In some embodiments, the nucleic acids encoding the antibodies of the disclosure are transfected in mouse myeloma cells (Looney et al. *Hum Antibodies Hybridomas,* 3(4):191-200, 1992), which attains production levels of >500 mg/L. For expression in CHO cells, plasmid pC4 containing the mouse DHFR gene under control of the SV40 early promoter, may be used. Cells lacking dihydrofolate activity that are transfected with these plasmids can be selected by growing the cells in a selective medium (e.g., α-MEM, Life Technologies, Gaithersburg, Md., USA) supplemented with the chemotherapeutic agent methotrexate. The amplification of the DHFR genes in cells resistant to methotrexate (MTX) has been well documented (Alt, et al., *J. Biol. Chem.,* 253:1357-1370, 1978). This approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell, which can then be selected.

Mammalian cells such as CHO cells, myeloma cells, HEK293 cells, BHK cells (BHK21, ATCC CRL-10), mouse Ltk-cells, and NIH3T3 cells have been frequently used for stable expression of heterologous genes. In contrast, cell lines such as Cos (COS-1 ATCC CRL 1650; COS-7, ATCC CRL-1651) and HEK293 are routinely used for transient expression of recombinant proteins. Preferred mammalian host cells for expressing the recombinant antibodies of the disclosure include myeloma cells such as Sp2/0, YB2/0 (ATC CRL-1662), NSO, and P3×63.Ag8.653 (e.g. SP2/0-Ag14) because of their high rate of expression. In particular, for use with NSO myeloma cells, another preferred expression system is the GS gene expression system. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Illustrative of cell cultures useful for the production of the antibodies, specified portions or variants thereof, are mammalian cells. Mammalian cell systems often will be in the form of monolayers of cells although mammalian cell suspensions or bioreactors can also be used.

In an alternative method of producing the antibodies of the disclosure, a non-human animal in which is one or more, and preferably essentially all, of the cells of the animal contain a heterologous nucleic acid introduced by way of human intervention, a transgene, coding for the antibody. The transgene can be introduced into the cell, directly or indirectly, by introduction into a precursor of the cell, by way of deliberate genetic manipulation, such as by microinjection or by infection with a recombinant virus. Methods for generating non-human transgenic mammals are known in the art. See, e.g., but not limited to, U.S. Pat. Nos. 5,827,690; 5,849,992; 4,873,316; 5,849,992; 5,994,616; 5,565,362; and 5,304,489. Such methods can involve introducing DNA constructs into the germ line of a mammal to make a transgenic mammal. For example, one or several copies of the construct may be incorporated into the genome of a mammalian embryo by standard transgenic techniques. In addition, non-human transgenic mammals can be produced using a somatic cell as a donor cell. The genome of the somatic cell can then be inserted into an oocyte and the oocyte can be fused and activated to form a reconstructed embryo. For example, methods of producing transgenic animals using a somatic cell are described in U.S. Pat. No. 6,147,276; Baguisi et al. *Nature Biotech.,* 17, 456-461, 1999; Campbell et al., *Nature,* 380, 64-66, 1996; Cibelli et al., *Science,* 280, 1256-8, 1998; Kato et al., *Science,* 282, 2095-2098, 1998; Schnieke et al., *Science,* 278, 2130-2133, 1997; Wakayama et al., *Nature,* 394, 369-374, 1998.

The antibodies may be produced in mammary glands of animals using promoters that are preferentially activated in mammary epithelial cells, including promoters that control the genes encoding milk proteins such as caseins, beta lactoglobulin. See, Clark et al., *Bio Technology,* 7: 487-492, 1989; Gordon et al. *Bio* Technology, 5: 1183-1187, 1987), and Soulier et al., *FEBS Letts.,* 297: 13, 1992). Antibodies of the present disclosure can additionally be produced using at least one anti-DbpA antibody encoding nucleic acid to provide transgenic plants and cultured plant cells (e.g., tobacco, maize, and duckweed). See, Cramer et al., *Curr. Top. Microbol. Immun.,* 240:95-118, 1999; Hood et al., *Adv. Exp. Med. Biol.,* 464:127-147, 1999; and Conrad et al., *Plant Mol. Biol.,* 38:101-109, 1998. Transgenic plants may also be used. See, Fischer et al., *Biotechnol. Appl. Biochem.,* 30:99-108, 1999; Ma et al., *Trends Biotechnol.,* 13:522-7, 1995; Ma et al., *Plant Physiol.,* 109:341-6, 1995; Whitelam et al., *Biochem. Soc. Trans.,* 22:940-944, 1994.

The nucleic acids of the present disclosure can also be prepared by direct chemical synthesis by known methods, e.g., U.S. Pat. Nos. 5,942,609; 6,521,427; 6,586,211; & 6,670,127.

Once prepared, the anti-DbpA antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography such as with a Protein A column, hydroxylapatite chromatography, lectin chromatography, HPLC, and the like.

Antibodies of the present disclosure include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present disclosure can be glycosylated or can be non-glycosylated, with glycosylated preferred.

The present disclosure also provides at least one anti-DbpA antibody composition comprising at least 1, 2, 3, 4, or more, e.g., 7, 10 or even 20 anti-DbpA antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the antiDbpA antibody amino acid sequences. In one specific embodiment, the composition comprises a plurality of the same anti-DbpA antibody or antigen-binding fragments thereof (e.g., MAb 6G8 or MAb 8C10). Alternately, the composition may comprise at least one unit each of MAb 6G8 and MAb 8C10 or antigen-binding fragments thereof.

The disclosure further relates to modified antibodies, e.g., fusion proteins, comprising, e.g., secretion signals and optionally heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present disclosure to facilitate purification. Such regions can be removed prior to final preparation of an antibody or at least one fragment thereof. To assist in affinity purification, various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., *Mol. Cell. Biol.*, 8:2159-2165, 1988); c-myc tags 8F9, 3C7, 6E10, G4, B7 and 9E10 antibodies thereto (Evan et al., *MCB*, 5:3610-3616, 1985); HSV glycoprotein D (gD) tag and its antibody (Paborsky et al., *Protein Enoineering*, 3(6):547-553, 1990); Flag-peptide (Hopp et al., *Bio Technology*, 6:1204-1210, 1988); KT3 peptide (Martin et al., *Science*, 255:192-194, 1992); an α-tubulin epitope (Skinner et al., *J. Biol. Chem.*, 266:15163-15166, 1991); and the T7 gene 10 protein peptide tag (Lutz-Freyermuth et al., *PNAS USA*, 87:6393-6397, 1990). A preferred tag is the FLAG tag.

The disclosure further relates to antibodies and antigen-binding fragments that are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., PEG, PPG), carbohydrate polymer, amino acid polymer or polyvinyl pyrolidone, and the fatty acid or fatty acid ester group having about 8-40 carbon units.

The modified antibodies and antigen-binding fragments can be prepared using suitable methods, such as by reaction with one or more modifying agents, e.g., amine-reactive activating groups including electrophilic groups such as tosylate, mesylate, halo (chloro, bromo, fluoro, iodo), N-hydroxysuccinimidyl esters (NHS); activating groups that can react with thiols including, e.g., maleimide, iodoacetyl, acrylolyl, pyridyl disulfides, 5-thiol-2-nitrobenzoic acid thiol (TNB-thiol); amine- or hydrazide-containing molecules; or an azide group. The modifications can be made using routine coupling techniques, e.g., Fisch et al., *Bioconjugate Chem.*, 3:147-153 (1992); Werlen et al., *Bioconjugate Chem.*, 5:411-417 (1994); Kumaran et al., *Protein Sci.*, 6(10):2233-2241 (1997); and Itoh et al., *Bioorg. Chem.*, 24(1): 59-68 (1996).

The present disclosure also relates to an anti-idiotypic (anti-Id) antibody that is specific for the antibodies of the disclosure, e.g., MAb 6G8 or MAb 8C10 or antigen-binding fragments thereof. An anti-Id antibody is an antibody that recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

The disclosure further relates to compositions comprising at least one anti-DbpA antibody and a carrier. Preferably the composition is a pharmaceutical composition comprising at least one anti-DbpA antibody and a pharmaceutically acceptable carrier. The compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Remington's Pharmaceutical Sciences, Gennaro et al., Ed., 18th Edition, Mack Publishing Co., Easton, Pa., USA (1990). Pharmaceutically acceptable carriers can be routinely selected that are suitable for the mode of administration, solubility and/or stability of the anti-DbpA antibody, fragment or variant composition as well known in the art or as described herein.

The disclosure further relates to stable formulations containing the anti-DbpA antibodies and buffering components and, optionally, stabilizers or preservatives, as well as multi-use formulations suitable for research, diagnostic and/or medical use. Anti-DbpA antibody compositions may include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; TRIS, tromethamine hydrochloride, or phosphate buffers. Preferred buffers for use in the present compositions are amino acids or organic acid salts such as citrate. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine. The formulations can cover a wide range of pHs, such as from about pH 4 to about pH 10, and preferred ranges from about pH 5 to about pH 9, and a most preferred range of about 6.0 to about 8.0. Preferably the formulations of the present disclosure have pH between about 6.8 and about 7.8.

Other additives, such as a pharmaceutically acceptable solubilizers such as surfactants: Tween 20 (polyoxyethylene (20) sorbitan monolaurate), Tween 40 (polyoxyethylene (20) sorbitan monopalmitate), Tween 80 (polyoxyethylene (20) sorbitan monooleate); Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. Amounts will generally range between 0.001 and 14% by weight of the formulation. Especially preferred surfactants for purposes of this disclosure are polyoxyethylene sorbitan monooleate, polysorbate 80, polysorbate 20, or the like. Additional agents known in the art for formulation of a protein such as DbpA antibodies, or specified portions or variants, can also be included in the formulation. Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, protamine and the like. Carbohydrate excipients suitable for use in the disclosure include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol, aldonic acids, such as gluconate, esterified sugars, and the like. Preferred carbohydrate excipients for use in the present disclosure are mannitol, trehalose, and raffinose. Additionally, anti-DbpA antibody compositions of the disclosure can include polymeric excipients/additives such as polyvinylpyrrolidones, ficolls (a polymeric sugar), dextrates (e.g., cyclodextrins, such as 2-hydroxypropyl-alpha-cyclodextrin), polyethylene glycols, flavoring agents, antimicrobial agents, sweeteners, antioxidants, antistatic agents, lipids (e.g., phospholipids, fatty acids), steroids (e.g., cholesterol), and chelating agents (e.g., EDTA).

The formulations can be prepared by a process which comprises mixing at least one anti-DbpA antibody and an aqueous diluent. The diluent will preferable contain buffering components and, optionally, stabilizers or preservatives. Mixing the at least one anti-DbpA antibody in an aqueous diluent is carried out using conventional dissolution procedures.

The pharmaceutical compositions or formulations of the disclosure can be administered to a patient in accordance with the present disclosure via a variety of delivery methods including SC or IM injection; transdermal, pulmonary, transmucosal, implant, osmotic pump, cartridge, micro pump, or other means appreciated by the skilled artisan, as well-known in the art. The formulation is sterilized by known or suitable techniques.

The disclosure further relates to an article of manufacture comprising packaging material and at least one vial comprising a solution of at least one anti-DbpA antibody with the prescribed buffers and/or preservatives, optionally in an aqueous diluent, wherein said packaging material comprises a label that indicates that such solution can be held over a period of time, e.g., 96 hours or more. The disclosure further relates to kits comprising a first vial comprising lyophilized anti-DbpA antibody, and a second vial comprising an aqueous diluent of prescribed buffer or preservative, optionally together with instructions for using the antibody as a research reagent, a diagnostic product or a therapeutic product. The aqueous diluent typically comprises a pharmaceutically acceptable buffer such as sodium citrate, L-histidine and L-histidine hydrochloride monohydrate, sodium phosphate in sterile water for injection and adjusted to a suitable pH. Preferably, the aqueous diluent optionally further comprises a pharmaceutically acceptable polypeptide stabilizer. Polypeptide stabilizers include sucrose, sodium chloride, L-arginine, and polysorbate 20, polysorbate 80, and (alpha)-trehalose dehydrate. The aqueous diluent optionally further comprises a pharmaceutically acceptable preservative. Preferred preservatives include those selected from the group consisting of benzyl alcohol, benzalkonium chloride, benzethonium chloride, sodium dehydroacetate, or mixtures thereof. The concentrations are dependent on the diluent buffer, if any, the stabilizer and the preservative selected and are readily determined by the skilled artisan.

The range of at least one anti-DbpA antibody in the product of the present disclosure includes amounts yielding upon reconstitution, if in a wet/dry system, concentrations from about 10 ng/ml to about 1000 mg/ml (preferably about 1 mg/ml to about 100 mg/ml), although lower and higher concentrations are operable and are dependent on the intended delivery vehicle, e.g., solutions will differ from transdermal patch, pulmonary, transmucosal, or osmotic pumps.

The present claimed articles of manufacture are useful for administration over a period of immediately to twenty-four hours or greater. Accordingly, the presently claimed articles of manufacture offer significant advantages to the patient. Formulations of the disclosure can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

Systems for administering the compositions or formulations, e.g., syringes, depots, pens, droppers, etc., are also contemplated by the disclosure.

Embodiments of the disclosure further provide for surfaces comprising the aforementioned antibody or antigen compositions, wherein the antibody or antigen is oriented to permit binding to a partner. Preferably, the surface is a surface of a solid support. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Nitrocellulose, nylon and other microporous structures are useful, as are materials with gel structure in the hydrated state. Further examples of useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a preexisting natural polymer.

Preferably, the support is a well of an array plate, e.g., a microarray such as a protein array or an antibody array. Methods for constructing such arrays are known in the art.

There are many solid supports which can be used for the method and the kit of the present disclosure. Well known materials which may be employed include glass, polystyrene, polypropylenes dextran, nylon, agarose, dextran, acrylamide, nitrocellulose, PVDF and other materials, in the form of tubes, beads, membranes and microtiter plates formed from or coated with such materials, and the like. The isolated and purified recombinant polypeptides and/or the antibodies of the present disclosure can be either covalently or physically bound to the solid support, by techniques such as covalent bonding via an amide, ester or disulfide linkage, or by adsorption. This binding or immobilization can be accomplished by using e.g., covalent bonding via an amide, ester or disulfide linkage between the solid support and the antibodies (e.g., via the Fc domain) or the epitopes of the antigen. In case the antigen/antibody is fused to GST, the fusion polypeptide is preferably immobilized in such a way that it is aligned on the solid support via a disulfide linkage between the solid support presenting glutathione on its surface and the GST portion of the polypeptide. Presently preferred for use as a solid support are micro titer plates made of polystyrole which can be obtained from various commercial suppliers such as NUNC, Costar, Greiner, Falcon or Coring Inc.

In case the method of detecting and/or quantifying antigens, e.g., DbpA antigens, is performed on a solid support, usually, the solid support is coated with the isolated and purified recombinant antibodies or antigen-binding fragments thereof. Coating may be performed by using a coating buffer known to the person skilled in the art such as PBS buffer or carbonate buffer. Such coating buffers as well as solid supports already coated might be included as reagents to the kit of the present disclosure. In a preferred mode for performing the above described method of the disclosure it is important to use certain "blockers" which might be included as a reagent in the kit of the disclosure as well. The "blockers" are added to assure that non-specific proteins, protease, or antibodies other than those that bind specifically to the antigenic peptides do not cross-link or destroy the antigens or antibodies on the solid support, or the radiolabeled indicator antigen or antibody, to yield false positive or false negative results. A usual blocker which can be used is bovine serum albumin (BSA), which is preferred. The blocker can be added in buffer solution like PBS buffer. In case a solid support is used the blocker is usually added after coating the solid support.

In certain aspects, the present disclosure excludes naturally occurring DbpA proteins that contain SEQ ID NO: 78, including naturally-occurring antibodies that bind thereto. Preferably, non-natural antigens of the disclosure comprise at least one modification in a natural DbpA protein, wherein the modification may alter a primary structure (e.g., amino acid sequence), secondary structure (e.g., sheet, loop, and/or helical configuration), or tertiary structure (e.g., 3D structure and/or epitope configuration), or quarternary structure (e.g., multi-subunit structure of DbpA interacting with decorin) of the protein. Representative examples of modifications include, e.g., mutations, deletions or truncations, additions or fusions, alterations in post-translational processing, e.g., altered ubiquitination, prenylation, phosphorylation, glycosylation, methylation, AMPylation, and de-AMPylation, phosphocholination, and de-phosphocholination, which may or may not change the biological activity of the protein (e.g., antigencity). In the context of antibodies, modifications include, dimerization, multimerization, bispecificity, multi-specifity, chimeras, humanization, fusions, truncations (e.g., of CH1 domain), deletions (e.g., of Fc portion), domain swapping (e.g., replace IgG constant domains with IgM constant domains), tagging (e.g., attaching a label such as a dye), Likewise, in the context of nucleic acids encoding antigens or antibodies of the disclosure, modifications may include polymorphisms, mutations, indels, codon optimization, truncations, fusions (chimeras), alteration of non-coding regions (e.g., change in promoter, regulator, repressor, or other elements; deletion of intronic sequences), and synthetic cDNA sequences that differ from naturally-occurring DNA counterparts.

Antigenic Peptides (PEP)

In some embodiments, the disclosure relates to antigenic peptides that comprise, consist essentially of, or consist of fragments of decorin-binding Protein A from *Borrelia Burgdorferi*. As provided above, the antigen (PEP) preferably comprises aa24-191 of B. *Burgdorferi* DbpA (full length sequence shown in SEQ ID NO: 78; fragment sequence provided in SEQ ID NO: 77).

The antigenic peptides (PEP) may comprise acid mutations. Such mutations are typically selected to so as to substantially preserve the antibody binding activity of the peptide. Guidance for substitutions, insertion, or deletion may be based on alignments of amino acid sequences of different variant proteins or proteins from different species. For example, at certain residue positions that are fully conserved, substitution, deletion or insertion is generally disfavored, while at other positions where one or more residues are not conserved, an amino acid change can be tolerated. Residues that are semi-conserved may tolerate changes that preserve charge, polarity, and/or size. For example, a compound or peptide comprising amino acids 24-191 of B. *Burgdorferi* DbpA (SEQ ID NO: 77) may have 1, 2, 3 or 4 amino acid mutations comprising substitutions, deletions, or insertions. Likewise, PEP can include additional amino acids at the amino and/or carboxyl terminal. In these aspects, it is generally preferred that the N-terminus or the C-terminus or both the N- and the C-termini of the peptide does not contain a corresponding amino acid from a naturally occurring protein, such as B. *Burgdorferi* DbpA (UNIPROT #O50917). However, this exclusion does not encompass chimeras, e.g., wherein the core DbpA fragment sequence is from species A (e.g., B. *Burgdorferi*) and the additional amino acids at the N- or C terminus are made up of corresponding sequences from species B (e.g., *B. afzelii, B. finlandensis, B. mayonii, B. garinii, E. coli*).

In some embodiments, the PEP component of the compounds of Formula I comprises, consists essentially of, or consists of amino acids (aa) 1-168 of SEQ ID NO: 77 or a fragment thereof comprising, consisting essentially of, or consisting of aa 2-168, aa 3-168, aa 4-168, aa 5-168, aa 6-168, aa 7-168, aa 8-168, aa 9-168, aa 10-198, aa 11-198, aa 12-198, aa 13-168, aa 14-168, aa 15-168, aa 16-168, aa 17-168, aa 18-168, aa 19-168, aa 20-168, aa 21-168, aa 22-168, aa 23-168, aa 24-168, aa 25-168, aa 26-168, aa 27-168, aa 28-168, aa 29-168 of SEQ ID NO: 77.

In certain aspects, this disclosure excludes naturally occurring proteins comprising SEQ ID NO: 77, e.g., the full-length *B. Burgdorferi* DbpA (UNIPROT #O50917).

The disclosure further relates to derivatives such as salts (e.g., hydrochloride salt, hydrobromide salt, sulfate salt, citrate salt, tosylate salt), amides, esters, enol ethers, enol esters, acetals, ketals, acids, bases, solvates, hydrates, polymorphs or prodrugs of the individual amino acids or the aforementioned peptide compounds (PEP).

In some embodiments, the peptide (PEP) may include one to about four, preferably one or two, non-proteinogenic amino acids, such as a D-amino acid (e.g., D-alanine), Norleucine (Nle); 4-hydroxyproline (HYP); 3,4-dehydro-L-proline (DHP); aminoheptanoic acid (AHP); (2R,5S)-5-phenyl-pyrrolidine-2-carboxylic acid (2PP); L-a-methylserine (MS); N-methylvaline (MV); 6-aminohexanoic acid (6-AHP); 7-aminoheptanoic acid (7-AHP), and the like.

The disclosure further relates to modified peptides (PEP). For example, the peptide (PEP) can be cyclized. As another example, the peptide (PEP) can have one or more amino acid modifications. Modifications of interest that do not alter primary sequence include chemical derivatization of the peptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, such as mammalian glycosylating or deglycosylating enzymes. Also embraced are peptides that have phosphorylated amino acid residues, e.g., phosphotyrosine, phosphoserine, or phosphothreonine.

Also provided in the disclosure are peptides that have been modified using ordinary molecular biological techniques and synthetic chemistry so as to improve their resistance to proteolytic degradation or to optimize solubility properties or to render them more suitable as an immunogen. The disclosure further relates to peptides containing other types of modifications including, e.g., (1) end-capping of the terminal of the peptides, such as amidation of the C-terminus and/or acetylation or deamination of the N-terminus; (2) introducing peptidomimetic elements in the structure; and (3) cyclization, in which the cyclization of the peptide can occur through natural amino acids or non-naturally-occurring building blocks.

The disclosure also relates to antigenic peptides that have been modified with polymers. For example, inclusion of a non-naturally occurring amino acid can provide for linkage to a polymer, a second polypeptide, a scaffold, etc. For example, a subject antigenic peptide linked to a water-soluble polymer can be made by reacting a water-soluble polymer (e.g., poly(ethylene glycol) (PEG)) that comprises a carbonyl group to an the subject antigenic peptide that comprises a non-naturally encoded amino acid that comprises an aminooxy, hydrazine, hydrazide or semicarbazide group. Suitable polymers can have an average molecular weight in a range of from 500 Da to 50 kDa, e.g., from 5 kDa to 40 kDa, from 25 kDa to 40 kDa, or from 40 kDa to 60 kDa.

The disclosure relates to peptidomimetics that have the same sidechains as one or more peptides described herein. The disclosure further relates to peptoids derived from one or more above-described peptides. The term "peptoid" refers to a polypeptide containing one or more N-substituted glycine residues. Representative examples of peptoids are provided in, e.g., U.S. Pat. Nos. 6,075,121 and 6,887,845.

The disclosure further relates to variant peptides having at least 1 amino acid variation (e.g., substitution, deletion, addition) compared to the parent polypeptide, e.g., from about 1 to 10 ten amino acid variations, 1 to about 5 amino acid variations compared to the parent, or 1, 2, 3, 4 or 5 amino acid variations, e.g., differing in amino acid sequence by one, two, three, four, or five amino acids, compared to the amino acid sequence set forth in one of SEQ ID NO: 77 or a functional fragment thereof. Preferably, variants of longer polypeptide sequence of SEQ ID NO: 77 or a functional fragment thereof may be able to tolerate a greater number of variations (e.g., 1, 2, 3, 4, 5, 6, 7, 8, 9, 10, or more, e.g., 20) in the polypeptide sequence. Variant polypeptides of the disclosure comprising substitutions generally comprise conservative substitutions.

Under an alternate embodiment, the variant peptide may comprise a sequence which is at least about 70%, 75%, 80%, 85%, 90%, 95%, 96%, 97%, 98% or 99%, identical to, for example, a polypeptide having an amino acid sequence set forth in one of SEQ ID NO: 77 or a functional fragment thereof. Methods/programs for determining % identity between two sequences have been described previously.

The disclosure further relates to recombinant antigenic peptides (rPEP). Depending on the type of host cell used in recombinantly producing the antigenic peptides, the rPEP may be glycosylated or unglycosylated. Glycosylated rPEP produced by, e.g., mammalian or insect cells, are preferred.

The disclosure further relates to fusion molecules comprising a peptide (PEP) of the instant disclosure (a peptide of SEQ ID NO: 77 or a functional fragment thereof) and a fusion partner. Preferably, the fusion molecule is a fusion protein. A "fusion protein" of this disclosure comprises a peptide of SEQ ID NO: 77, or a functional fragment thereof, that is bonded through a peptide bond to an amino acid sequence that is not bonded to SEQ ID NO: 77 in a naturally occurring protein. Illustrative fusion polypeptides include fusions of a peptide of the disclosure (or a fragment thereof) to a heterologous protein or polypeptide, e.g., a tag.

In some embodiments, the antigenicity of the peptide (PEP) of the disclosure may be improved using a carrier. For instance, it has been found that proteins from the group of bovine serum globulin (BSG), keyhole limpet hemocyanin (KLH), ovalbumin (OVA), and bovine serum albumin (BSA), are effective carriers of antigens and their inclusion greatly boosts the immune response in a host. Accordingly, the disclosure relates to antigenic peptides which are fused to a carrier protein on the N-terminus or the C-terminus, preferably the C-terminus. The antigen carrier is selected from bovine serum globulin (BSG), keyhole limpet hemocyanin (KLH), ovalbumin (OVA), and bovine serum albumin (BSA). In one particular example, the C-terminal end of the antigenic peptide is fused to the N-terminal end of KLH (PEP-KLH) via an m-maleimidobenzoyl-N-hydroxysuccinimide ester linker.

The heterologous protein in fusion peptides of the disclosure can include a linker which joins or links a carrier moiety or peptide to an antigenic peptide. The linker may be a peptide having any of a variety of amino acid sequences. A linker which is a spacer peptide can be of a flexible nature, although other chemical linkages are not excluded. A linker peptide can have a length of about 1, 2, 3, 4, 5 amino acids or from about 1 to 2, 1 to 3, 2 to 4, 2 to 5, 1 to 5, 5 to 10, 10 to 20, 20 to 30, or 30 to 40 amino acids in length. Peptide linkers with a degree of flexibility can be used. The linking peptides may have virtually any amino acid sequence, where in some embodiments the linker peptide will have a sequence that results in a generally flexible peptide. The use of small amino acids, such as glycine and alanine, are of use in creating a flexible peptide. The creation of such sequences is routine to those of skill in the art. Various linkers are commercially available and are considered suitable for use.

Exemplary flexible linkers which can be used to join or link a carrier moiety to a antigenic peptide, for example, via peptide bonds, include glycine polymers (e.g., (G)n, where n is an integer from 1 to about 20; preferably 1, 2 or 3); glycine-serine polymers (including, for example, (GS)n, GSGGSn (SEQ ID NO: 84) ("GSGGS" disclosed as SEQ ID NO: 72) and GGGSn (SEQ ID NO: 85) ("GGGS" disclosed as (SEQ ID NO: 73), where n is an integer of between 1 and 10, e.g., 1, 2, 3, 4, 5, 6, 7, or more; preferably 1, 2 or 3), glycine-alanine polymers, alanine-serine polymers, lysine polymers (e.g., (K)n, where n is an integer from 1 to about 20; preferably 1, 2 or 3) and other flexible linkers known in the art. Glycine and glycine-serine polymers are of interest since both of these amino acids are relatively unstructured, and therefore may serve as a neutral tether between components. Glycine polymers are used in some embodiments. See Scheraga et al., in *Reviews in Computational Chemistry*, K. B. Lipkowitz and D. B. Boyd, *Eds.*, VCH Publishers, New York (1992). Lysine polymers are of interest because they have amine ($NH_2$) side chain (R) groups that can be coupled to moieties of interest. For instance, lysines easily react with N-hydroxysuccinimide (NHS) esters incorporated into compounds such as dyes to form stable amides that can be decoupled using a protic buffer. Exemplary flexible linkers include, e.g., GG, GGG, GGS, GGSG (SEQ ID NO: 68), GGSGG (SEQ ID NO: 69), GSGSG (SEQ ID NO: 70), GSGGG (SEQ ID NO: 71), GSGGS (SEQ ID NO: 72), GGGS (SEQ ID NO: 73), GSSSG (SEQ ID NO: 74), KK, KKK, KKKK (SEQ ID NO: 75).

In another embodiment, the linker is non-peptide linker. Non-peptide linker moieties can also be used to join or link a carrier moiety to an antigenic peptide. The linker molecules are generally about 6-50 atoms long. The linker molecules include, e.g., aryl acetylene, ethylene glycol oligomers containing 2-10 monomer units, diamines, diacids, or combinations thereof.

In an alternative embodiment, the peptide may be linked to the carrier peptide by a disulfide bond. In some embodiments, the disulfide bond is formed between two cysteines, two cysteine analogs or a cysteine and a cysteine analog. In yet another embodiment, the peptide may contain an additional amino acid comprising a reactive side chain, e.g., SH group of cysteine that is coupled to other moieties such as linkers via click chemistry. See Liang et al., *J. Angew. Chem.*, Int. Ed., 48, 965 (2009).

In certain embodiments, the antigenic peptides (PEP) are labeled, e.g., with a detectable label. The detectable label may be located on or within any part of the peptide molecule, e.g., N-terminus, C-terminus, R-group, or even the a-carbon (e.g., via use of radiolabeled carbon). In the context of fusion proteins having at least two components, e.g., peptide and carrier, the detectable label may be located on or within any component. Preferably, the detectable label is located in the antigenic peptide component of the compound.

The term "label," as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, streptavidin, protein A, protein G, antibodies or fragments thereof, polyhistidine, $Ni^{2+}$, Flag tags, myc tags, heavy metals, and enzymes (including alkaline phosphatase, peroxidase, and luciferase). Such methods are well-known in the art. In certain embodiments, the peptides are labeled with label which is detectable.

In some embodiments, the peptides are conjugated with donor and acceptor fluorophores, respectively, which form a FRET pair. FRET can be used, for example, in an array format in order to determine if a particular secondary antibody is bound regardless of the identity of the analyte to which it binds. In some embodiments, the label is a lipid. In some embodiments, the lipid is a synthetic phospholipid derivative. In some embodiments, the synthetic phospholipid derivative is DDPC, DLPC, DMPC, DPPC, DSPC, DOPC, POPC, DEPC or a derivative thereof selected from DLPC, DMPC, or DPPC; preferably DLPC, DMPC or DPPC.

The peptides of the disclosure may be labeled using any routine method. In some embodiments, the peptides (PEP) are labeled by the introduction of active amino or thiol groups in the core peptide structure. Reaction conditions such as pH, amine fluorophore concentration, and incubation time and temperature affect the yield of products formed. At high concentrations of the amine fluorophore (3M), transamination can approach 100%.

Probes (e.g., antibodies which bind to the antigenic peptides of the disclosure) or probe-specific binding partner (e.g., secondary antibodies that bind to the antibody probes) may also be labeled, for example, using one or more of the aforementioned detectable labels. It is to be understood that probes may comprise antigenic peptides of the disclosure that are labeled which may bind to antibodies that are specific thereto and thereby be employed in a manner analogous to how labeled antibodies are employed. For instance, in the case of competitive ELISA assays, labeled antigens may be used as probes to identify amount and/or specificity of binding between DbpA antigens in a sample (e.g., a patient's blood) and the antibodies of the disclosure.

The detectable label may be conjugated to the antigenic peptide (PEP) of the disclosure either directly or via a linker, e.g., glycine or glycine serine linker such as, for example, GGGS (SEQ ID NO: 73).

The antigenic peptides may be prepared using recombinant methods or chemical synthetic methods described previously.

The disclosure further relates to compositions or kits comprising the antigenic peptides of the disclosure (PEP). The composition can comprise, in addition to the antigenic peptide, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropane sulfonic acid (TAPS), etc.; a solubilizing agent; a detergent, e.g., a non-ionic detergent such as TWEEN-20, etc.; a protease inhibitor; glycerol; and the like.

Compositions comprising the antigenic peptide may include a buffer, which is selected according to the desired use of the peptide, and may also include other substances appropriate to the intended use. Those skilled in the art can readily select an appropriate buffer, a wide variety of which are known in the art, suitable for an intended use.

In some embodiments, a composition comprising the antigenic peptide is a diagnostic composition. Diagnostic compositions according to the disclosure can, for example, be employed in usual immunoassays in which the at least one peptide of the composition is reacted with antibodies of the disclosure (as controls). As stated above the disclosure does not only cover diagnostic compositions but also especially immunoassay methods in which the compositions are used as antigenic substance.

One further embodiment of the disclosure intended for heterogeneous assays provides a composition wherein at least one peptide or fusion peptide is linked to solid support.

Independent on the form of the assay a further embodiment provides that the composition includes a tracer complex composed of at least one peptide or fusion peptide linked to a marker, e.g., a fluorescent or a luminescent molecule, either directly or via a linker. Such reagents are especially useful in SPR assays.

The disclosure further relates to kits or other articles of manufacture which contains one or more of antigenic peptide or a composition comprising the same, together with instructions for formulating and/or using the composition, e.g., generating antibodies. Kits or other articles of manufacture may include a container, a syringe, vial, a surface, or any other article, device or equipment useful in conducting the diagnostic test (e.g., in vitro or ex vivo). Diagnostic tests may also be conducted in vivo. Suitable containers include, for example, bottles, vials, syringes (e.g., pre-filled syringes), ampules, cartridges, reservoirs, pumps, or lyojects. The container may be formed from a variety of materials such as glass or plastic.

Compositions and/or kits for manufacture of the polypeptide may include nucleic acids, e.g., cDNA, encoding the polypeptide having the sequence set forth in SEQ ID NO: 77 or a variant thereof or a functional fragment thereof and a carrier, e.g., buffer. Expression kits may include vectors, e.g., phages (e.g., T7), phagemids, cosmids, plasmid vectors (e.g., bacterial or yeast), viral vectors (e.g., retroviral, lentiviral, adenoviral, adeno-associated viral, hybrid, baculoviral), which when incorporated into a suitable host system (e.g., cell such as a mammalian cell), encode the polypeptide of SEQ ID NO: 77 or a variant thereof or an immunogenic fragment thereof.

The present disclosure provides nucleic acids, where a subject synthetic nucleic acid comprises a nucleotide sequence encoding one or more antigenic peptides of the present disclosure. Nucleic acids include oligonucleotides, nucleotides, polynucleotides, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 10 nucleotides in length, and most preferably are at least about 20 nucleotides, at least about 50 nucleotides, or more.

Included herein are nucleic acids encoding the antigenic peptides of the disclosure or an immunogenic fragment thereof, nucleic acids that are complementary to the encoding nucleic acids, or the RNA equivalent thereof, or a complementary RNA thereof.

In an especially preferred embodiment, the disclosure relates to polynucleotides which encode an antigenic peptide (PEP) comprising, consisting essentially of, or consisting of the sequence set forth in SEQ ID NO: 77. In particular, the polynucleotide is a DNA, e.g., cDNA, or a complementary strand thereto, or the RNA equivalent thereof, or a complementary RNA thereof. Depending on the type of the nucleic acid and/or the host cell to be used for the expression of the polypeptide product, the proximal (5') end of the nucleic acid may comprise a plurality of elements, e.g., initiation site (AUG), 5' untranslated region (UTR), and optionally a cap (e.g., m$^7$CAAP). As is understood in molecular biology, wherein the nucleic acid is for use in a prokaryotic host cell, e.g., *E. coli*, the 5' UTR may contain a ribosome binding site (RBS), also known as the Shine Dalgarno sequence (AGGAGGU), which is usually 3-10 base pairs upstream from the initiation codon (AUG). Alternately, wherein the nucleic acid is for use in a eukaryotic host cell, e.g., human kidney cell line 293T, the 5' UTR may contain the Kozak consensus sequence (ACCAUGG), which contains the initiation codon (AUG), cis-acting regulatory elements called upstream open reading frames (uORFs) and upstream AUGs and termination codons (uAUGs), which have a great impact on the regulation of translation. Also, unlike prokaryotes, 5' UTRs in eukaryotes can harbor introns.

Further included herein are nucleic acids encoding tagged antigenic peptides of the disclosure, e.g., histidine-tagged, Flag-tagged, or Myc-tagged antigenic peptides, or the complementary strand(s) of the nucleic acids encoding the tagged antigenic peptides, or the RNA equivalent of the encoding strand or the complementary strand, or a complementary RNA equivalent thereof.

Embodiments disclosed herein further relate to variants of the aforementioned polynucleotides. In some embodiments, included herein are variants of aforementioned nucleic acids which comprise, or alternatively consist of, a nucleotide sequence which is at least 80%, 85%, 90%, 95%, 96%, 97%, 98% or 99%, or greater % identity, e.g., 99.5% to nucleic acids encoding the antigenic peptides, e.g., a nucleic acid encoding SEQ ID NO: 77.

In another embodiment, included herein are variant polynucleotides which hybridize to one or more nucleic acid molecules under stringent hybridization conditions or lower stringency conditions. Also included herein are oligonucleotides, e.g., PCR primers, which hybridize to one or more nucleic acids, which can be used in PCR amplification or in a hybridization assay or microarray.

Also included herein are modified nucleic acids such as peptide nucleic acid (PNA). PNAs are described in the art, e.g., Nielsen et al., *Anticancer Drug Des.,* 8:53-63, 1993.

In some embodiments, the disclosure relates to surfaces comprising nucleic acids which encode the antigenic peptides of the disclosure. Such surfaces can be used to detect DbpA mRNA via hybridization-based detection schemes. For instance, probes that are complementary to nucleic acids encoding SEQ ID NO: 77 may be used in the detection. In a preferred embodiment, the surface is an array plate and the DbpA antigens in a sample are detected using routine techniques of DNA microarray.

Also included herein are vectors which contain one or more of the aforementioned nucleic acids. In some embodiments, the vector comprises at least one protein encoding nucleic acid, e.g., nucleic acids encoding at least one of the foregoing peptides (e.g., SEQ ID NO: 77), in operable linkage with one or more additional sequences. The additional sequences may be synthetic in nature. A nucleotide sequence encoding an antigenic peptide can be operably linked to one or more regulatory elements, such as a promoter and enhancer, that allow expression of the nucleotide sequence in the intended target cells (e.g., a cell that is genetically modified to synthesize the encoded antigenic peptide). In some embodiments, a subject nucleic acid is a recombinant expression vector. A nucleotide sequence encoding an antigenic peptide (PEP) can be present in an expression vector and/or a cloning vector. In some embodiments, the vector is a mammalian vector which allows for transient, stable, or lentiviral expression of proteins. The following mammalian vectors are especially preferred: pD2610, including variants thereof (transient); pD2500, including variants thereof (stable); or pD2100, including variants thereof (lentiviral). These vectors can be purchased from ATUM, Inc. (Newark, Calif., USA).

The present disclosure provides isolated host cells that are genetically modified (e.g., transformed cells or cell-lines) with a nucleic acid comprising a nucleic acid sequence which encodes an antigenic peptide. Preferably, the isolated genetically modified host cell can produce an antigenic peptide. Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

The disclosure further relates to cell cultures comprising the aforementioned transformed host cells which inducibly, transiently, or stably express the recombinant antigenic polypeptides or antibodies of the disclosure. Such cultures may comprise, e.g., monolayer cultures, liquid (e.g., floating) cultures, 2D cultures, 3D cultures (both scaffold-free and scaffold or matrix-dependent). Preferably, the host cells may be cultured in scaffold systems such as hydrogel matrices and solid scaffolds, and scaffold-free systems such as low-adhesion plates, nanoparticle facilitated magnetic levitation, and hanging drop plates.

The disclosure further relates to organs, organ systems, and/or transgenic animals which comprise the aforementioned host cells which comprise the polynucleotides that encode the antigenic peptides of the disclosure.

Embodiments of the instant disclosure further provide for systems, e.g., diagnostic systems or immunoapheresis systems, comprising the aforementioned compositions and/or kits.

Methods

The disclosure is directed inter alia to the detection of antigens that are diagnostic of Lyme disease. The disclosure provides specific and sensitive assays for diagnosing such diseases, thereby providing clarity to clinical assessment of the patient.

One aspect of the disclosure is a method for detecting Lyme disease in a subject suspected of having antibody against a causative agent of Lyme disease. The diagnostic method is useful for diagnosing subjects exhibiting the clinical symptoms of, or suspected of having, Lyme disease. Another aspect of the disclosure, there is provided a method for detecting Lyme disease in the subject having or suspected of having *B. burgdorferi* infection, comprising detecting DbpA antigen using one or more antibodies of the disclosure. Preferably, the method comprises detecting the DbpA antigen using MAb 6G8 or MAb 8C10 or antigen-binding fragments thereof.

Preferably the subject is a human or a domestic animal (e.g., dogs, cats, sheep, cows) or a wild animal (e.g., deer, elk, moose).

One aspect of the disclosure is a method for diagnosing Lyme disease in a subject (e.g., for diagnosing exposure to and/or infection by a pathogenic *Borrelia*), comprising measuring a bodily fluid (which would be expected to contain antibodies) of the subject for the presence of an antibody against a causative agent of Lyme disease (e.g. an antibody capable of binding to such an agent), wherein an elevated level of antibody in the subject compared to a corresponding level of antibody in a control (such as a known unaffected subject) indicates an infection by the causative agent and/or that the subject has Lyme disease. A "causative agent for Lyme disease," as used herein, includes a pathogenic species of *B. burgdorferi, B. afzelli*, or *B. garinii*. Other species of *Borrelia* which have been implicated in Lyme disease, such as, e.g., *B. lusitaniae* and *B. valaisianae*, are also included, provided they induce antibodies which can react specifically with the antigenic peptide of the disclosure.

Preferably, the disclosure provides a method for diagnosing Lyme disease in a subject (e.g., for diagnosing exposure to and/or infection by a pathogenic *Borrelia*), comprising measuring a bodily fluid (which would be expected to contain antibodies) of the subject for the presence of a DbpA antigen from a causative agent of Lyme disease (e.g., an antigen which shares significant homology or identity with SEQ ID NO: 77 or an immunogenic fragment thereof), wherein an elevated level of the antigen in the subject compared to a corresponding level of antibody in a control (such as a known unaffected subject) indicates an infection by the causative agent and/or that the subject has Lyme disease.

One embodiment of this method comprises contacting (incubating, reacting) a sample of a biological fluid (e.g., serum or CSF) from a subject to be diagnosed (a subject suspected of having Lyme disease) with the diagnostic reagent comprising the antibody of the disclosure or the antigenic peptide of the disclosure. In the presence of an antibody response to infection with a pathogenic *Borrelia*, an antigen-antibody complex is formed. Subsequently the reaction mixture is analyzed to determine the presence or absence of this antigen-antibody complex. A variety of conventional assay formats can be employed for the detection, such, e.g., as ELISA, microarray analysis, Luminex bead based assays or lateral flow methods. The presence of an elevated amount of the antibody-peptide complex indicates that the subject was exposed to and infected with a pathogenic *Borrelia* capable of causing Lyme disease. In any detection assay of the disclosure, a positive response is defined as a value of 1.5, 2, 3, 4 or more, e.g., 5 standard deviations greater than the mean value of a group of healthy controls. For the purposes of the initial screening, a positive response is defined as a statistically significant difference in the mean binding of diagnostic reagent (e.g., anti-DbpA antibody or the DbpA antigen) and the analyte (e.g., DbpA antigen or the subject's antibody in biological sample) compared to controls (e.g., a healthy subject). Statistical significance may be determined using a Kruskal-Wallis test followed by a Dunn's comparison test. In some embodiments, a second tier assay is performed to provide an unequivocal sero-diagnosis of Lyme disease.

One embodiment of the disclosure is a diagnostic immunoassay method, which comprises (1) taking a sample of body fluid or tissue likely to contain antibodies; (2) contacting the sample with an antibody of the disclosure or a peptide of the disclosure, under conditions effective for the formation of a specific antibody-antigen complex, e.g., reacting or incubating the sample and the anti-DbpA antibody of the disclosure (or reacting or incubating the sample and the DbpA peptide of SEQ ID NO: 77); and (3) assaying the contacted (reacted) sample for the presence of an antibody-antigen complex (e.g., determining the amount of an antibody-peptide complex).

Conditions for reacting peptides and antibodies so that they react specifically are well-known to those of skill in the art. See, e.g., Current Protocols in Immunology, Coligan et al, *Eds.*, John Wiley & Sons, Inc., N.Y. (2003) or the Examples herein.

The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, etc. are known to contain antibodies and may be used as a source of the sample.

Once the analyte and the probe are permitted to react in a suitable medium, an assay is performed to determine the presence or absence of an antibody-peptide reaction. Among the many types of suitable assays, which will be evident to a skilled worker, are ELISA, immunoprecipitation and agglutination assays.

In embodiments of the disclosure, the assay may comprise (1) immobilizing the analyte in the sample, adding the binding partner (e.g., peptide of SEQ ID NO: 77 or MAb 6G8 or MAb 8C10 or antigen-binding fragments thereof), and then detecting the degree of complex between the analyte and the probe. Detection may be facilitated using a labeled probe (e.g., labeled SEQ ID NO: 77 or labeled MAb 6G8 or MAb 8C10 or antigen-binding fragments thereof) or by adding a labeled substance (conjugate, binding partner), such as a labeled antibody, which specifically recognizes the probe; (2) immobilizing the probe of the disclosure, adding the sample containing an analyte, and then detecting the amount of the complex between the analyte and the probe, e.g., by adding a labeled substance (conjugate, binding partner), such as a labeled antibody, which specifically recognizes the probe in complex with the analyte; or (3) reacting the probe and the analyte without any of the reactants being immobilized, and then detecting the amount of the probe-analyte complex.

Immobilization of a peptide of the disclosure can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence HHHHHH (SEQ ID NO: 76) and the carrier comprises a nitrilotriacetic acid derivative (NTA) charged with $Ni^{2+}$ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology, supra). In a preferred assay, an antibody of the disclosure is immobilized to the solid or semi-solid surface or carrier by means of covalent or non-covalent binding, either prior to or after the addition of the sample comprising or believed to contain an antigen (e.g., DbpA or a variant thereof).

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the disclosure, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In one embodiment of the disclosure, probes (e.g., immunogenic fragments of SEQ ID NO: 77 or fragments of MAb 6G8 or MAb 8C10) are immobilized onto tiny polystyrene beads (microspheres), wherein each peptide is immobilized onto a bead with a unique spectral signature, and are analyzed by the xMAP® technology developed by Luminex Technology, Austin, Tex. Alternately, the probe is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody which binds to the first antibody. This secondary antibody can be labeled, e.g., with a radioactive, enzymatic, fluorescent, luminescent, or other detectable label, such as an avidin/biotin system.

In embodiments of the disclosure, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the probe is electro- or dot-blotted onto nitrocellulose paper. Subsequently, the biological fluid (e.g., serum or plasma) is incubated with the blotted probe, and analyte in the biological fluid is allowed to bind to the probe(s). The bound complex can then be detected, e.g. by standard immunoenzymatic methods. In another embodiment of the method, latex or polystyrene beads are conjugated to the probes and the biological fluid is incubated with the bead/probe conjugate, thereby forming a reaction mixture. The reaction mixture is then analyzed to determine the presence of the analyte.

One assay for the screening of blood products or other physiological or biological fluids is ELISA. Typically in an ELISA, the probe of the disclosure is adsorbed to the surface of a microtiter well directly or through a capture matrix. Residual, non-specific protein-binding sites on the surface are then blocked with an appropriate agent, such as BSA, heat-inactivated normal goat serum (NGS), or BLOTTO (a buffered solution of nonfat dry milk). The well is then incubated with a biological sample suspected of containing pathogenic *Borrelia* (e.g. *B. burgdoferi*) analyte (e.g., DbpA antigen or antibody thereto). The sample can be applied neatly, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound analyte and then incubated with an optimal concentration of an appropriate anti-immunoglobulin antibody (e.g., for human subjects, an anti-human immunoglobulin (ctHulg) from another animal, such as dog, mouse, cow, etc.) that is conjugated to an enzyme or other label by standard procedures and is dissolved in blocking buffer. The label can be chosen from a variety of enzymes, including horseradish peroxidase (HRP), β-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length).

Another useful assay format is a lateral flow format. Antibody to human or animal antibody or staph A or G protein antibodies is labeled with a signal generator or reporter (i.e., colloidal gold) that is dried and placed on a glass fiber pad (sample application pad). The diagnostic probe is immobilized on membrane, such as a PVDF (polyvinylidene fluoride) membrane (e.g., an IMMOBILON membrane (Millipore)) or a nitrocellulose membrane. When a solution of sample (blood, serum, etc.) is applied to the sample application pad, it dissolves the colloidal gold labeled reporter and this binds to all analyte in the sample. This mixture is transported into the next membrane (PVDF or nitrocellulose containing the diagnostic probe) by capillary action. If the analyte is present in the sample, they bind to the probe striped on the membrane generating a signal. An additional antibody specific to the colloidal gold labeled antibody (such as goat anti-mouse IgG) may be used to produce a control signal.

It should be understood by one of skill in the art that any number of conventional protein assay formats, particularly immunoassay formats, may be designed to utilize the isolated peptides of this disclosure for the detection of pathogenic Borelia (e.g., *B. burgdorferi*) infection a subject. This disclosure is thus not limited by the selection of the particular assay format, and is believed to encompass assay formats that are known to those of skill in the art.

Other Applications

Therapeutic or Prophylactic Applications

The disclosure relates to methods of generating an immune response in a subject, including a human. The methods generally involve administering to an animal or human a pharmaceutical composition comprising an immunologically effective amount of a DbpA fragment (e.g., SEQ ID NO: 77), nucleic acid or antibody composition as disclosed herein. Animals to be immunized include mammals, particularly humans, but also murine, bovine, equine, porcine, canine, feline and non-human primate species. The term "immunologically effective amount" is meant an amount of a DbpA fragment, polypeptide, peptide, nucleic acid or antibody composition that is capable of generating an immune response in the recipient animal or human. This includes both the generation of an antibody response (B cell response), and/or the stimulation of a cytotoxic immune response (T cell response). In terms of preventative and treatment measures, these methods may be used for the prevention or treatment of infections caused by pathogens such as *B. burgdorferi, B. afzelii, B. garinii*, and related *Borrelial* species.

The disclosure relates to methods of producing bioreagents, e.g., cytotoxic T lymphocytes (CTLs) and, more particularly, reactive antibodies using the DbpA fragments of the disclosure. Bioreagents such as CTLs and antibodies have numerous practical uses outside prophylaxis and therapy, such as in vitro diagnostics.

In terms of the prevention of infections caused by pathogens such as *B. burgdorferi, B. afzelii, B. garinii*, and related *Borrelial* species a plurality of vaccinations may be used. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064.

The pharmaceutical, vaccine or other compositions for administration to generate an immune response will typically include combinations of partially or significantly purified *Borrelial* proteins, polypeptides and/or peptides, obtained from natural or recombinant sources, which proteins, polypeptides and/or peptides may be obtainable naturally or either chemically synthesized, or alternatively produced in vitro from recombinant host cells expressing DNA segments encoding such proteins, polypeptides and/or peptides. Smaller peptides that include reactive epitopes, such as those between about 10 amino acids and about 50 amino acids, between about 15 amino acids and about 25 amino acids in length, or even between about 50 amino acids and about 100 amino acids in length will often be preferred. The antigenic proteins, polypeptides and/or peptides may also be combined with other agents.

In other aspects of the present disclosure, administration of antibodies reactive with *Borrelial* proteins to at-risk subjects will be effective for prophylaxis of, and in the case of infected subjects for therapy of, Lyme disease. Antibodies may be of several types including those raised in heterologous donor animals or human volunteers immunized with *Borrelial* proteins, monoclonal antibodies (mAbs) resulting from hybridomas derived from fusions of B cells from immunized animals or humans with compatible myeloma cell lines, so-called "humanized" mAbs resulting therefrom, or antibody-containing fractions of plasma from human donors residing in Lyme disease-endemic areas. It is contemplated that any of the techniques described herein might be used for the passive immunization of subjects for protection against, or treatment of, *Borrelial* infections, such as Lyme disease.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions. Adjuvants that may be used include IL-1, IL-2, IL-4, IL-7, IL-12, g-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum adjuvants. In addition to adjuvants, it may be desirable to coadminister biologic response modifiers (BRM), which have been shown to upregulate T cell immunity or down-regulate suppressor cell activity. Such BRMs include, but are not limited to, Cimetidine (CIM; 1200 mg/d) (Smith/Kline, PA); or low-dose Cyclophosphamide (CYP; 300 mg/m2) (Johnson/Mead, NJ) and Cytokines such as y-interferon, IL-2, or IL-12 or genes encoding proteins involved in immune helper functions, such as B-7.

Virtually all vaccination regimens of the present disclosure will be appropriate for use with DNA vectors and constructs in the form of DNA vaccination, e.g., as described by Ulmer et al., *Science,* 259: 1745-1749, 1993; Tang et al., Nature, 356: 152-154, 1992; Cox et al., *Infect. Immun.,* 67: 30-35, 1999; Fynan et al., *PNAS USA,* 90: 11478-11482, 1993; Wang et al., *J. Exp. Med.,* 177: 699-705, 1993; Wang et al., *J Immunol.,* 150: 3022-3029, 1993; and Whitton et al., *J. Virol.,* 67: 348-352, 1993. In addition to parenteral routes of DNA inoculation, including intramuscular and intravenous injections, mucosal vaccination is also contemplated, as may be achieved by administering drops of DNA compositions to the nares or trachea. It is also contemplated that a gene-gun could be used to deliver an effectively immunizing amount of DNA to the epidermis (Fynan et al., *PNAS USA,* 90: 11478-11482, 1993).

It is also contemplated that live antigen delivery systems will be useful in the practice of certain embodiments of the present disclosure. Examples of these include, but are not limited to, vaccinia virus, poliovirus, *Salmonella* sp., *Vibrio* sp. and *Mycobacteria* sp.

In certain embodiments, the disclosure further relates to use of compositions comprising the antibodies of the disclosure to eliminate DbpA toxins (or even pathogens such as *B. burgdorferi, B. afzelii, B. garinii,* and related *Borrelial* species) from a subject (e.g. human patient suffering from Lyme disease) ex vivo, e.g., via immunoapheresis.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Example 1: Lyme DbpA Chimeric Monoclonal Antibody Development for Lyme Antigen Detection A study was conducted to generate purified recombinant chimeric human antibodies (e.g., IgM) which are specific to Lyme antigen DbpA. A mammalian system was used to develop the cloning and expression of the synthesized genes of antibody. The purified chimeric DbpA IgM protein is used for the development of Lyme standards and controls in the lateral flow-based assays.

Monoclonal antibodies against Lyme antigens provide consistency that is desirable of diagnostic reagents. Also, such antibodies can be generated, as desired, so that they can be readily deployed, as needed, over a longer duration, e.g., during outbreaks.

First, murine monoclonal antibody is obtained by immunizing mice with an antigenic peptide. Next, hybridoma cell lines are developed and antibody variable regions sequences are obtained using RT-PCR technology. Next, expression vectors containing nucleic acids encoding such variable regions of the antibody are generated using recombinant techniques, e.g., cloning and sub-cloning. This is followed by generation of chimeric antibody constructs, wherein mouse CDRs are grafted into human IgG/M framework Fc region. Such constructs are utilized for antibody production, e.g., either batch production or production in commercial scale.

Materials & Methods

Mouse Immunization and Screening process: 5 mg of recombinant DbpA full length protein (without signal sequence) was used for mouse immunization. If peptides were used, biotininylated peptide (~2 mg) bound to neutravidin or synthetic peptide conjugated to KLH were used for immunization. KLH-fused antigens were preferred because they generated higher antibody titers. Mice (n=3) were used for immunization. Serum ELISA was performed to check for antibody production and additional boosting (e.g., with full-length recombinant protein) was performed.

For fusion and cloning, about 500 hybridomas were generated for screening. Excess fused hybridomas were frozen and retained to generate additional candidates, as needed. Depending on the health of the animals, mice whose B-cells were not fused to generate hybridomas were retained until the end of the project.

For screening, solid phase robotic ELISA screening was performed. Initially, the affinity of the 500 clones to one antigen was analyzed. For confirmatory screening, all ELISA positive clones to one antigen were re-screened. For peptide antigens (usually biotinylated), a streptavidin-coated plate was used for screening. For recombinant proteins, the full-length antigen was coated on plate for screening. The full length DbpA protein was used.

Next, positive clones were cultured in media and about 3 ml to 5 ml supernatant was analyzed using octet quantitation, which measures the on/off rate and ranks each sample based on $K_D$ values for each hybridoma/antibody sample to the full length protein.

II. Identification and sequencing of the full-length immunoglobulin gene transcripts expressed by mouse hybridomas 6G8 and 8C10. Immunoglobulin gene transcripts expressed by the above hybridomas were amplified with sets of SYNBUILD primers from cDNA generated from the hybridoma cells using standard RT-PCR protocol. The transcripts were sequenced using a standard dye-terminator capillary sequencing method. Annotated sequences of the identified immunoglobulin gene transcripts, the corresponding sequencing trace files and a sequencing report was compiled. DNA fragments of the identified regions, which are embedded in agarose, may be used for further amplification and/or downstream manipulation.

Design of Chimera Sequence for Cloning and Expression

Based on sequencing results and choice of human IgM sequences, the following sequence (6G8 as an example) was designed and chosen for cloning and expression. The protein is to be expressed in mammalian HEK cells and for easy chromatography purification of the recombinant protein.

```
>6G8_gamma1
                                          (SEQ ID NO: 86)
/translation =

MGWSCIMLFLAATATGVHSQVQLQQPGAELVKPGASVKLSCKASGYTFT

RYWMYWVKQRPGRGLEWIGRLDPNSGVTKYNEKFKSKATLTVDKSSSTA

YMQLSSLTSEDSAVYYCVRDDSWYFDVWGTGTTVTVSSAKTTPPSVYPL

APGSAAQTNSMVTLGCLVKGYFPEPVTVTWNSGSLSSGVHTFPAVLQSD
```

-continued

LYTLSSSVTVPSSTWPSQTVTCNVAHPASSTKVDKKIVPRDCGCKPCIC

TVPEVSSVFIFPPKPKDVLTITLTPKVTCVVVDISKDDPEVQFSWFVDD

VEVHTAQTKPREEQINSTFRSVSELPIMHQDWLNGKEFKCRVNSAAFPA

PIEKTISKTKGRPKAPQVYTIPPPKEQMAKDKVSLTCMITNFFPEDITV

EWQWNGQPAENYKNTQPIMDTDGSYFVYSKLNVQKSNWEAGNTFTCSVL

HEGLHNHHTEKSLSLSPGK.

>6G8_kappa
(SEQ ID NO: 34)
/translation =

MDMRAPAQFLGILLLWFPGARCEIQMTQSPSSMSASLGDRITITCQATQ

DIVKNLNWYQQKPGKPPSFLIYYATELAEGVPSRFSGSGSGSDYSLTIN

NLESQDFADYFCLQFYAFPLTFGAGTKLELRRADAAPTVSIFPPSSEQL

TSGGASVVCFLNNFYPRDINVKWKIDGSERQNGVLNSWTDQDSKDSTYS

MSSTLTLTKDEYERHNSYTCEATHKTSTSPIVKSFNRGEC.

>hIgM_HC_pFUSE(S37768 Ig mu chain C region-human)
(SEQ ID NO: 37)
GSASAPTLFPLVSCENSPSDTSSVAVGCLAQDFLPDSITFSWKYKNNSD

ISSTRGFPSVLRGGKYAATSQVLLPSKDVMQGTDEHVVCKVQHPNGNKE

KNVPLPVIAELPPKVSVFVPPRDGFFGNPRKSKLICQATGFSPRQIQVS

WLREGKQVGSGVTTDQVQAEAKESGPTTYKVTSTLTIKESDWLSQSMFT

CRVDHRGLTFQQNASSMCVPDQDTAIRVFAIPPSFASIFLTKSTKLTCL

VTDLTTYDSVTISWTRQNGEAVKTHTNISESHPNATFSAVGEASICEDD

WNSGERFTCTVTHTDLPSPLKQTISRPKGVALHRPDVYLLPPAREQLNL

RESATITCLVTGFSPADVFVQWMQRGQPLSPEKYVTSAPMPEPQAPGRY

FAHSILTVSEEEWNTGETYTCVVAHEALPNRVTERTVDKSTGKPTLYNV

SLVMSDTAGTCY.

IV. Gene Expression/Purification and Antibody Characterization

Chimera antibodies were designed and produced in order to maintain the two critical features: antigen-specific binding (from Fv/Fab region), and human IgM Fc region for the binding to anti-hu IgM Fc5u antibody (i.e. goat anti-human IgM Fc5u fragment-specific, JIR #109-005-129, in this case). The antigen-specific binding domain comes from the mouse hybridoma cell line, which secretes the monoclonal antibody. The human IgM Fc region (for the binding to anti-hu IgM Fc5u antibody) comes from the plasmid expression vector.

The construct design is as follows: Heavy Chain: Mouse VH-CH1 and human IgM u chain (CH2-4); Light Chain: Mouse VL-CL Briefly, LC full length and HC variable VH with CH1 were sub-cloned into full human IgM expression vectors. Full-length chimeric IgM was expressed in 293 cells by transient transfection and purified by one-step affinity purification. Purified antibodies were characterized by SDS-PAGE and SEC-HPLC.

Procedure: Mammalian culture was carried out in HEK 293 cells. Protein expression vectors were transfected in HEK293 using standard transfection methods. Cells were grown for 7 days and harvested. The pH of the supernatant was adjusted with IM HEPES pH 7.4. CAPTURESELECT IgM resin was used to capture proteins. The resin was washed was PBS and proteins were eluted with citrate buffer (50 mM Citrate pH 3.5, 100 mM NaCl). Proteins were desalted by PD-10 columns into PBS and protein concentration and amount were quantified by OD280 using calculated extinction coefficient. Reduced/non-reduced SDS-PAGE gels (BIORAD criterion Tris/Glycine/SDS, 4-20%) were used to determine purity and approximate size. Pierce Endotoxin Quantitation Kit or Charles River Nextgen PTS was used to determine endotoxin levels. Aggregation status was determined by HPLC, with detection at 280 nm using a Sepax Zenix-C SEC-300, 3 µm, 300 Å, 4.6*150 mm size exclusion column and PBS running buffer. Proteins were shipped as aliquots after filter sterilization, snap frozen in liquid nitrogen.

For BIACORE testing, DbpA antigen was immobilized on BIACORE CM5 chip by amine chemistry. Diluted chimeric antibody proteins were injected into prepared flow cell as well as reference flow cell. Response signals were recorded. 10 mM Gly-HCl, pH1.5 was used for surface regeneration. Purified antibody samples diluted in BSA/PBS buffer to the indicated concentration and lateral flow immunoassay test devices with a binding antigen for the antibody were prepared (n=10). Binding of antibody to the immunoassay was analysed using a commercially available instrument (SOFIA®, Quidel Corporation). Average number of IgM Height/Cutoff (cutoff=3410) were used.

Results

I. Mouse Immunization and Screening Process:

Phase I: Immunization & Tail Bleed screen-Recombinant DbpA protein (5 mg, MW 23 kDa was used in the immunization. After immunizing mice (n=3) with the antigen, tail bleeds were performed to achieve high titer (1:100,000) of positive serum, which were screened based on affinity to 100 ng/well DbpA in PBS adhered to Ni-NTA ELISA plate.

Phase II: Fusion & Cloning-Tail bleed data were reviewed and based on titers, positive confirmation of fusion was made. Roughly 500 hybridomas were generated for screening.

Phase III: Hybridoma Screening—From the 500 clones, ninety one positives were identified using solid-phase robotic ELISA screening, which were then used for confirmatory testing and screening ($2^{nd}$ screening). Forty clones were selected based on ELISA results. Mouse IgG quantitation data were requested. Of these, 28 clones were selected for Octet affinity scouting. Results are shown in Table 3 and 4.

Phase IV: Culture supernatant preparation and Octet mIgG quantification (with anti-mIgG Fc)-Octet scouting analysis was used to determine on/off rate and $K_D$ ranking for up to 28 samples to the full length protein The following 28 clones were selected Octet Affinity Scouting with DbpA as the analyte. The mAbs were determined with affinity ranging KD of nM to pM.

TABLE 3

Confirmatory ELISA and IgG quant data (40 clones)

| Sample ID | OD 405 | Calc Conc. µg/ml |
|---|---|---|
| 1A3 | 3.520 | 58.7 |
| 1B10 | 3.380 | 26.3 |
| 1B5 | 3.605 | >120 |
| 1B9 | 3.481 | 72.9 |
| 1C4 | 3.438 | 37.9 |
| 1D11 | 3.432 | 59.8 |

TABLE 3-continued

Confirmatory ELISA and IgG quant data (40 clones)

| Sample ID | OD 405 | Calc Conc. µg/ml |
|---|---|---|
| 1D12 | 3.377 | 39.4 |
| 1D7 | 3.233 | 48.1 |
| 1E1 | 3.473 | 26.4 |
| 2B5 | 3.297 | 17.1 |
| 2C10 | 3.209 | >120 |
| 3C2 | 3.398 | 33.1 |
| 4B3 | 3.160 | >120 |
| 4B9 | 3.445 | 45.9 |
| 4C1 | 3.242 | 28.9 |
| 4G9 | 3.341 | 17.6 |
| 4H12 | 3.353 | 78.7 |
| 4H3 | 3.155 | 28.7 |
| 4H6 | 3.151 | 36.6 |
| 5E11 | 3.422 | 23.4 |
| 5E4 | 3.315 | 17.4 |
| 5E6 | 3.146 | 35.9 |
| 5E9 | 3.155 | 38.1 |
| 5G6 | 3.141 | 45.2 |
| 5H3 | 3.378 | 20.5 |
| 5H5 | 3.259 | 26.8 |
| 6F11 | 3.448 | >120 |
| 6G1 | 3.273 | 14.9 |
| 6G2 | 3.174 | 33.8 |
| 6G8 | 3.165 | 17.4 |
| 7A10 | 3.147 | 47 |
| 7A7 | 3.305 | 16 |
| 7A8 | 3.278 | 35.9 |
| 7B8 | 3.154 | 46 |
| 7G7 | 3.400 | 79.2 |
| 8B4 | 3.187 | 32.2 |
| 8B8 | 3.386 | 82.6 |
| 8C10 | 3.243 | 27.9 |
| 8C11 | 3.146 | 40.4 |
| 8G10 | 3.188 | 29.9 |
| Ms IgG 25 µg/ml Positive Control | 0.220 | 24.8 |

Phase IV: Culture supernatant preparation and Octet mIgG quantification (with anti-mIgG Fc)-Octet scouting analysis was used to determine on/off rate and $K_D$ ranking for up to 28 samples to the full length protein The following 28 clones were selected Octet Affinity Scouting with DbpA as the analyte. The mAbs were determined with affinity ranging KD of nM to pM.

TABLE 4

Octet Affinity Scouting with anti-mIgG Fc sensor and DbpA as analyte.

| Loading Sample ID | Cycle | Sample ID | Conc. (nM) | Response | kdis(1/s) | kon(1/Ms) | KD (M) | Full X^2 | Full R^2 |
|---|---|---|---|---|---|---|---|---|---|
| 8C10 | 1 | DpbA | 100 | 0.1523 | <1.0E−07 | 3.56E+05 | <1.0E−12 | 0.0182 | 0.9423 |
| 5H3 | 2 | DpbA | 100 | 0.1555 | 6.06E−04 | 1.04E+06 | 5.80E−10 | 0.0065 | 0.9557 |
| 5G6 | 3 | DpbA | 100 | 0.1239 | 1.85E−03 | 1.01E+06 | 1.84E−09 | 0.0236 | 0.8861 |
| 4G9 | 1 | DpbA | 100 | 0.1682 | 8.45E−04 | 1.29E+06 | 6.54E−10 | 0.0198 | 0.8927 |
| 1D11 | 2 | DpbA | 100 | 0.1567 | 1.40E−03 | 8.02E+05 | 1.75E−09 | 0.0094 | 0.9647 |
| 1B9 | 3 | DpbA | 100 | 0.1468 | 2.92E−03 | 7.86E+05 | 3.72E−09 | 0.0175 | 0.9644 |
| 1D7 | 1 | DpbA | 100 | 0.1508 | 1.82E−03 | 9.99E+05 | 1.82E−09 | 0.0187 | 0.9406 |
| 2B5 | 2 | DpbA | 100 | 0.1341 | <1.0E−07 | 1.12E+06 | <1.0E−12 | 0.0204 | 0.8376 |
| 4B9 | 3 | DpbA | 100 | 0.1291 | 3.12E−04 | 7.80E+05 | 4.00E−10 | 0.0051 | 0.9500 |
| 1B10 | 1 | DpbA | 100 | 0.1587 | 2.82E−03 | 9.52E+05 | 2.96E−09 | 0.0176 | 0.9661 |
| 1D12 | 2 | DpbA | 100 | 0.1604 | 7.72E−04 | 7.94E+05 | 9.73E−10 | 0.0078 | 0.9601 |
| 6G8 | 3 | DpbA | 100 | 0.1606 | 9.77E−04 | 1.00E+06 | 9.76E−10 | 0.0177 | 0.9178 |
| 5H5 | 1 | DpbA | 100 | 0.1436 | 9.48E−04 | 1.33E+06 | 7.12E−10 | 0.0218 | 0.8626 |
| 5.00E+06 | 2 | DpbA | 100 | 0.1469 | 5.65E−04 | 7.44E+05 | 7.59E−10 | 0.0083 | 0.9502 |
| msIgG | 3 | DpbA | 100 | 0.0328 | NA | NA | NA | NA | NA |

The 40 expanded clone culture sups were forwarded for BIACORE testing. BIACORE ranking was performed using DbpA chips for all the clones. Dissociation constant ($K_D$) of the tested antibodies were generally in picomolar (pM) range. This was consistent for Octet ranking.

TABLE 5

Biacore Affinity Scouting by DbpA sensor chip

| Clone ID | RU (120 s) | Sample ID | IgG µg/ml | RU/IgG | Ka (1/Ms) | kd(1/s) | KD (M) |
|---|---|---|---|---|---|---|---|
| 1A3 | 681 | 1A3 | 58.7 | 11.6 | | quick off | |
| 1B10 | 794 | 1B10 | 26.3 | 30.2 | 6.00E+04 | 6.00E−04 | 1.00E−08 |
| 1B5 | 670 | 1B5 | >120 | N/A | | quick off | |
| 1B9 | 720 | 1B9 | 72.9 | 9.9 | | quick off | |
| 1C4 | 359 | 1C4 | 37.9 | 9.5 | | | |
| 1D11 | 782 | 1D11 | 59.8 | 13.1 | | | |
| 1D12 | 778 | 1D12 | 39.4 | 19.7 | 6.00E+04 | 4.00E−07 | 6.00E−12 |
| 1D7 | 815 | 1D7 | 48.1 | 16.9 | 7.20E+04 | 6.00E−07 | 8.00E−13 |
| 1E1 | 463 | 1E1 | 26.4 | 17.5 | | | |
| 2B5 | 782 | 2B5 | 17.1 | 45.7 | 1.40E+05 | 2.80E−08 | 2.00E−13 |

TABLE 5-continued

Biacore Affinity Scouting by DbpA sensor chip

| Clone ID | RU (120 s) | Sample ID | IgG µg/ml | RU/IgG | Ka (1/Ms) | kd(1/s) | KD (M) |
|---|---|---|---|---|---|---|---|
| 2C10 | 701 | 2C10 | >120 | N/A | | quick off | |
| 3C2 | 385 | 3C2 | 33.1 | 11.6 | | | |
| 4B3 | 683 | 4B3 | >120 | N/A | | quick off | |
| 4B9 | 716 | 4B9 | 45.9 | 15.6 | | | |
| 4C1 | 431 | 4C1 | 28.9 | 14.9 | | | |
| 4G9 | 826 | 4G9 | 17.6 | 46.9 | 1.60E+05 | 8.00E−07 | 5.00E−12 |
| 4H12 | 462 | 4H12 | 78.7 | 5.9 | | | |
| 4H3 | 428 | 4H3 | 28.7 | 14.9 | | | |
| 4H6 | 188 | 4H6 | 36.6 | 5.1 | | | |
| 5E11 | 310 | 5E11 | 23.4 | 13.2 | | | |
| 5E4 | 225 | 5E4 | 17.4 | 12.9 | | | |
| 5E6 | 776 | 5E6 | 35.9 | 21.6 | | | |
| 5E9 | 290 | 5E9 | 38.1 | 7.6 | | | |
| 5G6 | 752 | 5G6 | 45.2 | 16.6 | | quick off | |
| 5H3 | 790 | 5H3 | 20.5 | 38.6 | 1.40E+05 | 2.00E−08 | 1.50E−13 |
| 5H5 | 791 | 5H5 | 26.8 | 29.5 | 9.00E+04 | 9.00E−06 | 1.00E−10 |
| 6F11 | 422 | 6F11 | >120 | N/A | | quick off | |
| 6G1 | 528 | 6G1 | 14.9 | 35.4 | | | |
| 6G2 | 151 | 6G2 | 33.8 | 4.5 | | | |
| 6G8 | 938 | 6G8 | 17.4 | 53.9 | 2.00E+05 | 5.00E−08 | 2.50E−13 |
| 7A10 | 539 | 7A10 | 47 | 11.5 | | quick off | |
| 7A7 | 391 | 7A7 | 16 | 24.4 | | | |
| 7A8 | 240 | 7A8 | 35.9 | 6.7 | | | |
| 7B8 | 291 | 7B8 | 46 | 6.3 | | | |
| 7G7 | 246 | 7G7 | 79.2 | 3.1 | | | |
| 8B4 | 484 | 8B4 | 32.2 | 15.0 | | | |
| 8B8 | 631 | 8B8 | 82.6 | 7.6 | | quick off | |
| 8C10 | 903 | 8C10 | 27.9 | 32.4 | 1.00E+05 | 1.30E−07 | 1.20E−12 |
| 8C11 | 549 | 8C11 | 40.4 | 13.6 | | quick off | |
| 8G10 | 624 | 8G10 | 29.9 | 20.9 | | | |
| Control Media | 75 | Ms IgG 25 µg/ml | 24.8 | 3.0 | | | |

Phase V: Final selection-Based on the Octet affinity and Biacore affinity ranking, the final 5 clones were chosen. Vials containing the clones (2 vials/clone) were cryo-conserved in liquid nitrogen.

TABLE 6

Summary of Octet and Biacore Affinity Scouting

| Clone Sample ID | Biacore Rank | Biacore Resp. | KD (M) | Octet Rank | DbpA (nM) | Octet Resp. | kdis(1/s) | kon(1/Ms) | Octet KD (M) |
|---|---|---|---|---|---|---|---|---|---|
| 8C10 | #2 | 903 | 1.20E−12 | #2 | 100 | 0.1523 | <1.0E−07 | 3.56E+05 | <1.0E−12 |
| 5H3 | #5 | 790 | 1.50E−13 | #3 | 100 | 0.1555 | 6.06E−04 | 1.04E+06 | 5.80E−10 |
| 4G9 | #3 | 826 | 5.00E−12 | #4 | 100 | 0.1682 | 8.45E−04 | 1.29E+06 | 6.54E−10 |
| 1D12 | #7 | 778 | 6.00E−12 | #5 | 100 | 0.1604 | 7.72E−04 | 7.94E+05 | 9.73E−10 |
| 6G8 | #1 | 938 | 2.50E−13 | #6 | 100 | 0.1606 | 9.77E−04 | 1.00E+06 | 9.76E−10 |

II. Sequencing Results:

Identification and sequencing of the full-length immunoglobulin gene transcripts expressed by mouse hybridomas 6G8 and 8C10 was performed and the translated protein sequences for each antibody agreed with those set forth infra.

Design of Chimera sequence for cloning and expression: Gene synthesis and cloning in expression vector was performed using routine methodology. The entire cloned coding sequences of genes of interest in plasmid were sequenced using appropriate primers. DNA sequences were analyzed with GENE DESIGNER program for confirmation. The confirmed protein sequence of DbpA IgM are identified herein, individually for light chain (LC) and heavy chain (HC), respectively, as SEQ ID NO: 79 and SEQ ID NO: 80.

IV. Chimera Antibody Protein purification and characterization—The respective mouse/human chimera antibody gene was cloned into mammalian expression vector for expression. A chimera IgM antibody was expected to be secreted from the HEK cells. Small scale expression and purification experiments were carried out in HEK cells. (A). 6G8: 0.16 mg of the chimera IgM antibody was purified from 30 mL cell culture, indicating protein expression at 5.4 mg per liter culture when scaling up. (B). 8C10: 1.5 mg of the chimera IgM antibody was purified from 30 mL cell culture, indicating protein expression at 50 mg per liter culture when scaling up. Further purification schemes were developed for large scale production. Validation batches of chimera expression and purification were produced. This demonstrated the feasibility of expression and purification of the chimera IgM antibodies.

Preliminary testing data indicated that these chimeric proteins were purified as ~80 kDa (heavy chain) and ~25 kDa (Light chain) on reducing SDS-PAGE gel, and higher molecular bands were observed on a non-reduced gel, (great than 200 kDa bands). The purified proteins showed as one major dominant peak on HPLC (Retention Time 4.0, corresponding to human IgM molecular weight).

TABLE 7

Kinetics analysis of the BIACORE testing for 6G8 chimera:

| ka (1/Ms) | kd (1/s) | Rmax (RU) | KD (M) |
|---|---|---|---|
| 1.25E+07 | 2.45E−05 | 2557.0 | 1.96E−12 |

Functional testing using lateral flow immunoassays confirmed that these can serve as a good DbpA standard/control for the IgM assay. (A). 6G8: purified samples diluted in BSA/PBS buffer to concentration as 80 ng/mL IgM. Average number of IgM Height/Cutoff (cutoff=3410) were calculated as following Table 8.

TABLE 8

| Sample | IgM Height/Cutoff |
|---|---|
| Negative Control | 0.2 |
| 6G8 (26394.1.a) | 5.6 |
| 6G8 (26394.1.b) | 5.0 |

Recombinant Lyme DbpA antigen was produced and used for mouse immunization and hybridoma cell line development. 5 high affinity mouse monoclonal antibodies were discovered and obtained as hybridoma clones. Two of them, 6G8 and 8C10, were sequenced of the full-length immunoglobulin gene transcripts. Novel sequences of the CDR regions of VH/VL chains were identified. Humanized chimeric antibodies were then designed to include the DbpA-specific CDR domains from mouse IgG and human IgM Fc region for the binding of a secondary anti-human IgM Fc antibody in the immunoassay for detection of IgM.

The two clones, namely 6G8 and 8C10, were sequenced of the full-length immunoglobulin gene transcripts expressed by mouse hybridomas RNA. The mouse IgG VH/VL region genes were synthesized and cloned into a mammalian expression vector. Two chimeric IgM antibodies were expressed and produced from the secreted media. Small scale cell culture and purification experiments in HEK 293 cells were carried out for antibody functional analysis. 0.18 mg of 6G8 and 1.6 mg of 8C10 antibodies were purified from 30 mL cell culture, indicating that antibody titer at 5.4 mg/L and 52 mg/L, respectively, could be achieved when scaling up.

Results demonstrated that the antibodies were purified as 80 kDa (heavy chain) and 25 kDa (light chain) on a reducing SDS-PAGE gel, and higher molecular bands were observed on a non-reduced gel (>500 kDa and other minor bands). The purified antibodies showed as one major dominant peak on HPLC-SEC (Retention Time 3.8, corresponding to human IgM molecular weight). Biacore testing with the DbpA antigen immobilized on CM5 chip demonstrated that it bound well with the purified antibody, confirming that they were correctly folded and expressed. Immunoassay test devices were used to confirm that they served as sensitive DbpA-specific standards and calibrators for an IgM assay.

In summary, novel high affinity DbpA mAb clones have been discovered and identified, in which two of them were disclosed of their epitope-binding sequences on VH/VL and CDR regions. The newly discovered DbpA-specific monoclonal antibodies provided as useful agents in diagnosing Lyme disease and in the detection of Lyme antigen for immunoassay development including POC, EIA and Western blot methods. The recombinant approach for chimeric constructs made it possible to generate an easy platform as serological controls and standards.

From the foregoing description, one skilled in the art can easily ascertain the essential characteristics of the methods and, without departing from the spirit and scope thereof, can make various changes and modifications to adapt it to various usages and conditions.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases referenced herein (e.g., PUBMED, NCBI) are hereby incorporated by reference.

We claim:

1. An antibody or an antigen-binding fragment thereof, comprising:
    a variable heavy chain region (VH) comprising heavy chain complementarity-determining regions $CDR_{H1}$, $CDR_{H2}$, and $CDR_{H3}$, together with a variable light chain region (VL) comprising light chain complementarity-determining regions $CDR_{L1}$, $CDR_{L2}$, and $CDR_{L3}$, wherein,
    $CDR_{H1}$ has the amino acid sequence DYWIE (SEQ ID NO: 7);
    $CDR_{H2}$ has the amino acid sequence EILPGSGSTKD-NERFKG (SEQ ID NO: 8);
    $CDR_{H3}$ has the amino acid sequence REWGYYFDY (SEQ ID NO: 9);
    $CDR_{L1}$ has the amino acid sequence KASQDVSTAVA (SEQ ID NO: 10);
    $CDR_{L2}$ has the amino acid sequence IYWASTRHT (SEQ ID NO: 11); and
    $CDR_{L3}$ has the amino acid sequence QQHYSTPYT (SEQ ID NO: 12).

2. The antibody or the antigen-binding fragment of claim 1, further comprising a framework region (FR).

3. The antibody or the antigen-binding fragment of claim 1, wherein:
    (1) the variable heavy chain region (VH) comprises the sequence set forth in SEQ ID NO: 35; and
    (2) the variable light chain region (VL) comprises the sequence set forth in SEQ ID NO: 36.

4. A method of detecting *Borrelia burgdorferi* decorin-binding protein A (DbpA) antigen in a biological sample, comprising contacting the sample with the antibody of claim 3 and detecting a complex formed between the *Borrelia burgdorferi* DbpA antigen and the antibody.

5. The antibody or the antigen-binding fragment thereof of claim 1, which comprises a single chain antibody fragment (scFV), an Fab fragment, or an F(ab')2 fragment.

6. The antibody or the antigen-binding fragment thereof of claim 1, further comprising a linker (L).

7. The antibody or the antigen-binding fragment thereof of claim 6, wherein the linker (L) is between the variable heavy chain region (VH) and the variable light chain region (VL).

8. The antibody or an antigen-binding fragment thereof of claim 1, wherein the antibody or an antigen-binding fragment further comprises a signal peptide and optionally a label.

9. A kit comprising, in one or more packages, an antibody or an antigen-binding fragment of claim 8 and a container, optionally together with instructions for using the kit.

* * * * *